(12) United States Patent
Eberle et al.

(10) Patent No.: US 7,109,197 B2
(45) Date of Patent: Sep. 19, 2006

(54) N-PHENYL-4-(4-PYRIDYL)-2-PYRIMIDINEAMINE DERIVATIVES

(75) Inventors: Martin Eberle, Basel (CH); Daniel Stierli, Basel (CH); Christian Pillonel, Basel (CH); Hugo Ziegler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 217 days.

(21) Appl. No.: 10/297,737

(22) PCT Filed: Jun. 6, 2001

(86) PCT No.: PCT/EP01/06389

§ 371 (c)(1),
(2), (4) Date: Apr. 23, 2003

(87) PCT Pub. No.: WO01/93682

PCT Pub. Date: Dec. 13, 2001

(65) Prior Publication Data

US 2003/0236256 A1    Dec. 25, 2003

(30) Foreign Application Priority Data

Jun. 8, 2000   (GB) .................................. 0014022.8

(51) Int. Cl.
C07D 401/04 (2006.01)
A01N 43/54 (2006.01)
C07D 213/46 (2006.01)

(52) U.S. Cl. .............. 514/235.8; 514/252.18; 514/275; 544/122; 544/331

(58) Field of Classification Search .............. 544/122, 544/331; 514/235.8, 252.18, 275
See application file for complete search history.

(56) References Cited

U.S. PATENT DOCUMENTS 4,814,338 A    3/1989   Ito
4,873,248 A   10/1989   Katoh
5,075,316 A   12/1991   Hubele
5,612,340 A    3/1997   Zimmermann
5,705,502 A    1/1998   Zimmermann
5,728,708 A    3/1998   Zimmermann

FOREIGN PATENT DOCUMENTS

DE        151 404      10/1981
DE       40 34 762      5/1992

OTHER PUBLICATIONS

Milling, RJ et al., "Mode of Action of the Anilino-Pyrimidine Fungicide Pyrimethanil. 2. Effects on Enzyme Secretion in Botrytis Cinerea", Pesticide Science, vol. 45, No. 1, pp. 43-48 (1995).

*Primary Examiner*—Deepak Rao
(74) *Attorney, Agent, or Firm*—Rebecca Gegick

(57) ABSTRACT

The present invention relates to a method of protecting plants against attack or infestation by phytopathogenic organisms, such as nematodes or especially microorganisms, preferably fungi, bacteria and viruses, or combinations of two or more of these organisms, by applying at least one compound of the formula (I): wherein n is 0 or 1, $R_1$ is halogen, alkoxy, haloalkyl, haloalkoxy or alkyl, $R_2$ is hydrogen, halogen, alkyl, haloalkyl, alkoxy or haloalkoxy, each of $R_3$, $R_4$ and $R_5$ is, independently of the others, hydrogen, lower alkyl or halogen, and $R_6$ is as defined in claim 1. The invention also relates to new compounds of formula (I), their preparation, use and compositions comprising said compound

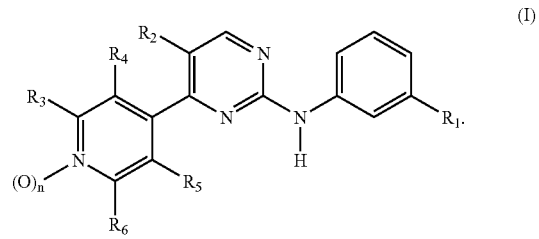

10 Claims, No Drawings

N-PHENYL-4-(4-PYRIDYL)-2-PYRIMIDINEAMINE DERIVATIVES

This application is a 371 of International Application No. PCT/EP01/06389, filed Jun. 6, 2001, the contents of which are incorporated herein by reference.

The present invention relates to a method of protecting plants against attack or infestation by phytopathogenic organisms, such as nematodes or especially microorganisms, preferably fungi, bacteria and viruses, or combinations of two or more of these organisms, by administering an N-phenyl-4-(4-pyridyl)-2-pyrimidineamine derivative as specified hereinafter to a part and/or to the site of a plant, the use of said derivative for protecting plants against said organisms and compositions comprising said derivative. It further relates to novel N-phenyl-4-(4-pyridyl)-2-pyrimidineamine derivatives, their preparation, their use as mentioned above and compositions comprising them.

Certain N-phenyl-4-(4-pyridyl)-2-pyrimidineamine derivatives have already been described in PCT applications WO 95/09851 and WO 95/09853, useful for example for treating tumours.

Surprisingly, it has now been found that these and the additional new N-phenyl-4-(4-pyridyl)-2-pyrimidineamine are effective in plant protection and related areas, showing advantageous properties in the treatment of plant diseases caused by organisms.

The N-phenyl-4-(4-pyridyl)-2-pyrimidineamine derivatives to be used according to the invention are those of the formula I,

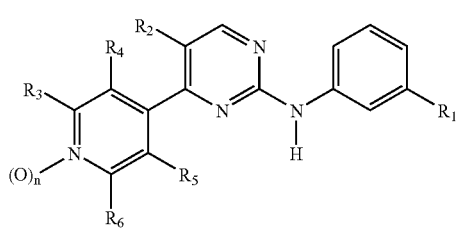

wherein n is 0 or 1, $R_1$ is halogen, alkoxy, haloalkyl, haloalkoxy or alkyl, $R_2$ is hydrogen, halogen, alkyl, haloalkyl, alkoxy or haloalkoxy, each of $R_3$, $R_4$ and $R_5$ is, independently of the others, hydrogen, lower alkyl or halogen, and $R_6$ is a) hydrazino, that is unsubstituted or one- to threefold substituted by optionally substituted alkyl and/or optionally substituted acyl, b) cyclohexylamino, tetrahydro-4H-pyranyl-4-amino, pyrrolidine-3-amino, 2- or 3-tetrahydro-furylamino, all optionally substituted by amino, hydroxy, alkoxy, alkyl or alkoxyalkyl, c) piperazinyl that is optionally substituted by amino, amino-lower alkyl, hydroxy, alkoxy, alkyl or alkoxyalkyl, d) morpholinyl that is optionally substituted by amino, amino-lower alkyl, hydroxy, alkoxy, alkyl or alkoxyalkyl, e) oxazolidinyl that is optionally substituted by amino, amino-lower alkyl, hydroxy, hydroxy-lower alkyl, alkoxy, alkyl or alkoxyalkyl, f) thiazolidinyl that is optionally substituted by amino, amino-lower alkyl, hydroxy, hydroxy-lower alkyl, alkoxy, alkyl or alkoxyalkyl, g) imidazolidinyl that is optionally substituted by amino, amino-lower alkyl, hydroxy, hydroxy-lower alkyl, alkoxy, alkyl or alkoxyalkyl, h) amino or mono- or di-(lower alkyl)amino wherein the lower alkyl moieties are unsubstituted or substituted by one or more (preferably 1 to 3, especially 1 or 2) substitutents independently selected from the group consisting of unsubstituted amino, N-mono- or N,N-di-(lowe ralkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkylcarbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfoxyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl (including formylpiperazinyl), optionally substituted heteroaryl and optionally substituted heteroaryloxy i) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino, j) N-(optionally substituted alkyl)-N-(optionally substituted lower alkanoyl)-amino, k) N-(optionally substituted alkyl)-N-(optionally substituted alkoxycarbonyl)-amino, l) N-(optionally substituted alkyl)-N-(N',N'-mono- or di-[optionally substituted alkyl]-aminocarbonyl)-amino, or m) N=C($R_7$,$R_8$) wherein $R_7$ is hydrogen, alkyl, amino, mono- or di-alkylamino and $R_8$ is amino, mono- or dialkylamino or wherein $R_7$ and $R_8$, together with the binding carbon atom, form a saturated five- to seven-membered ring with 0, 1 or 2 ring nitrogen atoms that is optionally substituted by one or more substituents, preferably 1 to 3 substituents, especially lower alkyl;

or a salt thereof.

The general symbols and expressions used above preferably are defined as below:

Halogen is fluorine, bromine, iodine or preferably chlorine.

Alkoxy is preferably $C_1$–$C_{16}$alkoxy, more preferably $C_1$–$C_8$alkoxy, especially lower alkoxy, and is linear or branched. Lower alkoxy is preferably methoxy or ethoxy.

Haloalkyl is preferably $C_1$–$C_{16}$alkyl, more preferably $C_1$–$C_8$alkyl, especially lower alkyl, that is linear or branched and is substituted by one or more, for example in the case of halo-ethyl up to six, halogen atoms, especially fluorine. Preferred is trifluoromethyl or 2,2,2-trifluoroethyl.

Haloalkoxy is preferably $C_1$–$C_{16}$alkoxy, more preferably $C_1$–$C_8$alkoxy, especially lower alkoxy, that is linear or branched and that is substituted by one or more, for example in the case of halo-ethyl up to five, halogen atoms, especially fluorine; trifluoromethoxy and 1,1,2,2-tetrafluoroethoxy are especially preferred.

Alkyl—as a group per se se and as a structural element of other groups and compounds, such as alkylamino, alkanoylamino, alkanoyloxy, alkylthio, alkylsulfoxyl, alkylsulfonyl—is preferably $C_0$–$C_{16}$alkyl, more preferably $C_1$–$C_8$alkyl, especially lower alkyl, and is linear i.e. methyl, ethyl, propyl, butyl, pentyl or hexyl, or branched one or more times, e.g. isopropyl, isobutyl, sec.-butyl, tert.-butyl, isopentyl, neopentyl or isohexyl. Lower alkyl is preferably methyl or ethyl.

Optionally substituted means that the respective moiety is unsubstituted (=bearing only hydrogen instead of a substitutent) or substituted by one or more, especially 1 to 3, substituents independently selected from the group consisting of amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo bound to a carbon that is not directly bound to a heteroatom, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfinyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl (including formylpiperazinyl), optionally substituted heteroaryl and optionally substituted heteroaryloxy (with the proviso that in the case of optionally substituted heteroaryl and optionally substituted heteroaryloxy a heteroaryl substituent is preferably not substituted by substituted heteroaryloxy). Preferred substituents are lower alkoxy, hydroxy and/or halogen, if not mentioned otherwise.

For example, substituents in the optionally substituted alkyl group are one or more substitutents independently selected from the group of substituents mentioned in the last paragraph.

Alkenyl—as a group per se se and as a structural element of other groups and compounds, such as alkenoylamino—is preferably $C_2$–$C_{16}$-, more preferably $C_2$–$C_8$-, especially $C_3$–$C_8$-, very especially $C_3$–$C_7$-, for example $C_3$–$C_4$-alkenyl, and is either straight-chained, for example vinyl, 1-methylvinyl, allyl, 1-butenyl or 2-hexenyl, or branched, for example isopropenyl. Preferably (for reasons of chemical stability) the C-atoms in alkenyl that are bonded to a heteroatom (e.g. N, O or S) do not carry the double bond.

Alkynyl—as a group per se and as a structural element of other groups and compounds, such as alkynoylamino—is preferably $C_2$–$C_{16}$-, more preferably $C_2$–$C_8$-, especially $C_3$–$C_8$-, very especially $C_3$–$C_7$-, for example $C_3$–$C_4$-alkenyl, and is either straight-chained, for example propargyl, 2-butynyl or 5-hexynyl, or branched, for example 2-ethynylpropyl or 2-propargyl-isopropyl. Preferably (for reasons of chemical stability) the C-atoms in alkynyl that are bonded to a heteroatom (e.g. N, O or S) do not carry the triple bond.

One—to threefold substituted hydrazino preferably carries one to three substituents independently selected from the group consisting of alkyl, haloalkyl, such as trifluoromethyl, hydroxyalkyl, such as 2-hydroxyethyl, hydroxymethyl or 1-hydroxymethyl-n-propyl, alkoxyalkyl, such as 2-methoxyethyl, ethoxymethyl or 1-methoxymethyl-n-propyl, and acyl. Optionally substitued alkyl is preferably as defined above.

Acyl is preferably $C_1$–$C_{16}$alkanoyl, more preferably lower alkanoyl, and is linear or branched. Lower alkanoyl is preferably formyl, acetyl or in a broader sense of the invention propionyl or butyryl.

Substitutents in the optionally substituted acyl group are preferably one or more substituents independently selected from halogen (more preferably fluorine), hydroxy or alkoxy (more preferably methoxy or ethoxy), e.g. in trifluoroacetyl or pentafluoropropionyl.

Substituted hydrazinyl is preferably hydroxy-lower alkyl-hydrazino; 2-hydroxyethyl is an especially preferred substituent of the hydrazino group.

Cyclohexyl-amino substituted by amino is preferably 2- or 4-amino-cyclohexyl-amino.

Piperazinyl is preferably 1-piperazinyl. As substituted piperazinyl, piperazinyl substituted by amino-lower alkyl is preferred, especially 4-(2-amino-ethyl)-piperazin-1-yl.

Morpholinyl is preferably 4-morpholinyl (=morpholino). Lower alkylamino $R_6$ substituted by morpholinyl is preferably 2-morpholin-4-yl-ethylamino. Substituted morpholinyl is preferably 3-alkyl- or 3,5-dialkylmorpholino, more preferably 3-methyl- or 3,5-dimethylmorpholino.

Formyl-piperazinyl is preferably 4-formyl-piperazinyl.

Lower alkyl that is substituted by unsubstituted mono- or di-(lower alkyl)-amino in mono- or di-(lower alkyl)-amino $R_6$ with one or (if two are present) both moieties substituted is preferably lower alkyl that is substituted by N-mono- or N,N-di-(lower alkyl)amino, preferably dimethylamino; preferred is lower alkylamino that is substituted by N-mono- or N,N-di-(lower alkyl)amino, most preferably 3-(dimethylamino)-1-methyl-n-propylamino.

Lower alkyl substituted by amino in mono- or di-(lower alkyl)-amino $R_6$ with one or (if two are present) both lower alkyl moieties substituted is preferably lower alkyl substituted by one or two amino groups; preferred is mono-lower alkyl that is substituted by one or more, especially 1 or 2, amino groups, especially 2-amino-ethylamino or 3-amino-n-propylamino.

(Lower alkoxy)-lower alkoxy as substituent of a substituted lower alkyl moiety of mono- or di-(lower alkyl)-amino is preferably (methoxy)-methoxy.

A preferred di-(lower alkyl)amino $R_6$ wherein the lower alkyl moieties are substituted by (lower alkoxy)-lower alkoxy and lower alkoxy is N-(methoxymethyl)-N-{2-[(methoxy)-methoxy]-1-methyl-ethyl}-amino.

Hydroxy-lower alkylamino is preferably hydroxy-lower alkyl that carries one or more, especially one or two, hydroxy groups, more preferably 2-hydroxy-ethylamino. Lower alkylamino substituted by hydroxy-lower alkylamino is preferably 3-(2-hydroxy-ethyl-amino)-prop-1-yl-amino Oxo is not bonded to a carbon atom that is bound to a heteroatom, such as nitrogen, sulfur or oxygen, in order to avoid overlap with acyl substituents.

Lower alkylamino-carbonylamino is preferably methylamino-carbonyl-amino.

Di-lower alkylamino is preferably dimethylamino.

Alkoximino is preferably $C_1$–$C_{16}$-, more preferably $C_1$–$C_8$-, most preferably lower alkoximino.

Optionally substituted hydrazono is preferably hydrazono or hydrazono substituted with one of the substituents defined above for "optionally substituted". Hydrazono or N-lower alkylhydrazono is preferred.

Lower alkyl substituted by hydroxy in mono- or di-(lower alkyl)-amino $R_6$ with one or (if two are present) both lower alkyl moieties substituted is preferably lower alkylamino that carries one or more hydroxy substituents, especially 1 or 2 hydroxy substituents, preferred is mono-lower alkylamino that is substituted by one or two hydroxy groups, especially 2- or 3-hydroxy-n-propylamino, 1,1-dimethyl-3-hydroxy-n-propylamino, 1-n-propyl-2-hydroxy-ethylamino, 1,1-dimethyl-2-hydroxy-ethylamino, 1-ethyl-2-hydroxy-ethylamino, 2-hydroxy-1-(hydroxy-methyl)-ethylamino, 2-hydroxy-1-methyl-ethylamino or 2-hydroxy-1-(sec-butyl)-ethylamino.

Lower alkyl substituted by lower alkoxy in mono- or di-lower alkylamino $R_6$ with one or (if two are present) both lower alkyl moieties substituted is preferably lower alkyl that is substituted by one or more, especially 1 or 2, lower alkoxy groups; preferred is mono-lower alkylamino $R_6$ wherein the lower alkyl moieties are substituted by lower alkoxy, especially 2-methoxy-ethylamino, 1-ethyl-2-methoxy-ethylamino, 2-methoxy-1-methyl-ethylamino, 2-methoxy-2-methyl-ethylamino, 1,1-dimethyl-2-methoxy-ethylamino, 1,1-dimethyl-3-methoxy-n-propylamino or 3-methoxy-propylamino.

Lower alkyl substituted by carboxy in mono- or di-lower alkylamino $R_6$ with one or (if two are present) both lower alkyl moieties substituted is preferably carboxymethyl.

Lower alkoxycarbonyl-amino is preferably ethoxycarbonyl-amino. Preferred is mono-lower alkylamino $R_6$ that is substituted by lower alkoxycarbonylamino, especially 3-[N-(ethoxycarbonyl)-amino]-n-propylamino.

Lower alkyl substituted by cyano, guanidyl, lower alkanoyl-amino, lower alkylaminocarbonylamino, amidino, di-lower alkylamino-cyclohexyl, lower alkoxycarbonyl, carbamoyl, N-hydroxy-carbamoyl, piperazinyl, lower alkanoyl-piperazinyl, formylpiperazinyl, tetrahydro-4H-pyranyl-4-amino, pyrrolidine-3-amino, 2- or 3-tetrahydro-furylamino, optionally substituted heteroaryl or optionally substituted heteroaryloxy is preferably di- or tri-methylene-amino substituted by those substituents, the substituents preferably being in the ω-position. The same holds true for other substitutents of lower alkyl in substituted mono- or di-lower alkylamino that are not defined in more detail.

Heteroaryl (in the term heteroaryl and heteroaryloxy) is a cyclic aromatic group with one or two rings with a total of 5 to 12 ring members, 1 to 3 members of which are hetero atoms, preferably selected from the group consisting of oxygen, sulphur and nitrogen. 1 to 2 benzene rings may be condensed onto the heterocycle, whereby the binding to the residual molecule takes place either via the hetero or the benzene moiety. Preferably, heteroaryl is benzimidazolyl, benzisoxazolyl, benzisothiazolyl, benzocoumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl (especially 2- or 3-furyl), imidazolyl (especially 1-imidazolyl), indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]pyridyl, pyridyl (especially 2-, 3- or 4-pyridyl), pyrimidyl, pyrrolyl, tetrazolyl (especially tetrazol-1-yl), oxadiazolyl, thiadiazolyl, thiazolyl (especially 2-, 4- or 5-thiazolyl), thienyl (especially 2- or 3-thienyl), triazinyl (especially 1,3,5-triazinyl) and triazolyl (especially 1,2,4-triazol-1-yl). Furyl, pyridyl, imidazolyl and triazolyl are preferred.

The heteroaryl and heteroryloxy moiety may be substituted by one or more, preferably one to three identical or different substitutents selected from the group comprising halogen, $C_1$–$C_6$-alkyl, $C_3$–$C_6$-cycloalkyl, halogen-$C_1$–$C_6$-alkyl, hydroxy, $C_1$–$C_6$-alkoxy, halogen-$C_1$–$C_6$-alkoxy, $C_1$–$C_6$-alkylthio, halogen-$C_1$–$C_6$-alkylthio, $C_1$–$C_6$-alkyll, halogen-$C_1$–$C_6$-alkyll, $C_1$–$C_6$-alkylsulfinyl, halogen-$C_1$–$C_6$-alkylsulfinyl, $C_1$–$C_6$-alkylsulfonyl, halogen-$C_1$–$C_6$-alkylsulfonyl, $C_1$–$C_6$-alkyl-carbonyl, halogen-$C_1$–$C_6$-alkyl-carbonyl, carboxyl, $C_1$–$C_6$-alkoxycarbonyl, halogen-$C_1$–$C_6$-alkoxycarbonyl, aminocarbonyl, $C_1$–$C_6$-alkylaminocarbonyl, di-($C_1$–$C_6$-alkyl)-aminocarbonyl, whereby the alkyl groups may be identical or different, amino, $C_1$–$C_6$-alkylamino, di-($C_1$–$C_6$-alkyl)-amino, $NO_2$, CN, $C_2$–$C_6$-alkenyl or $C_2$–$C_6$-alkynyl.

Alkanoylamino is preferably $C_1$–$C_{16}$alkanoylamino, more preferably $C_1$–$C_6$-alkanoylamino, most preferably lower alkanoylamino, especially formylamino, acetylamino, propionylamino, butanoylamino and pentanoylamino. Preferred substituents of the alkanoyl group are one or more, especially 1 to five, substituents independently selected from the group consisting of fluorine, hydroxy and methoxy. Especially preferred are trifluoroacetylamino and 2-hydroxy-propionylamino.

A five- to seven-membered ring with 0, 1 or 2 ring nitrogen atoms formed from $R_7$ and $R_8$ together with the binding carbon atom preferably has 2 ring nitrogen atoms that are immediately adjacent (=bound) to the binding carbon atom, for example forming an imidazolidin-2-ylidene, tetrahydropyrimidin-2-ylidene or hexahydro-1,3-diazepin-2-ylidene moiety, and is optionally substituted, especially unsubstituted or substituted by one to three lower alkyl moieties, especially methyl, etyhl, propyl or isopropyl, which may be bound to carbon or nitrogen ring atoms.

As substituents $R_6$, those mentioned specifically in Table A given below and/or in the Examples are especially preferred and can be combined with the other moieties $R_1$ to $R_5$ in formula I.

Within the scope of this text, the term "lower" denotes radicals having up to and including 7, preferably up to and including 4, carbon atoms. Unless otherwise indicated in the context concerned, lower alkyl is preferably methyl or ethyl. In the case of alkenyl or alkinyl, "lower" means $C_2$–$C_7$-, more preferably $C_3$–$C_7$-, such as $C_3$–$C_4$-alkenyl or -alkinyl, and the double- or triple bond preferably does not start from a heteroatom, especially S, N or O, most especially one carrying a hydrogen, such as NH, OH or SH.

The compounds of formula I can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid. Mono, di- or, if other basic groups, such as amino or guanidyl groups, are present in the radical $R_6$, poly-acid addition salts can be formed.

Compounds of formula I having acidic groups, for example a free carboxy group in the radical $R_6$, can form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

Compounds of formula I that possess both acidic and basic groups can form internal salts.

The pyridine-N-oxides of formula I (n=1) can form acid addition salts with strong acids, such as hydrochloric acid, nitric acid, phosphoric acid or sulfonic acids, such as benzene-sulfonic acid. The compounds of formula I with n=1 are new and thus form an especially preferred embodiment of the invention, as their use and process of manufacture.

Formula I is meant to include all the possible isomeric forms, as well as mixtures, e.g. racemic mixtures, and any [E/Z] mixtures.

In view of the close relationship between the compounds of formula I in free form and in the form of their salts, including also salts that can be used as intermediates, for example in the purification of the compounds of formula I or in order to identify those compounds, herein-before and hereinafter any reference to the (free) compounds is to be understood as including also the corresponding salts, where appropriate and expedient.

Where hereinbefore and hereinafter reference is made that "compounds can be used according to the invention" or a "method for applying a compound of formula I" or to "compounds to be used according to the invention, this refers to the fact that the invention relates to any one or more of (i) the use of a compound of the formula I, or a salt thereof, for protection of a plant against attack by a phytopathogenic organism or the treatment of a plant infested by a phytopathogenic organism, said use comprising the administration of a compound of the formula I or a salt thereof, or a composition comprising said compound or salt and a carrier material acceptable for agricultural purposes, to any one or more selected from the group consisting of a plant, a part of a plant, seeds and the locus of a plant;

(ii) a method of protecting a plant against attack by a phytopathogenic organism and/or the treatment of a plant infested by a phytopathogenic organism, said method comprising administering a compound of the formula I or a salt thereof, or a composition comprising said compound or salt and a carrier material acceptable for agricultural purposes, to any one or more selected from the group consisting of a plant, a part of a plant, seeds and the locus of a plant, preferably if in need of such treatment;

(iii) a process for protecting a plant against attack by a phytopathogenic organism and/or the treatment of a plant infested by a phytopathogenic organism, said process comprising administering a compound of the formula I or a salt thereof, or a composition comprising said compound or salt and a carrier material acceptable for agricultural purposes, to any one or more selected from the group consisting of a plant, a part of a plant, seeds and the locus of a plant; and/or (iv) a composition (useful) for protecting a plant against attack by a phytopathogenic organisms and/or the treatment of a plant infested by a phytopathogenic organism, said composition comprising a compound of the formula I or a salt thereof and a carrier material acceptable for agricultural purposes.

Any of these uses, methods, processes or compositions is meant as preferred part of the invention where the respective reference given above in citation marks is/are made.

In the preferred or more specific embodiments of the invention given above and below, the definitions given above can be used instead of more general terms, thus leading to preferred embodiments of the invention.

The compounds of formula I may be used preventatively and/or curatively in the agrarian sector and related fields as active ingredients for controlling plant pests. The active ingredients of formula I according to the invention are notable for their good activity even at low concentrations, for their good plant tolerance and for their environmentally friendly nature. They have very advantageous, especially systemic, properties and may be used to protect a plurality of cultivated plants. Using the active ingredients of formula I on plants or plant parts (fruit, flowers, leaves, stems, tubers, roots) of various crops, the pests appearing can be controlled or destroyed, whereby the parts of plants which grow later also remain protected, e.g. from phytopathogenic microorganisms.

The compounds of formula I may additionally be used as a dressing to treat seeds (fruits, tubers, corms) and plant cuttings to protect against fungal infections and against phytopathogenic fungi occurring in the soil.

The compounds of formula I are effective for example against the following classes of related phytopathogenic fungi: *Fungi imperfecti* (e.g. *Botrytis, Pyricularia, Helminthosporium, Fusarium, Septoria, Cercospora* and *Altemaria*); *Basidiomycetes* (e.g. *Rhizoctonia, Hemileia, Puccinia*); *Ascomycetes* (e.g. *Venturia* and *Erysiphe, Podosphaera, Monilinia, Uncinula*) and *Oomycetes* (e.g. *Phytophthora, Pythium, Plasmopara*).

Target crops for the plant-protecting usage in terms of the invention are for example the following plant cultivars: cereals (wheat, barley, rye, oats, rice, maize, sorghum and related species); beet (sugar beet and fodder beet); pome, stone and berry fruit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, nuts, coffee, aubergines, sugar cane, tea, pepper, vines, hops, bananas and natural rubber plants, as well as ornamental plants.

Further areas of application for the active ingredients according to the invention are the protection of stores and material, where the storage matter is protected against putrescence and mould.

The compounds of formula I are used in unchanged form or preferably together with customary excipients in formulation techniques. To this end, they are conveniently processed in known manner e.g. into emulsion concentrates, coatable pastes, directly sprayable or diluable solutions, diluted emulsions, wettable powders, soluble powders, dusts or granules, e.g. by encapsulation into for example polymeric materials. As with the type of medium, the application processes, such as spraying, atomizing, dusting, scattering, coating or pouring are similarly chosen according to the desired aims and the prevailing conditions.

Suitable substrates and additives may be solid or liquid and are useful substances in formulation techniques, e.g. natural or regenerated mineral substances, dissolving aids, dispersants, wetting agents, tackifiers, thickeners, binding agents or fertilizers.

The compounds of formula I may be mixed with further active ingredients, e.g. fertilizers, ingredients providing trace elements or other plant protection compositions, especially further fungicides. In doing so, unexpected synergistic effects may occur.

Preferred additions to the mixture are:

Azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazole;

pyrimidinyl carbinoles, such as ancymidol, fenarimol, nuarimol;

2-amino-pyrimidines, such as bupirimate, dimethirimol, ethirimol;

morpholines, such as dodemorph, fenpropidine, fenpropimorph, spiroxamin, tridemorph;

anilinopyrimidines, such as cyprodinil, mepanipyrim, pyrimethanil;

pyrroles, such as fenpiclonil, fludioxonil;

phenylamides, such as benalaxyl, furalaxyl, metalaxyl, r-metalaxyl, ofurace, oxadixyl;

benzimidazoles, such as benomyl, carbendazim, debacarb, fuberidazole, thiabendazole;

dicarboximides, such as chlozolinate, dichlozoline, iprodione, myclozoline, procymidone, vinclozoline;

carboxamides, such as carboxin, fenfuram, flutolanil, mepronil, oxycarboxin, thifluzamide;

guanidines, such as guazatine, dodine, iminoctadine;

strobilurines, such as azoxystrobin, kresoxim-methyl, metominostrobin, SSF-129, trifloxystrobin;

dithiocarbamates, such as ferbam, mancozeb, maneb, metiram, propineb, thiram, zineb, ziram;

N-halomethylthio, such as captafol, captan, dichlofluanid, fluoromides, folpet, tolyfluanid;

Cu compounds, such as Bordeaux mixture, copper hydroxide, copper oxychloride, copper sulfate, cuprous oxide, mancopper, oxine-copper;

nitrophenol-derivatives, such as dinocap, nitrothal-isopropyl;

organo-p-derivatives, such as edifenphos, iprobenphos, isoprothiolane, phosdiphen, pyrazophos, tolclofos-methyl;

Various others, such as acibenzolar-S-methyl, anilazine, blasticidin-S, chinomethionate, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, iprovalicarb, IKF-916, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin.

One preferred method of application of an active ingredient of formula I or of an agrochemical composition containing at least one of these active ingredients is foliar application. The frequency and amount of application depend on the severity of the attack by the pathogen in question. However, the active ingredients I may also reach the plants through the root system via the soil (systemic action) by drenching the locus of the plant with a liquid preparation or by incorporating the substances into the soil in solid form, e.g. in the form of granules (soil application). In rice cultivations, these granules may be dispensed over the flooded paddy field. The compounds I may however also be applied to seed grain to treat seed material (coating), whereby the grains or tubers are either drenched in a liquid preparation of the active ingredient or coated with a solid preparation.

The compositions are produced in known manner, e.g. by intimately mixing and/or grinding the active ingredient with extenders such as solvents, solid carriers and optionally surfactants.

The agrochemical compositions normally contain 0.1 to 99 percent by weight, especially 0.1 to 95 percent by weight, of active ingredient of formula I, 99.9 to 1 percent by weight, especially 99.8 to 5 percent by weight, of a solid or liquid additive and 0 to 25 percent by weight, especially 0.1 to 25 percent by weight, of a surfactant.

Favourable application rates are in general 1 g to 2 kg of active substance (AS) per hectare (ha), preferably 10 g to 1 kg AS/ha, especially 20 g to 600 g AS/ha. For usage as a seed dressing, it is advantageous to use dosages of 10 mg to 1 g active substance per kg of seed grain.

While concentrated compositions are preferred for commercial usage, the end user normally uses diluted compositions.

The compositions may also contain further additives, such as stabilizers, anti-foaming agents, viscosity regulators, binding agents or tackifiers, as well as fertilizers or other active ingredients to achieve special effects.

Formulations may be prepared analogously to those described for example in WO 97/33890.

In the following, examples for test systems that demonstrate the efficiency of the compounds of the formula I (designated as "active ingredient" or "test compounds") in plant protection are provided:

BIOLOGICAL ASSAYS

Assay B-1: Effect against *Puccinia graminis* on Wheat (Brownrust on Wheat)

a) Residual Protective Activity 1 week old wheat plants cv. Arina are treated with the formulated testcompound (0.02% active substance) in a spray chamber. Two days after application wheat plants are inoculated by spraying a spore suspension ($1\times10^5$ uredospores/ml) on the test plants. After an incubation period of 1 day at 20° C. and 95% relative atmospheric humidity (r. h.)

plants are kept for 9 days at 20° C. and 60% r.h.in a greenhouse. The disease incidence is assessed 10 days after inoculation.

b) Systemic Activity

An aqueous spray liquor prepared from the formulated testcompound (0.002% active substance, based on the volume of soil) is poured onto wheat plants 5 days after sowing. Care is taken that the spray liquor does not come into contact with the above-ground parts of the plant. 48 hours later, the plants are inoculated with a spore suspension of the fungus. After an incubation period of 48 hours (95 to 100% r.h. at 20° C.), the plants are placed in a greenhouse at 20° C. 12 days after infection, the disease incidence is evaluated.

Assay B-2: Effect Against *Phytophthora infestans* on Tomatoes (Late Blight on Potato)

a) Residual Protective Activity 3 week old tomato plants cv. Roter Gnom are treated with the formulated testcompound (0.02% active substance) in a spray chamber. Two day after application the plants are inoculated by spraying a sporangia suspension ($2 \times 10^4$ sporangia/ml) on the test plants. After an incubation period of 4 days at 18° C. and 95% r. h. in a growth chamber the disease incidence is assessed.

b) Systemic Activity

An aqueous suspension prepared from the formulated test compound (0.002% active substance, based on the volume of soil) is poured onto tomato plants which have been cultivated for three weeks. Care is taken that the spray liquor does not come into contact with the above-ground parts of the plant. 48 hours later, the plants are inoculated with a sporangia suspension of the fungus. Evaluation of the disease incidence takes place 5 days after infection, during which period conditions of 90 to 100% r.h. and 20° C. are maintained.

Assay B-3: Effect Against *Phytophthora infestans*/Potato (Late Blight on Potato)

5 week old potato plants cv. Bintje are treated with the formulated testcompound (0.02% active substance) in a spray chamber. Two days after application the plants are inoculated by spraying a sporangia suspension ($1.4 \times 10^5$ sporangia/ml) on the test plants. After an incubation period of 4 days at 18° C. and 95% r. h. in a growth chamber the disease incidence is assessed.

Assay B-4: Effect Against *Plasmopara viticola* on Grapevine (Grape Downy Mildew)

5 week old grape seedlings cv. Gutedel are treated with the formulated testcompound (0.02% active substance) in a spray chamber. One day after application grape plants are inoculated by spraying a sporangia suspension ($4 \times 10^4$ sporangia/ml) on the lower leaf side of the test plants. After an incubation period of 6 days at 22° C. and 95% r. h. in a greenhouse the disease incidence is assessed.

Assay B-5: Residual Protective Activity Against *Venturia inaegualis* on Apples (Scab on Apple)

4 week old apple seedlings cv. McIntosh are treated with the formulated testcompound (0.02% active substance) in a spray chamber. One day after application apple plants are inoculated by spraying a spore suspension ($4 \times 10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Assay B-6: Effect Against *Erysiphe graminis* on Barley (Powdery Mildew on Barley)

a) Residual Protective Activity

Barley plants of approximately 8 cm height are sprayed to drip point with an aqueous spray liquor prepared from wettable powder of the active ingredient (0.02% active substance), and dusted 3 to 4 hours later with conidia of the fungus. The infected plants are placed in a greenhouse at 22°. 12 days after infection, the fungal attack is evaluated.

b) Systemic Activity

An aqueous spray liquor prepared from the formulated test compound (0.002% active substance, based on the volume of soil) is poured onto barley plants of approximately 8 cm height. Care is taken that the spray liquor does not come into contact with the abouve-ground parts of the plant. 48 hours later, the plants are dusted with conidia of the fungus. The infected plants are placed in a greenhouse at 22° C. 12 days after infection, the disease incidence is evaluated.

Assay B-7: *Botrytis cinerea*/Grape (*Botrytis* on Grapes)

5 week old grape seedlings cv. Gutedel are treated with the formulated testcompound (0.02% active substance) in a spray chamber. Two days after application grape plants are inoculated by spraying a spore suspension ($1 \times 10^6$ conidia/ml) on the test plants. After an incubation period of 4 days at 21° C. and 95% r. h. in a greenhouse the disease incidence is assessed.

Assay B-8: Effect Against *Botrytis cinerea*/Tomato (*Botrytis* on Tomatoes)

4 week old tomato plants cv. Roter Gnom are treated with the formulated testcompound 0.02% active substance) in a spray chamber. Two days after application tomato plants are inoculated by spraying a spore suspension ($1 \times 10^5$ conidia/ml) on the test plants. After an incubation period of 4 days at 20° C. and 95% r. h. in a greenhouse the disease incidence is assessed.

Assay B-9: Effect Against *Pyricularia oryzae*/Rice (Rice Blast)

3 week old rice plants cv. Sasanishiki are treated with the formulated testcompound (0.02% active substance) in a spray chamber. Two days after application rice plants are inoculated by spraying a spore suspension ($1 \times 10^5$ conidia/ml) on the test plants. After an incubation period of 6 days at 25° C. and 95% r. h. the disease incidence is assessed.

Assay B-10: Effect Against *Pyrenophora teres* (*Helminthosporium*)/Barley (Net Blotch on Barley)

1 week old barley plants cv. *Regina* are treated with a formulated testcompound (0.02% active substance) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation.

Assay B-11: Effect Against *Fusarium culmorum*/Wheat (*Fusarium* Head Blight on Wheat)

A conidia suspension of *F. culmorum* ($7 \times 10^5$ conidia/ml) is mixed with the formulated test compound (0.002% active substance). The mixture is applied into a pouch which has been equipped before with a filter paper. After the application wheat seeds (cv. Orestis) are sown into the upper fault of the filter paper. The prepared pouches are then incubated for 11 days at approx. 10–18° C. and a relative humidity of 100% with a light period of 14 hours. The evaluation is made by assessing the degree of disease occurrence in the form of brown lesions on the roots.

Assay B-12: Effect Against *Septoria nodorum*/Wheat (*Septoria* Leaf Spot on Wheat)

1 week old wheat plants cv. Arina are treated with a formulated test compound (0.02% active substance) in a spray chamber. One day after application wheat plants are inoculated by spraying a spore suspension ($5 \times 10^5$ conidia/ml) on the test plants. After an incubation period of 1 day at 20° C. and 95% r.h. plants are kept for 10 days at 20° C. and 60% r.h. in a greenhouse. The disease incidence is assessed 11 days after inoculation.

Preferred among the compounds to be used according to the invention is a compound of the following tables.

TABLE 1

Compounds of the general formula I.1, in which $R_1$ is fluorine, $R_2$ and $R_3$ are hydrogen, n is 0, and $R_6$ corresponds in each case to one of the lines of Table A.

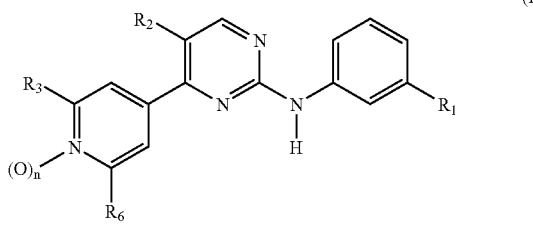

Table 2

Compounds of the general formula I.1, in which $R_1$ is chlorine, $R_2$ and $R_3$ are hydrogen, n is 0, and $R_6$ corresponds in each case to one of the lines of Table A.

Table 3

Compounds of the general formula I.1, in which $R_1$ is bromine, $R_2$ and $R_3$ are hydrogen, n is 0, and $R_6$ corresponds in each case to one of the lines of Table A.

Table 4

Compounds of the general formula I.1, in which $R_1$ is trifluoromethyl, $R_2$ and $R_3$ are hydrogen, n is 0, and $R_6$ corresponds in each case to one of the lines of Table A.

Table 5

Compounds of the general formula I.1, in which $R_1$ is trifluoromethoxy, $R_2$ and $R_3$ are hydrogen, n is 0, and $R_6$ corresponds in each case to one of the lines of Table A.

Table 6

Compounds of the general formula I.1, in which $R_1$ is chlorodifluoromethoxy, $R_2$ and $R_3$ are hydrogen, n is 0, and $R_6$ corresponds in each case to one of the lines of Table A.

Table 7

Compounds of the general formula I.1, in which $R_1$ is 2,2,2-trifluoroethoxy, $R_2$ and $R_3$ are hydrogen, n is 0, and $R_6$ corresponds in each case to one of the lines of Table A.

Table 8

Compounds of the general formula I.1, in which $R_1$ is 1,1,2,2-tetrafluoroethoxy, $R_2$ and $R_3$ are hydrogen, n is 0, and $R_6$ corresponds in each case to one of the lines of Table A.

Table 9

Compounds of the general formula I.1, in which $R_1$ is fluorine, $R_2$ is methyl, $R_3$ is hydrogen, n is 0, and $R_6$ corresponds in each case to one of the lines of Table A.

Table 10

Compounds of the general formula I.1, in which $R_1$ is chlorine, $R_2$ is methyl, $R_3$ is hydrogen, n is 0, and $R_6$ corresponds in each case to one of the lines of Table A.

Table 11

Compounds of the general formula I.1, in which $R_1$ is bromine, $R_2$ is methyl, $R_3$ is hydrogen, n is 0, and $R_6$ corresponds in each case to one of the lines of Table A.

Table 12

Compounds of the general formula I.1, in which $R_1$ is trifluoromethoxy, $R_2$ is methyl, $R_3$ is hydrogen, n is 0, and $R_6$ corresponds in each case to one of the lines of Table A.

Table 13

Compounds of the general formula I.1, in which $R_1$ is chlorodifluoromethoxy, $R_2$ is methyl, $R_3$ is hydrogen, n is 0, and $R_6$ corresponds in each case to one of the lines of Table A.

Table 14

Compounds of the general formula I.1, in which $R_1$ is 2,2,2-trifluoroethoxy, $R_2$ is methyl, $R_3$ is hydrogen, n is 0, and $R_6$ corresponds in each case to one of the lines of Table A.

Table 15

Compounds of the general formula I.1, in which $R_1$ is 1,1,2,2-tetrafluoroethoxy, $R_2$ is methyl, $R_3$ is hydrogen, n is 0, and $R_6$ corresponds in each case to one of the lines of Table A.

Table 16

Compounds of the general formula I.1, in which $R_1$ and $R_3$ are fluorine, $R_2$ is hydrogen, n is 0, and $R_6$ corresponds in each case to one of the lines of Table A.

Table 17

Compounds of the general formula I.1, in which $R_1$ is chlorine, $R_2$ is hydrogen, $R_3$ is fluorine, n is 0, and $R_6$ corresponds in each case to one of the lines of Table A.

Table 18

Compounds of the general formula I.1, in which $R_1$ is bromine, $R_2$ is hydrogen, $R_3$ is fluorine, n is 0, and $R_6$ corresponds in each case to one of the lines of Table A.

Table 19

Compounds of the general formula I.1, in which $R_1$ is trifluoromethoxy, $R_2$ is hydrogen, $R_3$ is fluorine, n is 0, and $R_6$ corresponds in each case to one of the lines of Table A.

Table 20

Compounds of the general formula I.1, in which $R_1$ is chlorodifluoromethoxy, $R_2$ is hydrogen, $R_3$ is fluorine, n is 0, and $R_6$ corresponds in each case to one of the lines of Table A.

Table 21

Compounds of the general formula I.1, in which $R_1$ is 2,2,2-trifluoroethoxy, $R_2$ is hydrogen, $R_3$ is fluorine, n is 0, and $R_6$ corresponds in each case to one of the lines of Table A.

Table 22
Compounds of the general formula I.1, in which $R_1$ is 1,1,2,2-tetrafluoroethoxy, $R_2$ is hydrogen, $R_3$ is fluorine, n is 0, and $R_6$ corresponds in each case to one of the lines of Table A.

Table 23
Compounds of the general formula I.1, in which $R_1$ and $R_3$ are chlorine, $R_2$ is hydrogen, n is 0, and $R_6$ corresponds in each case to one of the lines of Table A.

Table 24
Compounds of the general formula I.1, in which $R_1$ is fluorine, $R_2$ is hydrogen, $R_3$ is chlorine, n is 0, and $R_6$ corresponds in each case to one of the lines of Table A.

Table 25
Compounds of the general formula I.1, in which $R_1$ is bromine, $R_2$ is hydrogen, $R_3$ is chlorine, n is 0, and $R_6$ corresponds in each case to one of the lines of Table A.

Table 26
Compounds of the general formula I.1, in which $R_1$ is trifluoromethoxy, $R_2$ is hydrogen, $R_3$ is chlorine, n is 0, and $R_6$ corresponds in each case to one of the lines of Table A.

Table 27
Compounds of the general formula I.1, in which $R_1$ is chlorodifluoromethoxy, $R_2$ is hydrogen, $R_3$ is chlorine, n is 0, and $R_6$ corresponds in each case to one of the lines of Table A.

Table 28
Compounds of the general formula I.1, in which $R_1$ is 2,2,2-trifluoroethoxy, $R_2$ is hydrogen, $R_3$ is chlorine, n is 0, and $R_6$ corresponds in each case to one of the lines of Table A.

Table 29
Compounds of the general formula I.1, in which $R_1$ is 1,1,2,2-tetrafluoroethoxy, $R_2$ is hydrogen, $R_3$ is chlorine, n is 0, and $R_6$ corresponds in each case to one of the lines of Table A.

Table 30
Compounds of the general formula I.1, in which $R_1$ is fluorine, $R_2$ and $R_3$ are hydrogen, n is 1, and $R_6$ corresponds in each case to one of the lines of Table A.

Table 31
Compounds of the general formula I.1, in which $R_1$ is chlorine, $R_2$ and $R_3$ are hydrogen, n is 1, and $R_6$ corresponds in each case to one of the lines of Table A.

Table 32
Compounds of the general formula I.1, in which $R_1$ is bromine, $R_2$ and $R_3$ are hydrogen, n is 1, and $R_6$ corresponds in each case to one of the lines of Table A.

Table 33
Compounds of the general formula I.1, in which $R_1$ is trifluoromethyl, $R_2$ and $R_3$ are hydrogen, n is 1, and $R_6$ corresponds in each case to one of the lines of Table A.

Table 34
Compounds of the general formula I.1, in which $R_1$ is trifluoromethoxy, $R_2$ and $R_3$ are hydrogen, n is 1, and $R_6$ corresponds in each case to one of the lines of Table A.

Table 35
Compounds of the general formula I.1, in which $R_1$ is chlorodifluoromethoxy, $R_2$ and $R_3$ are hydrogen, n is 1, and $R_6$ corresponds in each case to one of the lines of Table A.

Table 36
Compounds of the general formula I.1, in which $R_1$ is 2,2,2-trifluoroethoxy, $R_2$ and $R_3$ are hydrogen, n is 1, and $R_6$ corresponds in each case to one of the lines of Table A.

Table 37
Compounds of the general formula I.1, in which $R_1$ is 1,1,2,2-tetrafluoroethoxy, $R_2$ and $R_3$ are hydrogen, n is 1, and $R_6$ corresponds in each case to one of the lines of Table A.

Table 38
Compounds of the general formula I.1, in which $R_1$ is fluorine, $R_2$ is methyl, $R_3$ is hydrogen, n is 1, and $R_6$ corresponds in each case to one of the lines of Table A.

Table 39
Compounds of the general formula I.1, in which $R_1$ is chlorine, $R_2$ is methyl, $R_3$ is hydrogen, n is 1, and $R_6$ corresponds in each case to one of the lines of Table A.

Table 40
Compounds of the general formula I.1, in which $R_1$ is bromine, $R_2$ is methyl, $R_3$ is hydrogen, n is 1, and $R_6$ corresponds in each case to one of the lines of Table A.

Table 41
Compounds of the general formula I.1, in which $R_1$ is trifluoromethoxy, $R_2$ is methyl, $R_3$ is hydrogen, n is 1, and $R_6$ corresponds in each case to one of the lines of Table A.

Table 42
Compounds of the general formula I.1, in which $R_1$ is chlorodifluoromethoxy, $R_2$ is methyl, $R_3$ is hydrogen, n is 1, and $R_6$ corresponds in each case to one of the lines of Table A.

Table 43
Compounds of the general formula I.1, in which $R_1$ is 2,2,2-trifluoroethoxy, $R_2$ is methyl, $R_3$ is hydrogen, n is 1, and $R_6$ corresponds in each case to one of the lines of Table A.

Table 44
Compounds of the general formula I.1, in which $R_1$ is 1,1,2,2-tetrafluoroethoxy, $R_2$ is methyl, $R_3$ is hydrogen, n is 1, and $R_6$ corresponds in each case to one of the lines of Table A.

Table 45
Compounds of the general formula I.1, in which $R_1$ and $R_3$ are fluorine, $R_2$ is hydrogen, n is 1, and $R_6$ corresponds in each case to one of the lines of Table A.

Table 46
Compounds of the general formula I.1, in which $R_1$ is chlorine, $R_2$ is hydrogen, $R_3$ is fluorine, n is 1, and $R_6$ corresponds in each case to one of the lines of Table A.

Table 47
Compounds of the general formula I.1, in which $R_1$ is bromine, $R_2$ is hydrogen, $R_3$ is fluorine, n is 1, and $R_6$ corresponds in each case to one of the lines of Table A.

Table 48
Compounds of the general formula I.1, in which $R_1$ is trifluoromethoxy, $R_2$ is hydrogen, $R_3$ is fluorine, n is 1, and $R_6$ corresponds in each case to one of the lines of Table A.

Table 49

Compounds of the general formula I.1, in which $R_1$ is chlorodifluoromethoxy, $R_2$ is hydrogen, $R_3$ is fluorine, n is 1, and $R_6$ corresponds in each case to one of the lines of Table A.

Table 50

Compounds of the general formula I.1, in which $R_1$ is 2,2,2-trifluoroethoxy, $R_2$ is hydrogen, $R_3$ is fluorine, n is 1, and $R_6$ corresponds in each case to one of the lines of Table A.

Table 51

Compounds of the general formula I.1, in which $R_1$ is 1,1,2,2-tetrafluoroethoxy, $R_2$ is hydrogen, $R_3$ is fluorine, n is 1, and $R_6$ corresponds in each case to one of the lines of Table A.

Table 52

Compounds of the general formula I.1, in which $R_1$ and $R_3$ are chlorine, $R_2$ is hydrogen, n is 1, and $R_6$ corresponds in each case to one of the lines of Table A.

Table 53

Compounds of the general formula I.1, in which $R_1$ is fluorine, $R_2$ is hydrogen, $R_3$ is chlorine, n is 1, and $R_6$ corresponds in each case to one of the lines of Table A.

Table 54

Compounds of the general formula I.1, in which $R_1$ is bromine, $R_2$ is hydrogen, $R_3$ is chlorine, n is 1, and $R_6$ corresponds in each case to one of the lines of Table A.

Table 55

Compounds of the general formula I.1, in which $R_1$ is trifluoromethoxy, $R_2$ is hydrogen, $R_3$ is chlorine, n is 1, and $R_6$ corresponds in each case to one of the lines of Table A.

Table 56

Compounds of the general formula I.1, in which $R_1$ is chlorodifluoromethoxy, $R_2$ is hydrogen, $R_3$ is chlorine, n is 1, and $R_6$ corresponds in each case to one of the lines of Table A.

Table 57

Compounds of the general formula I.1, in which $R_1$ is 2,2,2-trifluoroethoxy, $R_2$ is hydrogen, $R_3$ is chlorine, n is 1, and $R_6$ corresponds in each case to one of the lines of Table A.

Table 58

Compounds of the general formula I.1, in which $R_1$ is 1,1,2,2-tetrafluoroethoxy, $R_2$ is hydrogen, $R_3$ is chlorine, n is 1, and $R_6$ corresponds in each case to one of the lines of Table A.

TABLE A

| No. | R6 |
|---|---|
| 1. | $NHNH_2$ |
| 2. | $NHNHCH_3$ |
| 3. | $NHNHCH_2CH_3$ |
| 4. | $NHNH(CH_2)_2CH_3$ |
| 5. | $NHNH(CH_2)_3CH_3$ |
| 6. | $NHNHCH(CH_3)_2$ |
| 7. | $NHNHC(CH_3)_3$ |
| 8. | $NHN(CH_3)_2$ |
| 9. | $NHN(CH_2CH_3)_2$ |
| 10. | $NHN[(CH_2)_2CH_3]_2$ |
| 11. | $NHN[(CH_2)_3CH_3]_2$ |
| 12. | $NHN[CH(CH_3)_2]_2$ |
| 13. | $NHN(CH_3)C(CH_3)_3$ |
| 14. | $NHN(CH_3)CH_2CH_3$ |
| 15. | $N(CH_3)NH_2$ |
| 16. | $N(CH_3)NHCH_3$ |
| 17. | $N(CH_3)NHCH_2CH_3$ |
| 18. | $N(CH_3)NH(CH_2)_2CH_3$ |
| 19. | $N(CH_3)NH(CH_2)_3CH_3$ |
| 20. | $N(CH_3)NHCH(CH_3)_2$ |
| 21. | $N(CH_3)NHC(CH_3)_3$ |
| 22. | $N(CH_3)N(CH_3)_2$ |
| 23. | $N(CH_3)N(CH_2CH_3)_2$ |
| 24. | $N(CH_3)N[(CH_2)_2CH_3]_2$ |
| 25. | $N(CH_3)N[(CH_2)_3CH_3]_2$ |
| 26. | $N(CH_3)N[CH(CH_3)_2]_2$ |
| 27. | $N(CH_3)N(CH_3)C(CH_3)_3$ |
| 28. | $N(CH_3)N(CH_3)CH_2CH_3$ |
| 29. | $N(CH_2CH_3)NH_2$ |
| 30. | $N(CH_2CH_3)NHCH_3$ |
| 31. | $N(CH_2CH_3)NHCH_2CH_3$ |
| 32. | $N(CH_2CH_3)NH(CH_2)_2CH_3$ |
| 33. | $N(CH_2CH_3)NH(CH_2)_3CH3$ |
| 34. | $N(CH_2CH_3)NHCH(CH_3)_2$ |
| 35. | $N(CH_2CH_3)NHC(CH_3)_3$ |
| 36. | $N(CH_2CH_3)N(CH_3)_2$ |
| 37. | $N(CH_2CH_3)N(CH_2CH_3)_2$ |
| 38. | $N(CH_2CH_3)N[(CH_2)_2CH_3]_2$ |
| 39. | $N(CH_2CH_3)N[(CH_2)_3CH_3]_2$ |
| 40. | $N(CH_2CH_3)N[CH(CH_3)_2]_2$ |
| 41. | $N(CH_2CH_3)N(CH_3)CH_2CH_3$ |
| 42. | $N(CH_2CF_3)NH_2$ |
| 43. | $N(CH_2CF_3)NHCH_3$ |
| 44. | $N(CH_2CF_3)NHCH_2CH_3$ |
| 45. | $N(CH_2CF_3)NH(CH_2)_2CH_3$ |
| 46. | $N(CH_2CF_3)NH(CH_2)_3CH_3$ |
| 47. | $N(CH_2CF_3)NHCH(CH_3)_2$ |
| 48. | $N(CH_2CF_3)NHC(CH_3)_3$ |
| 49. | $N(CH_2CF_3)N(CH_3)_2$ |
| 50. | $N(CH_2CF_3)N(CH_2CH_3)_2$ |
| 51. | $N(CH_2CF_3)N[(CH_2)_2CH_3]_2$ |
| 52. | $N(CH_2CF_3)N[(CH_2)_3CH_3]_2$ |
| 53. | $N(CH_2CF_3)N[CH(CH_3)_2]_2$ |
| 54. | $N(CH_2CF_3)N(CH_3)CH_2CH_3$ |
| 55. | $NHNHCH_2CF_3$ |
| 56. | $NHN(CH_3)CH_2CF_3$ |
| 57. | $NHN(CH_2CH_3)CH_2CF_3$ |
| 58. | $NHN(CH_2CF_3)_2$ |
| 59. | $N(CH_3)NHCH_2CF_3$ |
| 60. | $N(CH_3)N(CH_3)CH_2CF_3$ |
| 61. | $N(CH_3)N(CH_2CH_3)CH_2CF_3$ |
| 62. | $N(CH_3)N(CH_2CF_3)_2$ |
| 63. | $N(CH_2CH_3)NHCH_2CF_3$ |
| 64. | $N(CH_2CH_3)N(CH_3)CH_2CF_3$ |
| 65. | $N(CH_2CH_3)N(CH_2CH_3)CH_2CF_3$ |
| 66. | $N(CH_2CH_3)N(CH_2CF_3)_2$ |
| 67. | $N(CH_2CF_3)NHCH_2CF_3$ |
| 68. | $N(CH_2CF_3)N(CH_2CF_3)_2$ |
| 69. | $N(CH_2CH_2OH)NH_2$ |
| 70. | $N(CH_2CH_2OH)NHCH_3$ |
| 71. | $N(CH_2CH_2OH)NHCH_2CH_3$ |
| 72. | $N(CH_2CH_2OH)NH(CH_2)_2CH_3$ |
| 73. | $N(CH_2CH_2OH)NH(CH_2)_3CH_3$ |
| 74. | $N(CH_2CH_2OH)NHCH(CH_3)_2$ |
| 75. | $N(CH_2CH_2OH)NHC(CH_3)_3$ |
| 76. | $N(CH_2CH_2OH)N(CH_3)_2$ |
| 77. | $N(CH_2CH_2OH)N(CH_2CH_3)_2$ |
| 78. | $N(CH_2CH_2OH)N[(CH_2)_2CH_3]_2$ |
| 79. | $N(CH_2CH_2OH)N[(CH_2)_3CH_3]_2$ |
| 80. | $N(CH_2CH_2OH)N[CH(CH_3)_2]_2$ |
| 81. | $N(CH_2CH_2OH)N(CH_3)CH_2CH_3$ |
| 82. | $NHNHCH_2CH_2OH$ |
| 83. | $NHN(CH_3)CH_2CH_2OH$ |
| 84. | $NHN(CH_2CH_3)CH_2CH_2OH$ |
| 85. | $NHN(CH_2CH_2OH)_2$ |
| 86. | $N(CH_3)NHCH_2CH_2OH$ |
| 87. | $N(CH_3)N(CH_3)CH_2CH_2OH$ |
| 88. | $N(CH_3)N(CH_2CH_3)CH_2CH_2OH$ |
| 89. | $N(CH_3)N(CH_2CH_2OH)_2$ |
| 90. | $N(CH_2CH_3)NHCH_2CH_2OH$ |

TABLE A-continued

| No. | R6 |
|---|---|
| 91. | N(CH$_2$CH$_3$)N(CH$_3$)CH$_2$CH$_2$OH |
| 92. | N(CH$_2$CH$_3$)N(CH$_2$CH$_3$)CH$_2$CH$_2$OH |
| 93. | N(CH$_2$CH$_3$)N(CH$_2$CH$_2$CH)$_2$ |
| 94. | N(CH$_2$CH$_2$CH)NHCH$_2$CH$_2$CH |
| 95. | N(CH$_2$CH$_2$CH)N(CH$_2$CH$_2$CH)$_2$ |
| 96. | N(CH$_2$CH$_2$OCH$_3$)NH$_2$ |
| 97. | N(CH$_2$CH$_2$OCH$_3$)NHCH$_3$ |
| 98. | N(CH$_2$CH$_2$OCH$_3$)NHCH$_2$CH$_3$ |
| 99. | N(CH$_2$CH$_2$OCH$_3$)NH(CH$_2$)$_2$CH$_3$ |
| 100. | N(CH$_2$CH$_2$OCH$_3$)NH(CH$_2$)$_3$CH$_3$ |
| 101. | N(CH$_2$CH$_2$OCH$_3$)NHCH(CH$_3$)$_2$ |
| 102. | N(CH$_2$CH$_2$OCH$_3$)NHC(CH$_3$)$_3$ |
| 103. | N(CH$_2$CH$_2$OCH$_3$)N(CH$_3$)$_2$ |
| 104. | N(CH$_2$CH$_2$OCH$_3$)N(CH$_2$CH$_3$)$_2$ |
| 105. | N(CH$_2$CH$_2$OCH$_3$)N[(CH$_2$)$_2$CH$_3$]$_2$ |
| 106. | N(CH$_2$CH$_2$OCH$_3$)N[(CH$_2$)$_3$CH$_3$]$_2$ |
| 107. | N(CH$_2$CH$_2$OCH$_3$)N[CH(CH$_3$)$_2$]$_2$ |
| 108. | N(CH$_2$CH$_2$OCH$_3$)N(CH$_3$)CH$_2$CH$_3$ |
| 109. | NHNHCH$_2$CH$_2$OCH$_3$ |
| 110. | NHN(CH$_3$)CH$_2$CH$_2$OCH$_3$ |
| 111. | NHN(CH$_2$CH$_3$)CH$_2$CH$_2$OCH$_3$ |
| 112. | NHN(CH$_2$CH$_2$OCH$_3$)$_2$ |
| 113. | N(CH$_3$)NHCH$_2$CH$_2$OCH$_3$ |
| 114. | N(CH$_3$)N(CH$_3$)CH$_2$CH$_2$OCH$_3$ |
| 115. | N(CH$_3$)N(CH$_2$CH$_3$)CH$_2$CH$_2$OCH$_3$ |
| 116. | N(CH$_3$)N(CH$_2$CH$_2$OCH$_3$)$_2$ |
| 117. | N(CH$_2$CH$_3$)NHCH$_2$CH$_2$OCH$_3$ |
| 118. | N(CH$_2$CH$_3$)N(CH$_3$)CH$_2$CH$_2$OCH$_3$ |
| 119. | N(CH$_2$CH$_3$)N(CH$_2$CH$_3$)CH$_2$CH$_2$OCH$_3$ |
| 120. | N(CH$_2$CH$_3$)N(CH$_2$CH$_2$OCH$_3$)$_2$ |
| 121. | N(CH$_2$CH$_2$OCH$_3$)NH—CH$_2$CH$_2$OCH$_3$ |
| 122. | N(CH$_2$CH$_2$OCH$_3$)N—(CH$_2$CH$_2$OCH$_3$)$_2$ |
| 123. | NHNHCH$_2$CH |
| 124. | NHNHCH$_2$OCH$_3$ |
| 125. | NHNHCH$_2$OCH$_2$CH$_3$ |
| 126. | NHN(CH$_3$)CH$_2$OH |
| 127. | NHN(CH$_3$)CH$_2$OCH$_3$ |
| 128. | NHN(CH$_3$)CH$_2$OCH$_2$CH$_3$ |
| 129. | N(CH$_3$)NHCH$_2$OH |
| 130. | N(CH$_3$)NHCH$_2$OCH$_3$ |
| 131. | N(CH$_3$)NHCH$_2$OCH$_2$CH$_3$ |
| 132. | N(CH$_3$)N(CH$_3$)CH$_2$OH |
| 133. | N(CH$_3$)N(CH$_3$)CH$_2$OCH$_3$ |
| 134. | N(CH$_3$)N(CH$_3$)CH$_2$OCH$_2$CH$_3$ |
| 135. | N(CH$_2$CH)NHCH$_2$CH |
| 136. | N(CH$_2$OCH$_3$)NHCH$_2$OCH$_3$ |
| 137. | N(CH$_2$OCH$_3$)NH—CH$_2$OCH$_2$CH$_3$ |
| 138. | N(CH$_2$OCH$_3$)N(CH$_3$)CH$_2$OH |
| 139. | N(CH$_2$OCH$_3$)N(CH$_3$)CH$_2$OCH$_3$ |
| 140. | N(CH$_2$OCH$_2$CH$_3$)—N(CH$_3$)CH$_2$OCH$_3$CH$_3$ |
| 141. | NHNHCH(CH$_3$)CH$_2$OH |
| 142. | NHN(CH$_3$)CH(CH$_3$)CH$_2$OH |
| 143. | N(CH$_3$)NHCH(CH$_3$)CH$_2$OH |
| 144. | N(CH$_3$)N(CH$_3$)CH(CH$_3$)CH$_2$OH |
| 145. | NHNHCH(CH$_3$)CH$_2$OCH$_3$ |
| 146. | NHN(CH$_3$)CH(CH$_3$)CH$_2$OCH$_3$ |
| 147. | N(CH$_3$)NHCH(CH$_3$)CH$_2$OCH$_3$ |
| 148. | N(CH$_3$)N(CH$_3$)CH(CH$_3$)CH$_2$OCH$_3$ |
| 149. | NHNHCH(CH$_2$CH$_3$)CH$_2$OH |
| 150. | NHN(CH$_3$)CH(CH$_2$CH$_3$)CH$_2$OH |
| 151. | N(CH$_3$)NHCH(CH$_2$CH$_3$)CH$_2$OH |
| 152. | N(CH$_3$)N(CH$_3$)—CH(CH$_2$CH$_3$)CH$_2$OH |
| 153. | NHNHCH(CH$_2$CH$_3$)CH$_2$OCH$_3$ |
| 154. | NHN(CH$_3$)CH(CH$_2$CH$_3$)CH$_2$OCH$_3$ |
| 155. | N(CH$_3$)NHCH(CH$_2$CH$_3$)CH$_2$OCH$_3$ |
| 156. | N(CH$_3$)N(CH$_2$CH$_3$)—CH(CH$_2$CH$_3$)CH$_2$OCH$_3$ |
| 157. | NHN(CH$_2$CH$_3$)—CH(CH$_2$CH$_3$)CH$_2$OH |
| 158. | N(CH$_3$)N(CH$_2$CH$_3$)—CH(CH$_2$CH$_3$)CH$_2$OH |
| 159. | NHN(CH$_2$CH$_3$)—CH(CH$_2$CH$_3$)CH$_2$OCH$_3$ |
| 160. | N(CH$_3$)N(CH$_2$CH$_3$)—CH(CH$_2$CH$_3$)CH$_2$OCH$_3$ |
| 161. | NHNHCHO |
| 162. | NHNHC(O)CH$_3$ |
| 163. | NHNHC(O)CH$_2$CH$_3$ |
| 164. | NHNHC(O)CH$_2$CH$_2$OCH$_3$ |
| 165. | NHNHC(O)CF$_3$ |
| 166. | NHNHC(O)CF$_2$CF$_3$ |
| 167. | NHNHC(O)(CF$_2$)$_2$CF$_3$ |
| 168. | N(CHO)NH$_2$ |
| 169. | N[C(O)CH$_3$]NH$_2$ |
| 170. | N[C(O)CH$_2$CH$_3$]NH$_2$ |
| 171. | N[C(O)CH$_2$CH$_2$OCH$_3$]NH$_2$ |
| 172. | N[C(O)CF$_3$]NH$_2$ |
| 173. | N[C(O)CF$_2$CF$_3$]NH$_2$ |
| 174. | N[C(O)(CF$_2$)$_2$CF$_3$]NH$_2$ |
| 175. | N(CHO)NH(CHO) |
| 176. | N[C(O)CH$_3$]NH[C(O)CH$_3$] |
| 177. | N[C(O)CH$_2$CH$_3$]NH[C(O)CH$_2$CH$_3$] |
| 178. | N[C(O)CH$_2$CH$_2$OCH$_3$]NH—[C(O)CH$_2$CH$_2$OCH$_3$] |
| 179. | N[C(O)CF$_3$]NH[C(O)CF$_3$] |
| 180. | N[C(O)CF$_2$CF$_3$]NH[C(O)CF$_2$CF$_3$] |
| 181. | N[C(O)(CF$_2$)$_2$CF$_3$]NH—[C(O)(CF$_2$)$_2$CF$_3$] |
| 182. | NHN(CHO)$_2$ |
| 183. | NHN[C(O)CH$_3$]$_2$ |
| 184. | NHN[C(O)CH$_2$CH$_3$]$_2$ |
| 185. | NHN[C(O)CH$_2$CH$_2$OCH$_3$]$_2$ |
| 186. | NHN[C(O)CF$_3$]$_2$ |
| 187. | NHN[C(O)CF$_2$CF$_3$]$_2$ |
| 188. | NHN[C(O)(CF$_2$)$_2$CF$_3$]$_2$ |
| 189. | N(CH$_3$)NHCHO |
| 190. | N(CH$_3$)NHC(O)CH$_3$ |
| 191. | N(CH$_3$)NHC(O)CH$_2$CH$_3$ |
| 192. | N(CH$_3$)NHC(O)CH$_2$CH$_2$OCH$_3$ |
| 193. | N(CH$_3$)NHC(O)CF$_3$ |
| 194. | N(CH$_3$)NHC(O)CF$_2$CF$_3$ |
| 195. | N(CH$_3$)NHC(O)(CF$_2$)$_2$CF$_3$ |
| 196. | N(CHO)NH(CH$_3$) |
| 197. | N[C(O)CH$_3$]NH(CH$_3$) |
| 198. | N[C(O)CH$_2$CH$_3$]NH(CH$_3$) |
| 199. | N[C(O)CH$_2$CH$_2$OCH$_3$]NH(CH$_3$) |
| 200. | N[C(O)CF$_3$]NH(CH$_3$) |
| 201. | N[C(O)CF$_2$CF$_3$]NH(CH$_3$) |
| 202. | N[C(O)(CF$_2$)$_2$CF$_3$]NH(CH$_3$) |
| 203. | N(CHO)N(CH$_3$)(CHO) |
| 204. | N[C(O)CH$_3$]N(CH$_3$)[C(O)CH$_3$] |
| 205. | N[C(O)CH$_2$CH$_3$]—N(CH$_3$)[C(O)CH$_2$CH$_3$] |
| 206. | N[C(O)CH$_2$CH$_2$OCH$_3$]N(CH$_3$)—[C(O)CH$_2$CH$_2$OCH$_3$] |
| 207. | N[C(O)CF$_3$]N(CH$_3$)[C(O)CF$_3$] |
| 208. | N[C(O)CF$_2$CF$_3$]—N(CH$_3$)[C(O)CF$_2$CF$_3$] |
| 209. | N[O(O)(CF$_2$)$_2$CF$_3$]N(CH$_3$)—[C(O)(CF$_2$)$_2$CF$_3$] |
| 210. | N(CH$_3$)N(CHO)$_2$ |
| 211. | N(CH$_3$)N[C(O)CH$_3$]$_2$ |
| 212. | N(CH$_3$)N[O(O)CH$_2$CH$_3$]$_2$ |
| 213. | N(CH$_3$)N[C(O)CH$_2$CH$_2$OCH$_3$]$_2$ |
| 214. | N(CH$_3$)N[C(O)CF$_3$]$_2$ |
| 215. | N(CH$_3$)N[C(O)CF$_2$CF$_3$]$_2$ |
| 216. | N(CH$_3$)N[C(O)(CF$_2$)$_2$CF$_3$]$_2$ |
| 217. | N(CH$_3$)N(CH$_3$)CHO |
| 218. | N(CH$_3$)N(CH$_3$)C(O)CH$_3$ |
| 219. | N(CH$_3$)N(CH$_3$)C(O)CH$_2$CH$_3$ |
| 220. | N(CH$_3$)N(CH$_3$)C(O)CH$_2$CH$_2$OCH$_3$ |
| 221. | N(CH$_3$)N(CH$_3$)C(O)CF$_3$ |
| 222. | N(CH$_3$)N(CH$_3$)C(O)CF$_2$CF$_3$ |
| 223. | N(CH$_3$)N(CH$_3$)C(O)(CF$_2$)$_2$CF$_3$ |
| 224. | N(CHO)N(CH$_3$)$_2$ |
| 225. | N[C(O)CH$_3$]N(CH$_3$)$_2$ |
| 226. | N[C(O)CH$_2$CH$_3$]N(CH$_3$)$_2$ |
| 227. | N[C(O)CH$_2$CH$_2$OCH$_3$]N(CH$_3$)$_2$ |
| 228. | N[C(O)CF$_3$]N(CH$_3$)$_2$ |
| 229. | N[C(O)CF$_2$CF$_3$]N(CH$_3$)$_2$ |
| 230. | N[C(O)(CF$_2$)$_2$CF$_3$]N(CH$_3$)$_2$ |
| 231. | NH–cyclohexyl |
| 232. | 1-NH, 2-NH$_2$ cyclohexyl |

TABLE A-continued

| No. | R6 |
|---|---|
| 233. | (4-aminocyclohexyl)amino (NH-cyclohexyl-NH2) |
| 234. | piperazin-1-yl (NH) |
| 235. | 4-(2-aminoethyl)piperazin-1-yl |
| 236. | 4-(3-aminopropyl)piperazin-1-yl |
| 237. | morpholin-4-yl |
| 238. | 2,6-dimethylmorpholin-4-yl |
| 239. | 3-methylmorpholin-4-yl |
| 240. | 3,5-dimethylmorpholin-4-yl |
| 241. | $NH_2$ |
| 242. | $NH(CH_3)$ |
| 243. | $NH(CH_2CH_3)$ |
| 244. | $NH[(CH_2)_2CH_3]$ |
| 245. | $NH[(CH_2)_3CH_3]$ |
| 246. | $NH[(CH_2)_4CH_3]$ |
| 247. | $NH[CH(CH_3)_2]$ |
| 248. | $NH[CH(CH_2CH_3)_2]$ |
| 249. | $NH[C(CH_3)_3]$ |
| 250. | $NH[CH(CH_3)CH_2CH_3]$ |
| 251. | $NH[CH_2CH(CH_3)_2]$ |
| 252. | $N(CH_3)_2$ |
| 253. | $NCH_3(CH_2CH_3)$ |
| 254. | $NCH_3[(CH_2)_2CH_3]$ |
| 255. | $NCH_3[(CH_2)_3CH_3]$ |
| 256. | $NCH_3[(CH_2)_4CH_3]$ |
| 257. | $NCH_3[CH(CH_3)_2]$ |
| 258. | $NCH_3[CH(CH_2CH_3)_2]$ |
| 259. | $NCH_3[C(CH_3)_3]$ |
| 260. | $NCH_3[CH(CH_3)CH_2CH_3]$ |
| 261. | $NCH_3[CH_2CH(CH_3)_2]$ |
| 262. | $NCH_3(CH_2CH_3)$ |
| 263. | $N(CH_2CH_3)_2$ |
| 264. | $NCH_2CH_3[(CH_2)_2CH_3]$ |
| 265. | $NCH_2CH_3[(CH_2)_3CH_3]$ |
| 266. | $NCH_2CH_3[(CH_2)_4CH_3]$ |
| 267. | $NCH_2CH_3[CH(CH_3)_2]$ |
| 268. | $NCH_2CH_3[CH(CH_2CH_3)_2]$ |
| 269. | $NCH_2CH_3[C(CH_3)_3]$ |
| 270. | $NCH_2CH_3[CH(CH_3)CH_2CH_3]$ |
| 271. | $NCH_2CH_3[CH_2CH(CH_3)_2]$ |
| 272. | $NH(CH_2CH_2NH_2)$ |
| 273. | $NH[(CH_2)_3NH_2]$ |
| 274. | $NH[CH(CH_3)CH_2NH_2]$ |
| 275. | $NH[CH(CH_3)CH_2CH_2NH_2]$ |
| 276. | $NH[CH(CH_2CH_3)CH_2NH_2]$ |
| 277. | $NH[CH(i\text{-propyl})CH_2NH_2]$ |
| 278. | $NH(CH_2CH_2NHCH_3)$ |
| 279. | $NH[(CH_2)_3NHCH_3]$ |
| 280. | $NH[CH(CH_3)CH_2CH_2NHCH_3]$ |
| 281. | $NH[CH(CH_3)CH_2NHCH_3]$ |
| 282. | $NH[CH(CH_2CH_3)CH_2NHCH_3]$ |
| 283. | $NH[CH(i\text{-propyl})CH_2NHCH_3]$ |
| 284. | $NH(CH_2CH_2N(CH_3)_2)$ |
| 285. | $NH[(CH_2)_3N(CH_3)_2]$ |
| 286. | $NH[CH(CH_3)CH_2CH_2N(CH_3)_2]$ |
| 287. | $NH[CH(CH_3)CH_2N(CH_3)_2]$ |
| 288. | $NH[CH(CH_2CH_3)CH_2N(CH_3)_2]$ |
| 289. | $NH[CH(i\text{-propyl})CH_2N(CH_3)_2]$ |
| 290. | $NCH_3(CH_2CH_2NH_2)$ |
| 291. | $NCH_3[(CH_2)_3NH_2]$ |
| 292. | $NCH_3[CH(CH_3)CH_2NH_2]$ |
| 293. | $NCH_3[CH(CH_3)CH_2CH_2NH_2]$ |
| 294. | $NCH_3[CH(CH_2CH_3)CH_2NH_2]$ |
| 295. | $NCH_3[CH(i\text{-propyl})CH_2NH_2]$ |
| 296. | $NCH_3(CH_2CH_2NHCH_3)$ |
| 297. | $NCH_3[(CH_2)_3NHCH_3]$ |
| 298. | $NCH_3[CH(CH_3)CH_2NHCH_3]$ |
| 299. | $NCH_3[CH(CH_3)CH_2CH_2NHCH_3]$ |
| 300. | $NCH_3[CH(CH_2CH_3)CH_2NHCH_3]$ |
| 301. | $NCH_3[CH(i\text{-propyl})CH_2NHCH_3]$ |
| 302. | $NCH_3(CH_2CH_2N(CH_3)_2)$ |
| 303. | $NCH_3[(CH_2)_3N(CH_3)_2]$ |
| 304. | $NCH_3[CH(CH_3)CH_2N(CH_3)_2]$ |
| 305. | $NCH_3[CH(CH_3)CH_2CH_2N(CH_3)_2]$ |
| 306. | $NCH_3[CH(CH_2CH_3)CH_2N(CH_3)_2]$ |
| 307. | $NCH_3[CH(i\text{-propyl})CH_2N(CH_3)_2]$ |
| 308. | $NH[CH_2CH_2OCH_2OCH_3]$ |
| 309. | $NH[CH(CH_3)CH_2OCH_2OCH_3]$ |
| 310. | $NH[CH_2CH_2OCH_2OCH_2CH_3]$ |
| 311. | $NH[CH(CH_3)CH_2OCH_2OCH_2CH_3]$ |
| 312. | $NH[CH(CH_3)CH_2O-CH_2OCH_3]$ |
| 313. | $NH[CH(CH_2CH_3)CH_2O-CH_2OCH_2CH_3]$ |
| 314. | $NCH_3[CH_2CH_2OCH_2OCH_3]$ |
| 315. | $NCH_3[CH(CH_3)CH_2OCH_2OCH_3]$ |
| 316. | $NCH_3[CH_2CH_2OCH_2OCH_2CH_3]$ |
| 317. | $NCH_3[CH(CH_3)CH_2O-CH_2OCH_2CH_3]$ |
| 318. | $NCH_3[CH(CH_2CH_3)CH_2O-CH_2OCH_3]$ |
| 319. | $NCH_3[CH(CH_2CH_3)CH_2O-CH_2OCH_2CH_3]$ |
| 320. | $NCH_2OCH_3[CH_2CH_2OCH_2OCH_3]$ |
| 321. | $NCH_2OCH_3[CH(CH_3)CH_2O-CH_2OCH_3]$ |
| 322. | $NCH_2OCH_3[CH_2CH_2O-CH_2OCH_2CH_3]$ |
| 323. | $NCH_2OCH_3[CH(CH_3)CH_2O-CH_2OCH_2CH_3]$ |
| 324. | $NCH_2OCH_3[CH(CH_2CH_3)CH_2O-CH_2OCH_3]$ |
| 325. | $NCH_2OCH_3[CH(CH_2CH_3)CH_2O-CH_2OCH_2CH_3]$ |
| 326. | $NHCH_2CH_2NHCH_2CH_2OH$ |
| 327. | $NHCH(CH_3)CH_2NHCH_2CH_2OH$ |
| 328. | $NHCH(CH_2CH_3)CH_2NH-CH_2CH_2OH$ |
| 329. | $NHCH(CH_3)_2CH_2NH-CH_2CH_2OH$ |
| 330. | $NHCH_2CH_2NH(CH_2)_3OH$ |
| 331. | $NHCH(CH_3)CH_2NH(CH_2)_3OH$ |
| 332. | $NHCH(CH_2CH_3)CH_2NH-(CH_2)_3OH$ |
| 333. | $NHCH(CH_3)_2CH_2NH-(CH_2)_3OH$ |
| 334. | $NHCH_2CH_2NHCH(CH_3)CH_2OH$ |
| 335. | $NHCH(CH_3)CH_2NH-CH(CH_3)CH_2OH$ |
| 336. | $NHCH(CH_2CH_3)CH_2NH-CH(CH_3)CH_2OH$ |
| 337. | $NHCH(CH_3)_2CH_2NH-CH(CH_3)CH_2OH$ |
| 338. | $NHCH_2CH_2NHCH_2CH(CH_3)OH$ |
| 339. | $NHCH(CH_3)CH_2NH-CH_2CH(CH_3)OH$ |
| 340. | $NHCH(CH_2CH_3)CH_2NH-CH_2CH(CH_3)OH$ |
| 341. | $NHCH(CH(CH_3)_2)CH_2NH-CH_2CH(CH_3)OH$ |
| 342. | $NHCH_2CN$ |

TABLE A-continued

| No. | R6 |
|---|---|
| 343. | NH(CH$_2$)$_2$CN |
| 344. | NH(CH$_2$)$_3$CN |
| 345. | NH(CH$_2$)$_4$CN |
| 346. | NHCH(CH$_3$)CN |
| 347. | NHCH(CH$_3$)CH$_2$CN |
| 348. | NHCH(CH$_2$CH$_3$)CN |
| 349. | NHCH(CH$_2$CH$_3$)CH$_2$CN |
| 350. | NHCH(CH(CH$_3$)$_2$)CN |
| 351. | NHCH(CH(CH$_3$)$_2$)CH$_2$CN |
| 352. | N(CH$_3$)CH$_2$CN |
| 353. | N(CH$_3$)(CH$_2$)$_2$CN |
| 354. | N(CH$_3$)(CH$_2$)$_3$CN |
| 355. | N(CH$_3$)(CH$_2$)$_4$CN |
| 356. | N(CH$_3$)CH(CH$_3$)CN |
| 357. | N(CH$_3$)CH(CH$_3$)CH$_2$CN |
| 358. | N(CH$_3$)CH(CH$_2$CH$_3$)CN |
| 359. | N(CH$_3$)CH(CH$_2$CH$_3$)CHCN |
| 360. | N(CH$_3$)CH(CH(CH$_3$)$_2$)CN |
| 361. | N(CH$_3$)CH(CH(CH$_3$)$_2$)CH$_2$CN |
| 362. | N(CH$_2$CN)$_2$ |
| 363. | N(CH$_2$CH$_2$CN)$_2$ |
| 364. | NHCH$_2$F |
| 365. | NHCH$_2$CH$_2$F |
| 366. | NHCH$_2$CF$_3$ |
| 367. | NHCH$_2$CF$_2$CF$_3$ |
| 368. | N(CH$_3$)CH$_2$F |
| 369. | N(CH$_3$)CH$_2$CH$_2$F |
| 370. | N(CH$_3$)CH$_2$CF$_3$ |
| 371. | N(CH$_3$)CH$_2$CF$_2$CF$_3$ |
| 372. | N(CHO)CH$_2$F |
| 373. | N(CHO)CH$_2$CH$_2$F |
| 374. | N(CHO)CH$_2$CF$_3$ |
| 375. | N(CHO)CH$_2$CF$_2$CF$_3$ |
| 376. | N(COCH$_3$)CH$_2$F |
| 377. | N(COCH$_3$)CH$_2$CH$_2$F |
| 378. | N(COCH$_3$)CH$_2$CF$_3$ |
| 379. | N(COCH$_3$)CH$_2$CF$_2$CF$_3$ |
| 380. | N(CH$_2$F)$_2$ |
| 381. | N(CH$_2$CH$_2$F)$_2$ |
| 382. | N(CH$_2$CF$_3$)$_2$ |
| 383. | N(CH$_2$CF$_2$CF$_3$)$_2$ |
| 384. | NH(CH$_2$CH=CH$_2$) |
| 385. | NH(CH$_2$CH=CHCH$_3$) |
| 386. | NH(CH$_2$CH=C(CH$_3$)$_2$) |
| 387. | NH(CH(CH$_3$)CH=CH$_2$) |
| 388. | NH(CH(CH$_3$)CH=CHCH$_3$) |
| 389. | NH(CH(CH$_3$)CH=C(CH$_3$)$_2$) |
| 390. | NH(CH(CH$_2$CH$_3$)CH=CH$_2$) |
| 391. | NH(CH(CH$_2$CH$_3$)CH=CHCH$_3$) |
| 392. | NH(CH(CH$_2$CH$_3$)CH=C(CH$_3$)$_2$) |
| 393. | NH(CH[CH(CH$_3$)$_2$]CH=CH$_2$) |
| 394. | NH(CH[CH(CH$_3$)$_2$]CH=CHCH$_3$) |
| 395. | NH(CH[CH(CH$_3$)$_2$]CH=C(CH$_3$)$_2$) |
| 396. | N(CH$_3$)(CH$_2$CH=CH$_2$) |
| 397. | N(CH$_3$)(CH$_2$CH=CHCH$_3$) |
| 398. | N(CH$_3$)(CH$_2$CH=C(CH$_3$)$_2$) |
| 399. | N(CH$_3$)(CH(CH$_3$)CH=CH$_2$) |
| 400. | N(CH$_3$)(CH(CH$_3$)CH=CHCH$_3$) |
| 401. | N(CH$_3$)(CH(CH$_3$)CH=C(CH$_3$)$_2$) |
| 402. | N(CH$_3$)(CH(CH$_2$CH$_3$)CH=CH$_2$) |
| 403. | N(CH$_3$)(CH(CH$_2$CH$_3$)CH=CHCH$_3$) |
| 404. | N(CH$_3$)—(CH(CH$_2$CH$_3$)CH=C(CH$_3$)$_2$) |
| 405. | N(CH$_3$)(CH[CH(CH$_3$)$_2$]CH=CH$_2$) |
| 406. | N(CH$_3$)(CH[CH(CH$_3$)$_2$]CH=CHCH$_3$) |
| 407. | N(CH$_3$)—(CH[CH(CH$_3$)$_2$]CH=C(CH$_3$)$_2$) |
| 408. | NH(CH$_2$C≡CH) |
| 409. | NH(CH$_2$C≡CCH$_3$) |
| 410. | NH(CH(CH$_3$)C≡CH) |
| 411. | NH(CH(CH$_3$)C≡CCH$_3$) |
| 412. | NH(CH(CH$_2$CH$_3$)C≡CH) |
| 413. | NH(CH(CH$_2$CH$_3$)C≡CCH$_3$) |
| 414. | NH(CH[CH(CH$_3$)$_2$]C≡CH) |
| 415. | NH(CH[CH(CH$_3$)$_2$]C≡CCH$_3$) |
| 416. | N(CH$_3$)(CH$_2$C≡CH) |
| 417. | N(CH$_3$)(CH$_2$C≡CCH$_3$) |
| 418. | N(CH$_3$)(CH(CH$_3$)C≡CH) |
| 419. | N(CH$_3$)(CH(CH$_3$)C≡CCH$_3$) |
| 420. | N(CH$_3$)(CH(CH$_2$CH$_3$)C≡CH) |
| 421. | N(CH$_3$)(CH(CH$_2$CH$_3$)C≡CCH$_3$) |
| 422. | N(CH$_3$)(CH[CH(CH$_3$)$_2$]C≡CH) |
| 423. | N(CH$_3$)(CH[CH(CH$_3$)$_2$]C≡CCH$_3$) |
| 424. | N(CH$_3$)—(CH[CH(CH$_3$)$_2$]C≡C(CH$_3$)$_2$) |
| 425. | NHCH$_2$CH$_2$NHC(O)H |
| 426. | NHCH$_2$CH$_2$NHC(O)CH$_3$ |
| 427. | NHCH$_2$CH$_2$NH—C(O)CH$_2$CH$_3$ |
| 428. | NHCH$_2$CH$_2$NH—C(O)CF$_3$ |
| 429. | NHCH$_2$CH$_2$NH—C(O)(CH$_2$)$_2$CH$_3$ |
| 430. | NHCH$_2$CH$_2$NH—C(O)CH$_2$OH |
| 431. | NHCH$_2$CH$_2$NH—C(O)CH$_2$OCH$_3$ |
| 432. | NHCH$_2$CH$_2$NH—C(O)CH(CH$_3$)OH |
| 433. | NHCH$_2$CH$_2$NH—C(O)CH(CH$_3$)OCH$_3$ |
| 434. | NHCH$_2$CH$_2$NH—C(O)CH$_2$CH(CH$_3$)OH |
| 435. | NHCH$_2$CH$_2$NH—C(O)CH$_2$CH(CH$_3$)OCH$_3$ |
| 436. | NNCH$_2$CH$_2$NH—C(O)CH(CH$_3$)CH$_2$OH |
| 437. | NHCH$_2$CH$_2$NH C(O)CH(CH$_3$)CH$_2$OCH$_3$ |
| 438. | NHCH$_2$CH$_2$CH$_2$NHC(O)H |
| 439. | NHCH$_2$CH$_2$CH$_2$NH—C(O)CH$_3$ |
| 440. | NHCH$_2$CH$_2$CH$_2$NH—C(O)CH$_2$CH$_3$ |
| 441. | NHCH$_2$CH$_2$CH$_2$NH—C(O)CF$_3$ |
| 442. | NHCH$_2$CH$_2$CH$_2$NH—C(O)(CH$_2$)$_2$CH$_3$ |
| 443. | NHCH$_2$CH$_2$CH$_2$NH—C(O)CH$_2$OH |
| 444. | NHCH$_2$CH$_2$CH$_2$NH—C(O)CH$_2$OCH$_3$ |
| 445. | NHCH$_2$CH$_2$CH$_2$NH—C(O)CH(CH$_3$)OH |
| 446. | NHCH$_2$CH$_2$CH$_2$NH—C(O)CH(CH$_3$)OCH$_3$ |
| 447. | NHCH$_2$CH$_2$CH$_2$NH—C(O)CH$_2$CH(CH$_3$)OH |
| 448. | NHCH$_2$CH$_2$CH$_2$NH—C(O)CH$_2$CH(CH$_3$)OCH$_3$ |
| 449. | NHCH$_2$CH$_2$CH$_2$NH—C(O)CH(CH$_3$)CH$_2$OH |
| 450. | NHCH$_2$CH$_2$CH$_2$NH—C(O)CH(CH$_3$)CH$_2$OCH$_3$ |
| 451. | NHCH(CH$_3$)CH$_2$NHC(O)H |
| 452. | NHCH(CH$_3$)CH$_2$NH—C(O)CH$_3$ |
| 453. | NHCH(CH$_3$)CH$_2$NH—C(O)CH$_2$CH$_3$ |
| 454. | NHCH(CH$_3$)CH$_2$NH—C(O)CF$_3$ |
| 455. | NHCH(CH$_3$)CH$_2$NH—C(O)(CH$_2$)$_2$CH$_3$ |
| 456. | NHCH(CH$_3$)CH$_2$NH—C(O)CH$_2$OH |
| 457. | NHCH(CH$_3$)CH$_2$NH—C(O)CH$_2$OCH$_3$ |
| 458. | NHCH(CH$_3$)CH$_2$NH—C(O)CH(CH$_3$)OH |
| 459. | NHCH(CH$_3$)CH$_2$NH—C(O)CH(CH$_3$)OCH$_3$ |
| 460. | NHCH(CH$_3$)CH$_2$NH—C(O)CH$_2$CH(CH$_3$)OH |
| 461. | NHCH(CH$_3$)CH$_2$NH—C(O)CH$_2$CH(CH$_3$)OCH$_3$ |
| 462. | NHCH(CH$_3$)CH$_2$NH—C(O)CH(CH$_3$)CH$_2$OH |
| 463. | NHCH(CH$_3$)CH$_2$NH—C(O)CH(CH$_3$)CH$_2$OCH$_3$ |
| 464. | NHCH(CH$_3$)CH$_2$CH$_2$NH—C(O)H |
| 465. | NHCH(CH$_3$)CH$_2$CH$_2$NH—C(O)CH$_3$ |
| 466. | NHCH(CH$_3$)CH$_2$CH$_2$NH—C(O)CH$_2$CH$_3$ |
| 467. | NHCH(CH$_3$)CH$_2$CH$_2$NH—C(O)CF$_3$ |
| 468. | NHCH(CH$_3$)CH$_2$CH$_2$NH—C(O)(CH$_2$)$_2$CH$_3$ |
| 469. | NHCH(CH$_3$)CH$_2$CH$_2$NH—C(O)CH$_2$OH |
| 470. | NHCH(CH$_3$)CH$_2$CH$_2$NH—C(O)CH$_2$OCH$_3$ |
| 471. | NHCH(CH$_3$)CH$_2$CH$_2$NH—C(O)CH(CH$_3$)OH |
| 472. | NHCH(CH$_3$)CH$_2$CH$_2$NH—C(O)CH(CH$_3$)OCH$_3$ |
| 473. | NHCH(CH$_3$)CH$_2$CH$_2$NH—C(O)CH$_2$CH(CH$_3$)OH |
| 474. | NHCH(CH$_3$)CH$_2$CH$_2$NH—C(O)CH$_2$CH(CH$_3$)OCH$_3$ |
| 475. | NHCH(CH$_3$)CH$_2$CH$_2$NH—C(O)CH(CH$_3$)CH$_2$OH |
| 476. | NHCH(CH$_3$)CH$_2$CH$_2$NH—C(O)CH(CH$_3$)CH$_2$OCH$_3$ |
| 477. | NHCH(CH$_2$CH$_3$)CH$_2$NHC(O)H |
| 478. | NHCH(CH$_2$CH$_3$)CH$_2$NH—C(O)CH$_3$ |
| 479. | NHCH(CH$_2$CH$_3$)CH$_2$NH—C(O)CH$_2$CH$_3$ |
| 480. | NHCH(CH$_2$CH$_3$)CH$_2$NH—C(O)CF$_3$ |
| 481. | NHCH(CH$_2$CH$_3$)CH$_2$NH—C(O)(CH$_2$)$_2$CH$_3$ |
| 482. | NHCH(CH$_2$CH$_3$)CH$_2$NH—C(O)CH$_2$OH |
| 483. | NHCH(CH$_2$CH$_3$)CH$_2$NH—C(O)CH$_2$OCH$_3$ |
| 484. | NHCH(CH$_2$CH$_3$)CH$_2$NH—C(O)CH(CH$_3$)OH |
| 485. | NHCH(CH$_2$CH$_3$)CH$_2$NH—C(O)CH(CH$_3$)OCH$_3$ |
| 486. | NHCH(CH$_2$CH$_3$)CH$_2$NH—C(O)CH$_2$CH(CH$_3$)OH |

TABLE A-continued

| No. | R6 |
|---|---|
| 487. | NHCH(CH₂CH₃)CH₂NH—C(O)CH₂CH(CH₃)OCH₃ |
| 488. | NHCH(CH₂CH₃)CH₂NH—C(O)CH(CH₃)CH₂OH |
| 489. | NHCH(CH₂CH₃)CH₂NH—C(O)CH(CH₃)CH₂OCH₃ |
| 490. | NHCH(CH₂CH₃)CH₂CH₂NH—C(O)H |
| 491. | NHCH(CH₂CH₃)CH₂CH₂NH—C(O)CH₃ |
| 492. | NHCH(CH₂CH₃)CH₂CH₂NH—C(O)CH₂CH₃ |
| 493. | NHCH(CH₂CH₃)CH₂CH₂NH—C(O)CF₃ |
| 494. | NHCH(CH₂CH₃)CH₂CH₂NH—C(O)(CH₂)₂CH₃ |
| 495. | NHCH(CH₂CH₃)CH₂CH₂NH—C(O)CH₂OH |
| 496. | NHCH(CH₂CH₃)CH₂CH₂NH—C(O)CH₂OCH₃ |
| 497. | NHCH(CH₂CH₃)CH₂CH₂NH—C(O)CH(CH₃)OH |
| 498. | NHCH(CH₂CH₃)CH₂CH₂NI-I—C(O)CH(CH₃)OCH₃ |
| 499. | NHCH(CH₂CH₃)CH₂CH₂NH—C(O)CH₂CH(CH₃)OH |
| 500. | NHCH(CH₂CH₃)CH₂CH₂NH—C(O)CH₂CH(CH₃)OCH₃ |
| 501. | NHCH(CH₂CH₃)CH₂CH₂NH—C(O)CH(CH₃)CH₂OH |
| 502. | NHCH(CH₂CH₃)CH₂CH₂NH—C(O)CH(CH₃)CH₂OCH₃ |
| 503. | NHCH(CH₂CH₂CH₃)CH₂NHC(O)H |
| 504. | NHCH(CH₂CH₂CH₃)CH₂NH—C(O)CH₃ |
| 505. | NHCH(CH₂CH₂CH₃)CH₂NH—C(O)CH₂CH₃ |
| 506. | NHCH(CH₂CH₂CH₃)CH₂NH—C(O)CF₃ |
| 507. | NHCH(CH₂CH₂CH3)CH₂NH—C(O)(CH₂)₂CH₃ |
| 508. | NHCH(CH₂CH₂CH₃)CH₂NH—C(O)CH₂OH |
| 509. | NHCH(CH₂CH₂CH₃)CH₂NH—C(O)CH₂OCH₃ |
| 510. | NHCH(CH₂CH₂CH₃)CH₂NH—C(O)CH(CH₃)OH |
| 511. | NHCH(CH₂CH₂CH₃)CH₂NH—C(O)CH(CH₃)OCH₃ |
| 512. | NHCH(CH₂CH₂CH₃)CH₂NH—C(O)CH₂CH(CH₃)OH |
| 513. | NHCH(CH₂CH₂CH₃)CH₂NH—C(O)CH₂CH(CH₃)OCH₃ |
| 514. | NHCH(CH₂CH₂CH₃)CH₂NH—C(O)CH(CH₃)CH₂OH |
| 515. | NHCH(CH₂CH₂CH₃)CH₂NH—C(O)CH(CH₃)CH₂OCH₃ |
| 516. | NHCH(CH₂CH₂CH₃)CH₂CH₂NH—C(O)H |
| 517. | NHCH(CH₂CH₂CH₃)CH₂CH₂NH—C(O)CH₃ |
| 518. | NHCH(CH₂CH₂CH₃)CH₂CH₂NH—C(O)CH₂CH₃ |
| 519. | NHCH(CH₂CH₂CH₃)CH₂CH₂NH—C(O)CF₃ |
| 520. | NHCH(CH₂CH₂CH₃)CH₂CH₂NH—C(O)(CH₂)₂CH₃ |
| 521. | NHCH(CH₂CH₂CH₃)CH₂CH₂NH—C(O)CH₂OH |
| 522. | NHCH(CH₂CH₂CH₃)CH₂CH₂NH—C(O)CH₂OCH₃ |
| 523. | NHCH(CH₂CH₂CH₃)CH₂CH₂NH—C(O)CH(CH₃)OH |
| 524. | NHCH(CH₂CH₂CH₃)CH₂CH₂NH—C(O)CH(CH₃)OCH₃ |
| 525. | NHCH(CH₂CH₂CH₃)CH₂CH₂NH—C(O)CH₂CH(CH₃)OH |
| 526. | NHCH(CH₂CH₂CH₃)CH₂CH₂NH—C(O)CH₂CH(CH₃)OCH₃ |
| 527. | NHCH(CH₂CH₂CH₃)CH₂CH₂NH—C(O)CH(CH₃)CH₂OH |
| 528. | NHCH(CH₂CH₂CH₃)CH₂CH₂NH—C(O)CH(CH₃)CH₂OCH₃ |
| 529. | NHCH(CH(CH₃)₂)CH₂NHC(O)H |
| 530. | NHCH(CH(CH₃)₂)CH₂NH—C(O)CH₃ |
| 531. | NHCH(CH(CH₃)₂)CH₂NH—C(O)CH₂CH₃ |
| 532. | NHCH(CH(CH₃)₂)CH₂NH—C(O)CF₃ |
| 533. | NHCH(CH(CH₃)₂)CH₂NH—C(O)(CH₂)₂CH₃ |
| 534. | NHCH(CH(CH₃)₂)CH₂NH—C(O)CH₂OH |
| 535. | NHCH(CH(CH₃)₂)CH₂NH—C(O)CH₂OCH₃ |
| 536. | NHCH(CH(CH₃)₂)CH₂NH—C(O)CH(CH₃)OH |
| 537. | NHCH(CH(CH₃)₂)CH₂NH—C(O)CH(CH₃)OCH₃ |
| 538. | NHCH(CH(CH₃)₂)CH₂NH—C(O)CH₂CH(CH₃)OH |
| 539. | NHCH(CH(CH₃)₂)CH₂NH—C(O)CH(CH₃)₂)OCH₃ |
| 540. | NHCH(CH(CH₃)₂)CH₂NH—C(O)CH(CH₃)CH₂OH |
| 541. | NHCH(CH(CH₃)₂)CH₂NH—C(O)CH(CH₃)CH₂OCH₃ |
| 542. | NHCH(CH(CH₃)₂)CH₂CH₂NH—C(O)H |
| 543. | NHCH(CH(CH₃)₂)CH₂CH₂NH—C(O)CH₃ |
| 544. | NHCH(CH(CH₃)₂)CH₂CH₂NH—C(O)CH₂CH₃ |
| 545. | NHCH(CH(CH₃)₂)CH₂CH₂NH—C(O)CF₃ |
| 546. | NHCH(CH(CH₃)₂)CH₂CH₂NH—C(O)(CH₂)₂CH₃ |
| 547. | NHCH(CH(CH₃)₂)CH₂CH₂NH—C(O)CH₂OH |
| 548. | NHCH(CH(CH₃)₂)CH₂CH₂NH—C(O)CH₂OCH₃ |
| 549. | NHCH(CH(CH₃)₂)CH₂CH₂NH—C(O)CH(CH₃)OH |
| 550. | NHCH(CH(CH₃)₂)CH₂CH₂NH—C(O)CH(CH₃)OCH₃ |
| 551. | NHCH(CH(CH₃)₂)CH₂CH₂NH—C(O)CH₂CH(CH₃)OH |
| 552. | NHCH(CH(CH₃)₂)CH₂CH₂NH—C(O)CH₂CH(CH₃)OCH₃ |
| 553. | NHCH(CH(CH₃)₂)CH₂CH₂NH—C(O)CH(CH₃)CH₂OH |
| 554. | NHCH(CH(CH₃)₂)CH₂CH₂NH—C(O)CH(CH₃)CH₂OCH₃ |
| 555. | NHCH₂CH₂NHC(O)OCH₃ |
| 556. | NHCH₂CH₂NH—C(O)OCH₂CH₃ |
| 557. | NHCH₂CH₂NH—C(O)O(CH₂)₂CH₃ |
| 558. | NHCH₂CH₂NH—C(O)OCH(CH₃)OH |
| 559. | NHCH₂CH₂NH—C(O)OCH(CH₃)OCH₃ |
| 560. | NHCH₂CH₂NH—C(O)OCH₂CH(CH₃)OH |
| 561. | NHCH₂CH₂NH—C(O)OCH₂CH(CH₃)OCH₃ |
| 562. | NHCH₂CH₂NH—O(O)OCH(CH₃)CH₂OH |
| 563. | NHCH₂CH₂NH C(O)OCH(CH₃)CH₂OCH₃ |
| 564. | NHCH₂CH₂CH₂NH—C(O)OCH₃ |
| 565. | NHCH₂CH₂CH₂NH—C(O)OCH₂CH₃ |

TABLE A-continued

| No. | R6 |
|---|---|
| 566. | NHCH$_2$CH$_2$CH$_2$NH—C(O)O(CH$_2$)$_2$CH$_3$ |
| 567. | NHCH$_2$CH$_2$CH$_2$NH—C(O)OCH(CH$_3$)OH |
| 568. | NHCH$_2$CH$_2$CH$_2$NH—C(O)OCH(CH$_3$)OCH$_3$ |
| 569. | NHCH$_2$CH$_2$CH$_2$NH—C(O)OCH$_2$CH(CH$_3$)OH |
| 570. | NHCH$_2$CH$_2$CH$_2$NH—C(O)OCH$_2$CH(CH$_3$)OCH$_3$ |
| 571. | NHCH$_2$CH$_2$CH$_2$NH—C(O)OCH(CH$_3$)CH$_2$OH |
| 572. | NHCH$_2$CH$_2$CH$_2$NH—C(O)OCH(CH$_3$)CH$_2$OCH$_3$ |
| 573. | NHCH(CH$_3$)CH$_2$NH—C(O)OCH$_3$ |
| 574. | NHCH(CH$_3$)CH$_2$NH—C(O)OCH$_2$CH$_3$ |
| 575. | NHCH(CH$_3$)CH$_2$NH—C(O)O(CH$_2$)$_2$CH$_3$ |
| 576. | NHCH(CH$_3$)CH$_2$NH—C(O)OCH(CH$_3$)OH |
| 577. | NHCH(CH$_3$)CH$_2$NH—C(O)OCH(CH$_3$)OCH$_3$ |
| 578. | NHCH(CH$_3$)CH$_2$NH—C(O)OCH$_2$CH(CH$_3$)OH |
| 579. | NHCH(CH$_3$)CH$_2$NH—C(O)OCH$_2$CH(CH$_3$)OCH$_3$ |
| 580. | NHCH(CH$_3$)CH$_2$NH—C(O)OCH(CH$_3$)CH$_2$OH |
| 581. | NHCH(CH$_3$)CH$_2$NH—C(O)OCH(CH$_3$)CH$_2$OCH$_3$ |
| 582. | NHCH(CH$_3$)CH$_2$CH$_2$NH—C(O)OCH$_3$ |
| 583. | NHCH(CH$_3$)CH$_2$CH$_2$NH—C(O)OCH$_2$CH$_3$ |
| 584. | NHCH(CH$_3$)CH$_2$CH$_2$NH—C(O)O(CH$_2$)$_2$CH$_3$ |
| 585. | NHCH(CH$_3$)CH$_2$CH$_2$NH—C(O)OCH(CH$_3$)OH |
| 586. | NHCH(CH$_3$)CH$_2$CH$_2$NH—C(O)OCH(CH$_3$)OCH$_3$ |
| 587. | NHCH(CH$_3$)CH$_2$CH$_2$NH—C(O)OCH$_2$CH(CH$_3$)OH |
| 588. | NHCH(CH$_3$)CH$_2$CH$_2$NH—C(O)OCH$_2$CH(CH$_3$)OCH$_3$ |
| 589. | NHCH(CH$_3$)CH$_2$CH$_2$NH—C(O)OCH(CH$_3$)CH$_2$OH |
| 590. | NHCH(CH$_3$)CH$_2$CH$_2$NH—C(O)OCH(CH$_3$)CH$_2$OCH$_3$ |
| 591. | NHCH(CH$_2$CH$_3$)CH$_2$NH—C(O)OCH$_3$ |
| 592. | NHCH(CH$_2$CH$_3$)CH$_2$NH—C(O)OCH$_2$CH$_3$ |
| 593. | NHCH(CH$_2$CH$_3$)CH$_2$NH—C(O)O(CH$_2$)$_2$CH$_3$ |
| 594. | NHCH(CH$_2$CH$_3$)CH$_2$NH—C(O)OCH(CH$_3$)OH |
| 595. | NHCH(CH$_2$CH$_3$)CH$_2$NH—C(O)OCH(CH$_3$)OCH$_3$ |
| 596. | NHCH(CH$_2$CH$_3$)CH$_2$NH—C(O)OCH$_2$CH(CH$_3$)OH |
| 597. | NHCH(CH$_2$CH$_3$)CH$_2$NH—C(O)OCH$_2$CH(CH$_3$)OCH$_3$ |
| 598. | NHCH(CH$_2$CH$_3$)CH$_2$NH—C(O)OCH(CH$_3$)CH$_2$OH |
| 599. | NHCH(CH$_2$CH$_3$)CH$_2$NH—C(O)OCH(CH$_3$)CH$_2$OCH$_3$ |
| 600. | NHCH(CH$_2$CH$_3$)CH$_2$CH$_2$NH—C(O)OCH$_3$ |
| 601. | NHCH(CH$_2$CH$_3$)CH$_2$CH$_2$NH—C(O)OCH$_2$CH$_3$ |
| 602. | NHCH(CH$_2$CH$_3$)CH$_2$CH$_2$NH—C(O)O(CH$_2$)$_2$CH$_3$ |
| 603. | NHCH(CH$_2$CH$_3$)CH$_2$CH$_2$NH—C(O)OCH(CH$_3$)OH |
| 604. | NHCH(CH$_2$CH$_3$)CH$_2$CH$_2$NH—C(O)OCH(CH$_3$)OCH$_3$ |
| 605. | NHCH(CH$_2$CH$_3$)CH$_2$CH$_2$NH—C(O)OCH$_2$CH(CH$_3$)OH |
| 606. | NHCH(CH$_2$CH$_3$)CH$_2$CH$_2$NH—C(O)OCH$_2$CH(CH$_3$)OCH$_3$ |
| 607. | NHCH(CH$_2$CH$_3$)CH$_2$CH$_2$NH—C(O)OCH(CH$_3$)CH$_2$OH |
| 608. | NHCH(CH$_2$CH$_3$)CH$_2$CH$_2$NH—C(O)OCH(CH$_3$)CH$_2$OCH$_3$ |
| 609. | NHCH(CH$_2$CH$_2$CH$_3$)CH$_2$NH—C(O)OCH$_3$ |
| 610. | NHCH(CH$_2$CH$_2$CH$_3$)CH$_2$NH—C(O)OCH$_2$CH$_3$ |
| 611. | NHCH(CH$_2$CH$_2$CH$_3$)CH$_2$NH—C(O)O(CH$_2$)$_2$CH$_3$ |
| 612. | NHCH(CH$_2$CH$_2$CH$_3$)CH$_2$NH—C(O)OCH$_2$OCH$_3$ |
| 613. | NHCH(CH$_2$CH$_2$CH$_3$)CH$_2$NH—C(O)OCH(CH$_3$)OH |
| 614. | NHCH(CH$_2$CH$_2$CH$_3$)CH$_2$NH—C(O)OCH(CH$_3$)OCH$_3$ |
| 615. | NHCH(CH$_2$CH$_2$CH$_3$)CH$_2$NH—C(O)OCH$_2$CH(CH$_3$)OH |
| 616. | NHCH(CH$_2$CH$_2$CH$_3$)CH$_2$NH—C(O)OCH$_2$CH(CH$_3$)OCH$_3$ |
| 617. | NHCH(CH$_2$CH$_2$CH$_3$)CH$_2$NH—C(O)OCH(CH$_3$)CH$_2$OH |
| 618. | NHCH(CH$_2$CH$_2$CH$_3$)CH$_2$NH—C(O)OCH(CH$_3$)CH$_2$OCH$_3$ |
| 619. | NHCH(CH$_2$CH$_2$CH$_3$)CH$_2$CH$_2$NH—C(O)OCH$_3$ |
| 620. | NHCH(CH$_2$CH$_2$CH$_3$)CH$_2$CH$_2$NH—C(O)OCH$_2$CH$_3$ |
| 621. | NHCH(CH$_2$CH$_2$CH$_3$)CH$_2$CH$_2$NH—C(O)O(CH$_2$)$_2$CH$_3$ |
| 622. | NHCH(CH$_2$CH$_2$CH$_3$)CH$_2$CH$_2$NH—C(O)OCH(CH$_3$)OH |
| 623. | NHCH(CH$_2$CH$_2$CH$_3$)CH$_2$CH$_2$NH—C(O)OCH(CH$_3$)OCH$_3$ |
| 624. | NHCH(CH$_2$CH$_2$CH$_3$)CH$_2$CH$_2$NH—C(O)OCH$_2$CH(CH$_3$)OH |
| 625. | NHCH(CH$_2$CH$_2$CH$_3$)CH$_2$CH$_2$NH—C(O)OCH$_2$CH(CH$_3$)OCH$_3$ |
| 626. | NHCH(CH$_2$CH$_2$CH$_3$)CH$_2$CH$_2$NH—C(O)OCH(CH$_3$)CH$_2$OH |
| 627. | NHCH(CH$_2$CH$_2$CH$_3$)CH$_2$CH$_2$NH—C(O)OCH(CH$_3$)CH$_2$OCH$_3$ |
| 628. | NHCH(CH(CH$_3$)$_2$)CH$_2$NH—C(O)OCH$_3$ |
| 629. | NHCH(CH(CH$_3$)$_2$)CH$_2$NH—C(O)OCH$_2$CH$_3$ |
| 630. | NHCH(CH(CH$_3$)$_2$)CH$_2$NH—C(O)O(CH$_2$)$_2$CH$_3$ |
| 631. | NHCH(CH(CH$_3$)$_2$)CH$_2$NH—C(O)OCH(CH$_3$)OCH$_3$ |
| 632. | NHCH(CH(CH$_3$)$_2$)CH$_2$NH—C(O)OCH$_2$CH(CH$_3$)OH |
| 633. | NHCH(CH(CH$_3$)$_2$)CH$_2$NH—C(O)OCH(CH(CH$_3$)$_2$)OCH$_3$ |
| 634. | NHCH(CH(CH$_3$)$_2$)CH$_2$NH—C(O)OCH(CH$_3$)CH$_2$OH |
| 635. | NHCH(CH(CH$_3$)$_2$)CH$_2$NH—C(O)OCH(CH$_3$)CH$_2$OCH$_3$ |
| 636. | NHCH(CH(CH$_3$)$_2$)CH$_2$CH$_2$NH—C(O)OCH$_3$ |
| 637. | NHCH(CH(CH$_3$)$_2$)CH$_2$CH$_2$NH—C(O)OCH$_2$CH$_3$ |
| 638. | NHCH(CH(CH$_3$)$_2$)CH$_2$CH$_2$NH—C(O)O(CH$_2$)$_2$CH$_3$ |
| 639. | NHCH(CH(CH$_3$)$_2$)CH$_2$CH$_2$NH—C(O)OCH(CH$_3$)OCH$_3$ |
| 640. | NHCH(CH(CH$_3$)$_2$)CH$_2$CH$_2$NH—C(O)OCH$_2$CH(CH$_3$)OH |
| 641. | NHCH(CH(CH$_3$)$_2$)CH$_2$CH$_2$NH—C(O)OCH$_2$CH(CH$_3$)OCH$_3$ |
| 642. | NHCH(CH(CH$_3$)$_2$)CH$_2$CH$_2$NH—C(O)OCH(CH$_3$)CH$_2$OH |

TABLE A-continued

| No. | R6 |
|---|---|
| 643. | NHCH(CH(CH₃)₂)CH₂CH₂NH—C(O)OCH(CH₃)CH₂OCH₃ |
| 644. | NHCH₂CH₂NHC(O)NHCH₃ |
| 645. | NHCH₂CH₂NH—C(O)NHCH₂CH₃ |
| 646. | NHCH₂CH₂NH—C(O)NH(CH₂)₂CH₃ |
| 647. | NHCH₂CH₂NH—C(O)NHCH(CH₃)OH |
| 648. | NHCH₂CH₂NH—C(O)NHCH(CH₃)OCH₃ |
| 649. | NHCH₂CH₂NH—C(O)NHCH₂CH(CH₃)OH |
| 650. | NHCH₂CH₂NH—C(O)NHCH₂CH(CH₃)OCH₃ |
| 651. | NHCH₂CH₂NH—C(O)NHCH(CH₃)CH₂OH |
| 652. | NHCH₂CH₂NH C(O)NHCH(CH₃)CH₂OCH₃ |
| 653. | NHCH₂CH₂CH₂NH—C(O)NHCH₃ |
| 654. | NHCH₂CH₂CH₂NH—C(O)NHCH₂CH₃ |
| 655. | NHCH₂CH₂CH₂NH—C(O)NH(CH₂)₂CH₃ |
| 656. | NHCH₂CH₂CH₂NH—C(O)NHCH(CH₃)OH |
| 657. | NHCH₂CH₂CH₂NH—C(O)NHCH(CH₃)OCH₃ |
| 658. | NHCH₂CH₂CH₂NH—C(O)NHCH₂CH(CH₃)OH |
| 659. | NHCH₂CH₂CH₂NH—C(O)NHCH₂CH(CH₃)OCH₃ |
| 660. | NHCH₂CH₂CH₂NH—C(O)NHCH(CH₃)CH₂OH |
| 661. | NHCH₂CH₂CH₂NH—C(O)NHCH(CH₃)CH₂OCH₃ |
| 662. | NHCH(CH₃)CH₂NH—C(O)NHCH₃ |
| 663. | NHCH(CH₃)CH₂NH—C(O)NHCH₂CH₃ |
| 664. | NHCH(CH₃)CH₂NH—C(O)NH(CH₂)₂CH₃ |
| 665. | NHCH(CH₃)CH₂NH—C(O)NHCH(CH₃)OH |
| 666. | NHCH(CH₃)CH₂NH—C(O)NHCH(CH₃)OCH₃ |
| 667. | NHCH(CH₃)CH₂NH—C(O)NHCH₂CH(CH₃)OH |
| 668. | NHCH(CH₃)CH₂NH—C(O)NHCH₂CH(CH₃)OCH₃ |
| 669. | NHCH(CH₃)CH₂NH—C(O)NHCH(CH₃)CH₂OH |
| 670. | NHCH(CH₃)CH₂NH—C(O)NHCH(CH₃)CH₂OCH₃ |
| 671. | NHCH(CH₃)CH₂CH₂NH—C(O)NHCH₃ |
| 672. | NHCH(CH₃)CH₂CH₂NH—C(O)NHCH₂CH₃ |
| 673. | NHCH(CH₃)CH₂CH₂NH—C(O)NH(CH₂)₂CH₃ |
| 674. | NHCH(CH₃)CH₂CH₂NH—C(O)NHCH(CH₃)OH |
| 675. | NHCH(CH₃)CH₂CH₂NH—C(O)NHCH(CH₃)OCH₃ |
| 676. | NHCH(CH₃)CH₂CH₂NH—C(O)NHCH₂CH(CH₃)OH |
| 677. | NHCH(CH₃)CH₂CH₂NH—C(O)NHCH₂CH(CH₃)OCH₃ |
| 678. | NHCH(CH₃)CH₂CH₂NH—C(O)NHCH(CH₃)CH₂OH |
| 679. | NHCH(CH₃)CH₂CH₂NH—C(O)NHCH(CH₃)CH₂OCH₃ |
| 680. | NHCH(CH₂CH₃)CH₂NH—C(O)NHCH₃ |
| 681. | NHCH(CH₂CH₃)CH₂NH—C(O)NHCH₂CH₃ |
| 682. | NHCH(CH₂CH₃)CH₂NH—C(O)NH(CH₂)₂CH₃ |
| 683. | NHCH(CH₂CH₃)CH₂NH—C(O)NHCH(CH₃)OH |
| 684. | NHCH(CH₂CH₃)CH₂NH—C(O)NHCH(CH₃)OCH₃ |
| 685. | NHCH(CH₂CH₃)CH₂NH—C(O)NHCH₂CH(CH₃)OH |
| 686. | NHCH(CH₂CH₃)CH₂NH—C(O)NHCH₂CH(CH₃)OCH₃ |
| 687. | NHCH(CH₂CH₃)CH₂NH—C(O)NHCH(CH₃)CH₂OH |
| 688. | NHCH(CH₂CH₃)CH₂NH—C(O)NHCH(CH₃)CH₂OCH₃ |
| 689. | NHCH(CH₂CH₃)CH₂CH₂NH—C(O)NHCH₃ |
| 690. | NHCH(CH₂CH₃)CH₂CH₂NH—C(O)NHCH₂CH₃ |
| 691. | NHCH(CH₂CH₃)CH₂CH₂NH—C(O)NH(CH₂)₂CH₃ |
| 692. | NHCH(CH₂CH₃)CH₂CH₂NH—C(O)NHCH₂OCH₃ |
| 693. | NHCH(CH₂CH₃)CH₂CH₂NH—C(O)NHCH(CH₃)OH |
| 694. | NHCH(CH₂CH₃)CH₂CH₂NH—C(O)NHCH(CH₃)OCH₃ |
| 695. | NHCH(CH2CH₃)CH₂CH₂NH—C(O)NHCH₂CH(CH₃)OH |
| 696. | NHCH(CH₂CH₃)CH₂CH₂NH—C(O)NHCH₂CH(CH₃)OCH₃ |
| 697. | NHCH(CH₂CH₃)CH₂CH₂NH—C(O)NHCH(CH₃)CH₂ON |
| 698. | NHCH(CH₂CH₃)CH₂CH₂NH—C(O)NHCH(CH₃)CH₂OCH₃ |
| 699. | NHCH(CH₂CH₂CH₃)CH₂NH—C(O)NHCH₃ |
| 700. | NHCH(CH₂CH₂CH₃)CH₂NH—C(O)NHCH₂CH₃ |
| 701. | NHCH(CH₂CH₂CH₃)CH₂NH—C(O)NH(CH₂)₂CH₃ |
| 702. | NHCH(CH₂CH₂CH₃)CH₂NH—C(O)NHCH(CH₃)OH |
| 703. | NHCH(CH₂CH₂CH₃)CH₂NH—C(O)NHCH(CH₂)OCH₃ |
| 704. | NHCH(CH₂CH₂CH₃)CH₂NH—C(O)NHCH₂CH(CH₃)OH |
| 705. | NHCH(CH₂CH₂CH₃)CH₂NH—C(O)NHCH₂CH(CH₃)OCH₃ |
| 706. | NHCH(CH₂CH₂CH₃)CH₂NH—C(O)NHCH(CH₃)CH₂OH |
| 707. | NHCH(CH₂CH₂CH₃)CH₂NH—C(O)NHCH(CH₃)CH₂OCH₃ |
| 708. | NHCH(CH₂CH₂CH₃)CH₂CH₂NH—C(O)NHCH₃ |
| 709. | NHCH(CH₂CH₂CH₃)CH₂CH₂NH—C(O)NHCH₂CH₃ |
| 710. | NHCH(CH₂CH₂CH₃)CH₂CH₂NH—C(O)NH(CH₂)₂CH₃ |
| 711. | NHCH(CH₂CH₂CH₃)CH₂CH₂NH—C(O)NHCH(CH₃)OH |
| 712. | NHCH(CH₂CH₂CH₃)CH₂CH₂NH—C(O)NHCH(CH₃)OCH₃ |
| 713. | NHCH(CH₂CH₂CH₃)CH₂CH₂NH—C(O)NHCH₂CH(CH₃)OH |
| 714. | NHCH(CH₂CH₂CH₃)CH₂CH₂NH—C(O)NHCH₂CH(CH₃)OCH₃ |
| 715. | NHCH(CH₂CH₂CH₃)CH₂CH₂NH—C(O)NHCH(CH₃)CH₂OH |
| 716. | NHCH(CH₂CH₂CH₃)CH₂CH₂NH—C(O)NHCH(CH₃)CH₂OCH₃ |
| 717. | NHCH(CH(CH₃)₂)CH₂NH—C(O)NHCH₃ |
| 718. | NHCH(CH(CH₃)₂)CH₂NH—C(O)NHCH₂CH₃ |
| 719. | NHCH(CH(CH₃)₂)CH₂NH—C(O)NH(CH₂)₂CH₃ |

TABLE A-continued

| No. | R6 |
|---|---|
| 720. | NHCH(CH(CH₃)₂)CH₂NH—C(O)NHCH(CH₃)OCH₃ |
| 721. | NHCH(CH(CH₃)₂)CH₂NH—C(O)NHCH₂CH(CH₃)OH |
| 722. | NHCH(CH(CH₃)₂)CH₂NH—C(O)NHCH(CH(CH₃)₂)OCH₃ |
| 723. | NHCH(CH(CH₃)₂)CH₂NH—C(O)NHCH(CH₃)CH₂OH |
| 724. | NHCH(CH(CH₃)₂)CH₂NH—C(O)NHCH(CH₃)CH₂OCH₃ |
| 725. | NHCH(CH(CH₃)₂)CH₂CH₂NH—C(O)NHCH₃ |
| 726. | NHCH(CH(CH₃)₂)CH₂CH₂NH—C(O)NHCH₂CH₃ |
| 727. | NHCH(CH(CH₃)₂)CH₂CH₂NH—C(O)NH(CH₂)₂CH₃ |
| 728. | NHCH(CH(CH₃)₂)CH₂CH₂NH—C(O)NHCH₂OCH₃ |
| 729. | NHCH(CH(CH₃)₂)CH₂CH₂NH—C(O)NHCH₂CH(CH₃)OH |
| 730. | NHCH(CH(CH₃)₂)CH₂CH₂NH—C(O)NHCH₂CH(CH₃)OCH₃ |
| 731. | NHCH(CH(CH₃)₂)CH₂CH₂NH—C(O)NHCH(CH₃)CH₂OH |
| 732. | NHCH(CH(CH₃)₂)CH₂CH₂NH—C(O)NHCH(CH₃)CH₂OCH₃ |
| 733. | NHCH₂CH₂OC(O)H |
| 734. | NHCH₂CH₂OC(O)CH₃ |
| 735. | NHCHCH₂O—C(O)CH₂CH₃ |
| 736. | NHCH₂CH₂O—C(O)CF₃ |
| 737. | NHCH₂CH₂O—C(O)(CH₂)₂CH₃ |
| 738. | NHCH₂CH₂O—C(O)CH₂OH |
| 739. | NHCH₂CH₂O—C(O)CH₂OCH₃ |
| 740. | NHCH₂CH₂O—C(O)CH(CH₃)OH |
| 741. | NHCH₂CH₂OC(O)CH(CH₃)OCH₃ |
| 742. | NHCH₂CH₂O—C(O)CH₂CH(CH₃)OH |
| 743. | NHCH₂CH₂O—C(O)CH₂CH(CH₃)OCH₃ |
| 744. | NHCH₂CH₂O—C(O)CH(CH₃)CH₂OH |
| 745. | NHCH₂CH₂O—C(O)CH(CH₃)CH₂OCH₃ |
| 746. | NHCH₂CH₂CH₂OC(O)H |
| 747. | NHCH₂CH₂CH₂OC(O)CH₃ |
| 748. | NHCH₂CH₂CH₂O—C(O)CH₂CH₃ |
| 749. | NHCH₂CH₂CH₂OC(O)CF₃ |
| 750. | NHCH₂CH₂CH₂OC(O)(CH₂)₂CH₃ |
| 751. | NHCH₂CH₂CH₂OC(O)CH₂OH |
| 752. | NHCH₂CH₂CH₂O—C(O)CH₂OCH₃ |
| 753. | NHCH₂CH₂CH₂O—C(O)CH(CH₃)OH |
| 754. | NHCH₂CH₂CH₂O—C(O)CH(CH₃)OCH₃ |
| 755. | NHCH₂CH₂CH₂O—C(O)CH₂CH(CH₃)OH |
| 756. | NHCH₂CH₂CH₂O—C(O)CH₂CH(CH₃)OCH₃ |
| 757. | NHCH₂CH₂CH₂O—C(O)CH(CH₃)CH₂OH |
| 758. | NHCH₂CH₂CH₂O—C(O)CH(CH₃)CH₂OCH₃ |
| 759. | NHCH(CH₃)CH₂OC(O)H |
| 760. | NHCH(CH₃)CH₂OC(O)CH₃ |
| 761. | NHCH(CH₃)CH₂OC(O)CH₂CH₃ |
| 762. | NHCH(CH₃)CH₂OC(O)CF₃ |
| 763. | NHCH(CH₃)CH₂OC(O)(CH₂)₂CH₃ |
| 764. | NHCH(CH₃)CH₂OC(O)CH₂OH |
| 765. | NHCH(CH₃)CH₂OC(O)CH₂OCH₃ |
| 766. | NHCH(CH₃)CH₂OC(O)CH(CH₃)OH |
| 767. | NHCH(CH₃)CH₂O—C(O)CH(CH₃)OCH₃ |
| 768. | NHCH(CH₃)CH₂O—C(O)CH₂CH(CH₃)OH |
| 769. | NHCH(CH₃)CH₂O—C(O)CH₂CH(CH₃)OCH₃ |
| 770. | NHCH(CH₃)CH₂O—C(O)CH(CH₃)CH₂OH |
| 771. | NHCH(CH₃)CH₂0—C(O)CH(CH₃)CH₂OCH₃ |
| 772. | NHCH(CH₃)CH₂CH₂OC(O)H |
| 773. | NHCH(CH₃)CH₂CH₂OC(O)CH₃ |
| 774. | NHCH(CH₃)CH₂CH₂O—C(O)CH₂CH₃ |
| 775. | NHCH(CH₃)CH₂CH₂OC(O)CF₃ |
| 776. | NHCH(CH₃)CH₂CH₂O—C(O)(CH₂)₂CH₃ |
| 777. | NHCH(CH₃)CH₂CH₂OC(O)CH₂OH |
| 778. | NHCH(CH₃)CH₂CH₂O—C(O)CH₂OCH₃ |
| 779. | NHCH(CH₃)CH₂CH₂O—C(O)CH(CH₃)OH |
| 780. | NHCH(CH₃)CH₂CH₂O—C(O)CH(CH₃)OCH₃ |
| 781. | NHCH(CH₃)CH₂CH₂O—C(O)CH₂CH(CH₃)OH |
| 782. | NHCH(CH₃)CH₂CH₂O—C(O)CH₂CH(CH₃)OCH₃ |
| 783. | NHCH(CH₃)CH₂CH₂O—C(O)CH(CH₃)CH₂OH |
| 784. | NHCH(CH₃)CH₂CH₂O—C(O)CH(CH₃)CH₂OCH₃ |
| 785. | NHCH(CH₂CH₃)CH₂OC(O)H |
| 786. | NHCH(CH₂CH₃)CH₂OC(O)CH₃ |
| 787. | NHCH(CH₂CH₃)CH₂0—C(O)CH₂CH₃ |
| 788. | NHCH(CH₂CH₃)CH₂O—C(O)CF₃ |
| 789. | NHCH(CH₂CH₃)CH₂O—C(O)(CH₂)₂CH₃ |
| 790. | NHCH(CH₂CH₃)CH₂O—C(O)CH₂OH |
| 791. | NHCH(CH₂CH₃)CH₂O—C(O)CH₂OCH₃ |
| 792. | NHCH(CH₂CH₃)CH₂O—C(O)CH(CH₃)OH |
| 793. | NHCH(CH₂CH₃)CH₂O—C(O)CH(CH₃)OCH₃ |
| 794. | NHCH(CH₂CH₃)CH₂O—C(O)CH₂CH(CH₃)OH |
| 795. | NHCH(CH₂CH₃)CH₂O—C(O)CH₂CH(CH₃)OCH₃ |
| 796. | NHCH(CH₂CH₃)CH₂O—C(O)CH(CH₃)CH₂OH |
| 797. | NHCH(CH₂CH₃)CH₂O—C(O)CH(CH₃)CH₂OCH₃ |
| 798. | NHCH(CH₂CH₃)CH₂CH₂O—C(O)H |
| 799. | NHCH(CH₂CH₃)CH₂CH₂O—C(O)CH₃ |
| 800. | NHCH(CH₂CH₃)CH₂CH₂O—C(O)CH₂CH₃ |
| 801. | NHCH(CH₂CH₃)CH₂CH₂O—C(O)CF₃ |
| 802. | NHCH(CH₂CH₃)CH₂CH₂O—C(O)(CH₂)₂CH₃ |
| 803. | NHCH(CH₂CH₃)CH₂CH₂O—C(O)CH₂OH |
| 804. | NHCH(CH₂CH₃)CH₂CH₂O—C(O)CH₂OCH₃ |
| 805. | NHCH(CH₂CH₃)CH₂CH₂O—C(O)CH(CH₃)OH |
| 806. | NHCH(CH₂CH₃)CH₂CH₂O—C(O)CH(CH₃)OCH₃ |
| 807. | NHCH(CH₂CH₃)CH₂CH₂O—C(O)CH₂CH(CH₃)OH |
| 808. | NHCH(CH₂CH₃)CH₂CH₂O—C(O)CH₂CH(CH₃)OCH₃ |
| 809. | NHCH(CH₂CH₃)CH₂CH₂O—C(O)CH(CH₃)CH₂OH |
| 810. | NHCH(CH₂CH₃)CH₂CH₂O—C(O)CH(CH₃)CH₂OCH₃ |

TABLE A-continued

| No. | R6 |
|---|---|
| 811. | NHCH(CH$_2$CH$_2$CH$_3$)CH$_2$OC(O)H |
| 812. | NHCH(CH$_2$CH$_2$CH$_3$)CH$_2$O—C(O)CH$_3$ |
| 813. | NHCH(CH$_2$CH$_2$CH$_3$)CH$_2$O—C(O)CH$_2$CH$_3$ |
| 814. | NHCH(CH$_2$CH$_2$CH$_3$)CH$_2$O—C(O)CF$_3$ |
| 815. | NHCH(CH$_2$CH$_2$CH$_3$)CH$_2$O—C(O)(CH$_2$)$_2$CH$_3$ |
| 816. | NHCH(CH$_2$CH$_2$CH$_3$)CH$_2$O—C(O)CH$_2$OH |
| 817. | NHCH(CH$_2$CH$_2$CH$_3$)CH$_2$O—C(O)CH$_2$OCH$_3$ |
| 818. | NHCH(CH$_2$CH$_2$CH$_3$)CH$_2$O—C(O)CH(CH$_3$)OH |
| 819. | NHCH(CH$_2$CH$_2$CH$_3$)CH$_2$O—C(O)CH(CH$_3$)OCH$_3$ |
| 820. | NHCH(CH$_2$CH$_2$CH$_3$)CH$_2$O—C(O)CH$_2$CH(CH$_3$)OH |
| 821. | NHCH(CH$_2$CH$_2$CH$_3$)CH$_2$O—C(O)CH$_2$CH(CH$_3$)OCH$_3$ |
| 822. | NHCH(CH$_2$CH$_2$CH$_3$)CH$_2$O—C(O)CH(CH$_3$)CH$_2$OH |
| 823. | NHCH(CH$_2$CH$_2$CH$_3$)CH$_2$O—C(O)CH(CH$_3$)CH$_2$OCH$_3$ |
| 824. | NHCH(CH$_2$CH$_2$CH$_3$)CH$_2$CH$_2$O—C(O)H |
| 825. | NHCH(CH$_2$CH$_2$CH$_3$)CH$_2$CH$_2$O—C(O)CH$_3$ |
| 826. | NHCH(CH$_2$CH$_2$CH$_3$)CH$_2$CH$_2$O—C(O)CH$_2$CH$_3$ |
| 827. | NHCH(CH$_2$CH$_2$CH$_3$)CH$_2$CH$_2$O—C(O)CF$_3$ |
| 828. | NHCH(CH$_2$CH$_2$CH$_3$)CH$_2$CH$_2$O—C(O)(CH$_2$)$_2$CH$_3$ |
| 829. | NHCH(CH$_2$CH$_2$CH$_3$)CH$_2$CH$_2$O—C(O)CH$_2$OH |
| 830. | NHCH(CH$_2$CH$_2$CH$_3$)CH$_2$CH$_2$O—C(O)CH$_2$OCH$_3$ |
| 831. | NHCH(CH$_2$CH$_2$CH$_3$)CH$_2$CH$_2$O—C(O)CH(CH$_3$)OH |
| 832. | NHCH(CH$_2$CH$_2$CH$_3$)CH$_2$CH$_2$O—C(O)CH(CH$_3$)OCH$_3$ |
| 833. | NHCH(CH$_2$CH$_2$CH$_3$)CH$_2$CH$_2$O—C(O)CH$_2$CH(CH$_3$)OH |
| 834. | NHCH(CH$_2$CH$_2$CH$_3$)CH$_2$CH$_2$O—C(O)CH$_2$CH(CH$_3$)OCH$_3$ |
| 835. | NHCH(CH$_2$CH$_2$CH$_3$)CH$_2$CH$_2$O—C(O)CH(CH$_3$)CH$_2$OH |
| 836. | NHCH(CH$_2$CH$_2$CH$_3$)CH$_2$CH$_2$O—C(O)CH(CH$_3$)CH$_2$OCH$_3$ |
| 837. | NHCH(CH(CH$_3$)$_2$)CH$_2$OC(O)H |
| 838. | NHCH(CH(CH$_3$)$_2$)CH$_2$OC(O)CH$_3$ |
| 839. | NHCH(CH(CH$_3$)$_2$)CH$_2$O—C(O)CH$_2$CH$_3$ |
| 840. | NHCH(CH(CH$_3$)$_2$)CH$_2$OC(O)CF$_3$ |
| 841. | NHCH(CH(CH$_3$)$_2$)CH$_2$O—C(O)(CH$_2$)$_2$CH$_3$ |
| 842. | NHCH(CH(CH$_3$)$_2$)CH$_2$O—C(O)CH$_2$OH |
| 843. | NHCH(CH(CH$_3$)$_2$)CH$_2$O—C(O)CH$_2$OCH$_3$ |
| 844. | NHCH(CH(CH$_3$)$_2$)CH$_2$O—C(O)CH(CH$_3$)OH |
| 845. | NHCH(CH(CH$_3$)$_2$)CH$_2$O—C(O)CH(CH$_3$)OCH$_3$ |
| 846. | NHCH(CH(CH$_3$)$_2$)CH$_2$O—C(O)CH$_2$CH(CH$_3$)OH |
| 847. | NHCH(CH(CH$_3$)$_2$)CH$_2$O—C(O)CH(CH$_3$)$_2$)OCH$_3$ |
| 848. | NHCH(CH(CH$_3$)$_2$)CH$_2$O—C(O)CH(CH$_3$)CH$_2$OH |
| 849. | NHCH(CH(CH$_3$)$_2$)CH$_2$O—C(O)CH(CH$_3$)CH$_2$OCH$_3$ |
| 850. | NHCH(CH(CH$_3$)$_2$)CH$_2$CH$_2$O—C(O)H |
| 851. | NHCH(CH(CH$_3$)$_2$)CH$_2$CH$_2$O—C(O)CH$_3$ |
| 852. | NHCH(CH(CH$_3$)$_2$)CH$_2$CH$_2$O—C(O)CH$_2$CH$_3$ |
| 853. | NHCH(CH(CH$_3$)$_2$)CH$_2$CH$_2$O—C(O)CF$_3$ |
| 854. | NHCH(CH(CH$_3$)$_2$)CH$_2$CH$_2$O—C(O)(CH$_2$)$_2$CH$_3$ |
| 855. | NHCH(CH(CH$_3$)$_2$)CH$_2$CH$_2$O—C(O)CH$_2$OH |
| 856. | NHCH(CH(CH$_3$)$_2$)CH$_2$CH$_2$O—C(O)CH$_2$OCH$_3$ |
| 857. | NHCH(CH(CH$_3$)$_2$)CH$_2$CH$_2$O—C(O)CH(CH$_3$)OH |
| 858. | NHCH(CH(CH$_3$)$_2$)CH$_2$CH$_2$O—C(O)CH(CH$_3$)OCH$_3$ |
| 859. | NHCH(CH(CH$_3$)$_2$)CH$_2$CH$_2$O—C(O)CH$_2$CH(CH$_3$)OH |
| 860. | NHCH(CH(CH$_3$)$_2$)CH$_2$CH$_2$O—C(O)CH$_2$CH(CH$_3$)OCH$_3$ |
| 861. | NHCH(CH(CH$_3$)$_2$)CH$_2$CH$_2$O—C(O)CH(CH$_3$)CH$_2$OH |
| 862. | NHCH(CH(CH$_3$)$_2$)CH$_2$CH$_2$O—C(O)CH(CH$_3$)CH$_2$OCH$_3$ |
| 863. | NHCH$_2$CH$_2$OC(O)OCH$_3$ |
| 864. | NHCH$_2$CH$_2$OC(O)OCH$_2$CH$_3$ |
| 865. | NHCH$_2$CH$_2$OC(O)O(CH$_2$)$_2$CH$_3$ |
| 866. | NHCH$_2$CH$_2$OC(O)OCH(CH$_3$)OH |
| 867. | NHCH$_2$CH$_2$OC(O)OCH(CH$_3$)OCH$_3$ |
| 868. | NHCH$_2$CH$_2$O—C(O)OCH$_2$CH(CH$_3$)OH |
| 869. | NHCH$_2$CH$_2$O—C(O)OCH(CH$_3$)OCH$_3$ |
| 870. | NHCH$_2$CH$_2$O—C(O)OCH(CH$_3$)CH$_2$OH |
| 871. | NHCH$_2$CH$_2$O—C(O)OCH(CH$_3$)CH$_2$OCH$_3$ |
| 872. | NHCH$_2$CH$_2$CH$_2$OC(O)OCH$_3$ |
| 873. | NHCH$_2$CH$_2$CH$_2$OC(O)OCH$_2$CH$_3$ |
| 874. | NHCH$_2$CH$_2$CH$_2$O—C(O)O(CH$_2$)$_2$CH$_3$ |
| 875. | NHCH$_2$CH$_2$CH$_2$O—C(O)OCH(CH$_3$)OH |
| 876. | NHCH$_2$CH$_2$CH$_2$O—C(O)OCH(CH$_3$)OCH$_3$ |
| 877. | NHCH$_2$CH$_2$CH$_2$O—C(O)OCH$_2$CH(CH$_3$)OH |
| 878. | NHCH$_2$CH$_2$CH$_2$O—C(O)OCH$_2$CH(CH$_3$)OCH$_3$ |
| 879. | NHCH$_2$CH$_2$CH$_2$O—C(O)OCH(CH$_3$)CH$_2$OH |
| 880. | NHCH$_2$CH$_2$CH$_2$O—C(O)OCH(CH$_3$)CH$_2$OCH$_3$ |
| 881. | NHCH(CH$_3$)CH$_2$OC(O)OCH$_3$ |
| 882. | NHCH(CH$_3$)CH$_2$OC(O)OCH$_2$CH$_3$ |
| 883. | NHCH(CH$_3$)CH$_2$O—C(O)O(CH$_2$)$_2$CH$_3$ |
| 884. | NHCH(CH$_3$)CH$_2$O—C(O)OCH(CH$_3$)OH |
| 885. | NHCH(CH$_3$)CH$_2$O—C(O)OCH(CH$_3$)OCH$_3$ |
| 886. | NHCH(CH$_3$)CH$_2$O—C(O)OCH$_2$CH(CH$_3$)OH |
| 887. | NHCH(CH$_3$)CH$_2$O—C(O)OCH$_2$CH(CH$_3$)OCH$_3$ |
| 888. | NHCH(CH$_3$)CH$_2$O—C(O)OCH(CH$_3$)CH$_2$OH |
| 889. | NHCH(CH$_3$)CH$_2$O—C(O)OCH(CH$_3$)CH$_2$OCH$_3$ |
| 890. | NHCH(CH$_3$)CH$_2$CH$_2$O—C(O)OCH$_3$ |
| 891. | NHCH(CH$_3$)CH$_2$CH$_2$O—C(O)OCH$_2$CH$_3$ |
| 892. | NHCH(CH$_3$)CH$_2$CH$_2$O—C(O)O(CH$_2$)$_2$CH$_3$ |
| 893. | NHCH(CH$_3$)CH$_2$CH$_2$O—C(O)OCH(CH$_3$)OH |
| 894. | NHCH(CH$_3$)CH$_2$CH$_2$O—C(O)OCH(CH$_3$)OCH$_3$ |
| 895. | NHCH(CH$_3$)CH$_2$CH$_2$O—C(O)OCH$_2$CH(CH$_3$)OH |

TABLE A-continued

| No. | R6 |
|---|---|
| 896. | NHCH(CH₃)CH₂CH₂O—C(O)OCH₂CH(CH₃)OCH₃ |
| 897. | NHCH(CH₃)CH₂CH₂O—C(O)OCH(CH₃)CH₂OH |
| 898. | NHCH(CH₃)CH₂CH₂O—C(O)OCH(CH₃)CH₂OCH₃ |
| 899. | NHCH(CH₂CH₃)CH₂OC(O)OCH₃ |
| 900. | NHCH(CH₂CH₃)CH₂O—C(O)OCH₂CH₃ |
| 901. | NHCH(CH₂CH₃)CH₂O—C(O)O(CH₂)₂CH₃ |
| 902. | NHCH(CH₂CH₃)CH₂O—C(O)OCH(CH₃)OH |
| 903. | NHCH(CH₂CH₃)CH₂O—C(O)OCH(CH₃)OCH₃ |
| 904. | NHCH(CH₂CH₃)CH₂O—C(O)OCH₂CH(CH₃)OH |
| 905. | NHCH(CH₂CH₃)CH₂O—C(O)OCH₂CH(CH₃)OCH₃ |
| 906. | NHCH(CH₂CH₃)CH₂O—C(O)OCH(CH₃)CH₂OH |
| 907. | NHCH(CH₂CH₃)CH₂O—C(O)OCH(CH₃)CH₂OCH₃ |
| 908. | NHCH(CH₂CH₃)CH₂CH₂O—C(O)OCH₃ |
| 909. | NHCH(CH₂CH₃)CH₂CH₂O—C(O)OCH₂CH₃ |
| 910. | NHCH(CH₂CH₃)CH₂CH₂O—C(O)O(CH₂)₂CH₃ |
| 911. | NHCH(CH₂CH₃)CH₂CH₂O—C(O)OCH(CH₃)OH |
| 912. | NHCH(CH₂CH₃)CH₂CH₂O—C(O)OCH(CH₃)OCH₃ |
| 913. | NHCH(CH₂CH₃)CH₂CH₂O—C(O)OCH₂CH(CH₃)OH |
| 914. | NHCH(CH₂CH₃)CH₂CH₂O—C(O)OCH₂CH(CH₃)OCH₃ |
| 915. | NHCH(CH₂CH₃)CH₂CH₂O—C(O)OCH(CH₃)CH₂OH |
| 916. | NHCH(CH₂CH₃)CH₂CH₂O—C(O)OCH(CH₃)CH₂OCH₃ |
| 917. | NHCH(CH₂CH₂CH₃)CH₂O—C(O)OCH₃ |
| 918. | NHCH(CH₂CH₂CH₃)CH₂O—C(C)OCH₂CH₃ |
| 919. | NHCH(CH₂CH₂CH₃)CH₂O—C(O)O(CH₂)₂CH₃ |
| 920. | NHCH(CH₂CH₂CH₃)CH₂O—C(O)OCH₂OCH₃ |
| 921. | NHCH(CH₂CH₂CH₃)CH₂O—C(O)OCH(CH₃)OH |
| 922. | NHCH(CH₂CH₂CH₃)CH₂O—C(O)OCH(CH₃)OCH₃ |
| 923. | NHCH(CH₂CH₂CH₃)CH₂O—C(O)OCH₂CH(CH₃)OH |
| 924. | NHCH(CH₂CH₂CH₃)CH₂O—C(O)OCH₂CH(CH₃)OCH₃ |
| 925. | NHCH(CH₂CH₂CH₃)CH₂O—C(O)OCH(CH₃)CH₂OH |
| 926. | NHCH(CH₂CH₂CH₃)CH₂O—C(O)OCH(CH₃)CH₂OCH₃ |
| 927. | NHCH(CH₂CH₂CH₃)CH₂CH₂O—C(O)OCH₃ |
| 928. | NHCH(CH₂CH₂CH₃)CH₂CH₂O—C(O)OCH₂CH₃ |
| 929. | NHCH(CH₂CH₂CH₃)CH₂CH₂O—C(O)O(CH₂)₂CH₃ |
| 930. | NHCH(CH₂CH₂CH₃)CH₂CH₂O—C(O)OCH(CH₃)OH |
| 931. | NHCH(CH₂CH₂CH₃)CH₂CH₂O—C(O)OCH(CH₃)OCH₃ |
| 932. | NHCH(CH₂CH₂CH₃)CH₂CH₂O—C(O)OCH₂CH(CH₃)OH |
| 933. | NHCH(CH₂CH₂CH₃)O—C(O)OCH₂CH(CH₃)OCH₃ |
| 934. | NHCH(CH₂CH₂CH₃)CH₂O—C(O)OCH(CH₃)CH₂OH |
| 935. | NHCH(CH₂CH₂CH₃)CH₂CH₂O—C(O)OCH(CH₃)CH₂OCH₃ |
| 936. | NHCH(CH(CH₃)₂)CH₂O—C(O)OCH₃ |
| 937. | NHCH(CH(CH₃)₂)CH₂O—C(O)OCH₂CH₃ |
| 938. | NHCH(CH(CH₃)₂)CH₂O—C(O)O(CH₂)₂CH₃ |
| 939. | NHCH(CH(CH₃)₂)CH₂O—C(O)OCH(CH₃)OCH₃ |
| 940. | NHCH(CH(CH₃)₂)CH₂O—C(O)OCH₂CH(CH₃)OH |
| 941. | NHCH(CH(CH₃)₂)CH₂O—C(O)OCH(CH(CH₃)₂)OCH₃ |
| 942. | NHCH(CH(CH₃)₂)CH₂O—C(O)OCH(CH₃)CH₂OH |
| 943. | NHCH(CH(CH₃)₂)CH₂O—C(O)OCH(CH₃)CH₂OCH₃ |
| 944. | NHCH(CH(CH₃)₂)CH₂CH₂O—C(O)OCH₃ |
| 945. | NHCH(CH(CH₃)₂)CH₂CH₂O—C(O)OCH₂CH₃ |
| 946. | NHCH(CH(CH₃)₂)CH₂CH₂O—C(O)O(CH₂)₂CH₃ |
| 947. | NHCH(CH(CH₃)₂)CH₂CH₂O—C(O)OCH(CH₃)OCH₃ |
| 948. | NHCH(CH(CH₃)₂)CH₂CH₂O—C(O)OCH₂CH(CH₃)OH |
| 949. | NHCH(CH(CH₃)₂)CH₂CH₂O—C(O)OCH₂CH(CH₃)OCH₃ |
| 950. | NHCH(CH(CH₃)₂)CH₂CH₂O—C(O)OCH(CH₃)CH₂OH |
| 951. | NHCH(CH(CH₃)₂)CH₂CH₂O—C(O)OCH(CH₃)CH₂OCH₃ |
| 952. | NHCH₂COOH |
| 953. | NHCH₂C(O)OCH₃ |
| 954. | NHCH₂C(O)OCH₂CH₃ |
| 955. | NHCH₂C(O)O(CH₂)₂CH₃ |
| 956. | NHCH₂C(O)OCH(CH₃)OH |
| 957. | NHCH₂C(O)OCH(CH₃)OCH₃ |
| 958. | NHCH₂C(O)OCH₂CH(CH₃)OH |
| 959. | NHCH₂C(O)OCH₂CH(CH₃)OCH₃ |
| 960. | NHCH₂C(O)OCH(CH₃)CH₂OH |
| 961. | NHCH₂C(O)OCH(CH₃)CH₂OCH₃ |
| 962. | NHCH₂C(O)NH₂ |
| 963. | NHCH₂C(O)NHOH |
| 964. | NHCH₂C(NH)NH₂ |
| 965. | NHCH₂C(O)NHCH₃ |
| 966. | NHCH₂C(O)NHCH₂CH₃ |
| 967. | NHCH₂C(O)NH(CH₂)₂CH₃ |
| 968. | NHCH₂C(O)NHCH(CH₃)OH |
| 969. | NHCH₂C(O)NHCH(CH₃)OCH₃ |
| 970. | NHCH₂C(O)NHCH(CH₃)OH |
| 971. | NHCH₂C(O)NHCH(CH₃)OCH₃ |
| 972. | NHCH₂C(O)NHCH(CH₃)CH₂OH |
| 973. | NHCH₂C(O)NHCH(CH₃)CH₂OCH₃ |
| 974. | NHCH₂C(O)N(CH₃)₂ |
| 975. | NHCH₂C(O)N(CH₂CH₃)₂ |
| 976. | NHCH(CH₃)COOH |
| 977. | NHCH(CH₃)C(O)OCH₃ |
| 978. | NHCH(CH₃)C(O)OCH₂CH₃ |
| 979. | NHCH(CH₃)C(O)O(CH₂)₂CH₃ |
| 980. | NHCH(CH₃)C(O)OCH(CH₃)OH |
| 981. | NHCH(CH₃)C(O)OCH(CH₃)OCH₃ |
| 982. | NHCH(CH₃)C(O)OCH₂CH(CH₃)OH |
| 983. | NHCH(CH₃)C(O)—OCH₂CH(CH₃)OCH₃ |
| 984. | NHCH(CH₃)C(O)OCH(CH₃)CH₂OH |
| 985. | NHCH(CH₃)C(O)—OCH(CH₃)CH₂OCH₃ |
| 986. | NHCH(CH₃)C(O)NH₂ |
| 987. | NHCH(CH₃)C(O)NHOH |
| 988. | NHCH(CH₃)C(NH)NH₂ |
| 989. | NHCH(CH₃)C(O)NHCH₃ |
| 990. | NHCH(CH₃)C(O)NHCH₂CH₃ |
| 991. | NHCH(CH₃)C(O)NH(CH₂)₂CH₃ |
| 992. | NHCH(CH₃)C(O)NHCH(CH₃)OH |

TABLE A-continued

| No. | R6 |
|---|---|
| 993. | NHCH(CH₃)C(O)NHCH(CH₃)OCH₃ |
| 994. | NHCH(CH₃)C(O)—NHCH₂CH(CH₃)OH |
| 995. | NHCH(CH₃)C(O)—NHCH₂CH(CH₃)OCH₃ |
| 996. | NHCH(CH₃)C(O)—NHCH(CH₃)CH₂OH |
| 997. | NHCH(CH₃)C(O)—NHCH(CH₃)CH₂OCH₃ |
| 998. | NHCH(CH₃)C(O)N(CH₃)₂ |
| 999. | NHCH(CH₃)C(O)N(CH₂CH₃)₂ |
| 1000. | NHCH₂CH₂COOH |
| 1001. | NHCH₂CH₂C(O)OCH₃ |
| 1002. | NHCH₂CH₂C(O)OCH₂CH₃ |
| 1003. | NHCH₂CH₂C(O)O(CH₂)₂CH₃ |
| 1004. | NHCH₂CH₂C(O)OCH(CH₃)OH |
| 1005. | NHCH₂CH₂C(O)OCH(CH₃)OCH₃ |
| 1006. | NHCH₂CH₂C(O)OCH₂CH(CH₃)OH |
| 1007. | NHCH₂CH₂C(O)—OCH₂CH(CH₃)OCH₃ |
| 1008. | NHCH₂CH₂C(O)OCH(CH₃)CH₂OH |
| 1009. | NHCH₂CH₂C(O)—OCH(CH₃)CH₂OCH₃ |
| 1010. | NHCH₂CH₂C(O)NH₂ |
| 1011. | NHCH₂CH₂C(O)NHOH |
| 1012. | NHCH₂CH₂C(NH)NH₂ |
| 1013. | NHCH₂CH₂C(O)NHCH₃ |
| 1014. | NHCH₂CH₂C(O)NHCH₂CH₃ |
| 1015. | NHCH₂CH₂C(O)NH(CH₂)₂CH₃ |
| 1016. | NHCH₂CH₂C(O)NHCH(CH₃)OH |
| 1017. | NHCH₂CH₂C(O)NHCH(CH₃)OCH₃ |
| 1018. | NHCH₂CH₂C(O)—NHCH₂CH(CH₃)OH |
| 1019. | NHCH₂CH₂C(O)—NHCH₂CH(CH₃)OCH₃ |
| 1020. | NHCH₂CH₂C(O)—NHCH(CH₃)CH₂OH |
| 1021. | NHCH₂CH₂C(O)—NHCH(CH₃)CH₂OCH₃ |
| 1022. | NHCH₂CH₂C(O)N(CH₃)₂ |
| 1023. | NHCH₂CH₂C(O)N(CH₂CH₃)₂ |
| 1024. | NHCH₂OCH₃ |
| 1025. | NHCH₂OCH₂CH₃ |
| 1026. | NHCH₂O(CH₂)₂CH₃ |
| 1027. | NHCH₂OCH(CH₃)₂ |
| 1028. | NHCH₂OCH₂OCH₃ |
| 1029. | NHCH₂CH₂OH |
| 1030. | NHCH₂CH₂OCH₃ |
| 1031. | NHCH₂CH₂OCH₂CH₃ |
| 1032. | NHCH₂CH₂O(CH₂)₂CH₃ |
| 1033. | NHCH₂CH₂OCH(CH₃)₂ |
| 1034. | NHCH₂CH₂OCH₂OCH₃ |
| 1035. | NHCH₂CH₂CH₂OH |
| 1036. | NHCH₂CH₂CH₂OCH₃ |
| 1037. | NHCH₂CH₂CH₂OCH₂CH₃ |
| 1038. | NHCH₂CH₂CH₂O(CH₂)₂CH₃ |
| 1039. | NHCH₂CH₂CH₂OCH(CH₃)₂ |
| 1040. | NHCH₂CH₂CH₂OCH₂OCH₃ |
| 1041. | NHCH(CH₃)OCH₃ |
| 1042. | NHCH(CH₃)OCH₂CH₃ |
| 1043. | NHCH(CH₃)O(CH₂)₂CH₃ |
| 1044. | NHCH(CH₃)OCH(CH₃)₂ |
| 1045. | NHCH(CH₃)OCH₂OCH₃ |
| 1046. | NHC[(CH₃)₂]OCH₃ |
| 1047. | NHC[(CH₃)₂]PCH₂CH₃ |
| 1048. | NHC[(CH₃)₂]O(CH₂)₂CH₃ |
| 1049. | NHC[(CH₃)₂]OCH(CH₃)₂ |
| 1050. | NHC[(CH₃)₂]OCH₂OCH₃ |
| 1051. | NHCH(CH₂CH₃)OCH₃ |
| 1052. | NHCH(CH₂CH₃)OCH₂CH₃ |
| 1053. | NHCH(CH₂CH₃)O(CH₂)₂CH₃ |
| 1054. | NHCH(CH₂CH₃)OCH(CH₃)₂ |
| 1055. | NHCH(CH₂CH₃)OCH₂OCH₃ |
| 1056. | NHCH(CH₂CH)OCH₃ |
| 1057. | NHCH(CH₂CH)OCH₂CH₃ |
| 1058. | NHCH(CH₂CH)O(CH₂)₂CH₃ |
| 1059. | NHCH(CH₂CH)OCH(CH₃)₂ |
| 1060. | NHCH(CH₂CH)OCH₂OCH₃ |
| 1061. | NHCH(CH₂OCH₃)OCH₃ |
| 1062. | NHCH(CH₂OCH₃)OCH₂CH₃ |
| 1063. | NHCH(CH₂OCH₃)O(CH₂)₂CH₃ |
| 1064. | NHCH(CH₂OCH₃)OCH(CH₃)₂ |
| 1065. | NHCH(CH₂OCH₃)OCH₂OCH₃ |
| 1066. | NHCH[CH(CH₃)₂]OCH₃ |
| 1067. | NHCH[CH(CH₃)₂]OCH₂CH₃ |
| 1068. | NHCH[CH(CH₃)₂]O(CH₂)₂CH₃ |
| 1069. | NHCH{CH(CH₃)₂]OCH(CH₃)₂ |
| 1070. | NHCH[CH(CH₃)₂]OCH₂OCH₃ |
| 1071. | NHCH(CH(CH₂CH₃)CH₃)OCH₃ |
| 1072. | NHCH(CH(CH₂CH₃)CH₃)—OCH₂CH₃ |
| 1073. | NHCH(CH(CH₂CH₃)CH₃)—O(CH₂)₂CH₃ |
| 1074. | NHCH(CH(CH₂CH₃)CH₃)—OCH(CH₃)₂ |
| 1075. | NHCH(CH(CH₂CH₃)CH₃)—OCH₂OCH₃ |
| 1076. | NHCH(CH₂CH₂CH₃)OCH₃ |
| 1077. | NHCH(CH₂CH₂CH₃)OCH₂CH₃ |
| 1078. | NHCH(CH₂CH₂CH₃)O(CH₂)₂CH₃ |
| 1079. | NHCH(CH₂CH₂CH₃)OCH(CH₃)₂ |
| 1080. | NHCH(CH₂CH₂CH₃)OCH₂OCH₃ |
| 1081. | NHCH(CH₃)CH₂OH |
| 1082. | NHCH(CH₃)CH₂OCH₃ |
| 1083. | NHCH(CH₃)CH₂OCH₂CH₃ |
| 1084. | NHCH(CH₃)CH₂O(CH₂)₂CH₃ |
| 1085. | NHCH(CH₃)CH₂OCH(CH₃)₂ |
| 1086. | NHCH(CH₃)CH₂OCH₂OCH₃ |
| 1087. | NHCH(CH₂CH₃)CH₂OH |
| 1088. | NHCH(CH₂CH₃)CH₂OCH₃ |
| 1089. | NHCH(CH₂CH₃)CH₂OCH₂CH₃ |
| 1090. | NHCH(CH₂CH₃)CH₂O(CH₂)₂CH₃ |
| 1091. | NHCH(CH₂CH₃)CH₂OCH(CH₃)₂ |
| 1092. | NHCH(CH₂CH₃)CH₂OCH₂OCH₃ |
| 1093. | NHC[(CH₃)₂]CH₂OH |
| 1094. | NHC[(CH₃)₂]CH₂OCH₃ |
| 1095. | NHC[(CH₃)₂]CH₂OCH₂CH₃ |
| 1096. | NHC[(CH₃)₂]CH₂O(CH₂)₂CH₃ |
| 1097. | NHC[(CH₃)₂]CH₂OCH(CH₃)₂ |
| 1098. | NHC[(CH₃)₂]CH₂OCH₂OCH₃ |
| 1099. | NHCH(CH₂CH)CH₂OH |
| 1100. | NHCH(CH₂CH)CH₂OCH₃ |
| 1101. | NHCH(CH₂CH)CH₂OCH₂CH₃ |
| 1102. | NHCH(CH₂CH)CH₂O(CH₂)₂CH₃ |
| 1103. | NHCH(CH₂CH)CH₂OCH(CH₃)₂ |
| 1104. | NHCH(CH₂CH)CH₂OCH₂OCH₃ |
| 1105. | NHCH(CH₂OCH₃)CH₂OH |
| 1106. | NHCH(CH₂OCH₃)CH₂OCH₃ |
| 1107. | NHCH(CH₂OCH₃)CH₂OCH₂CH₃ |
| 1108. | NHCH(CH₂OCH₃)CH₂O—(CH₂)₂CH₃ |
| 1109. | NHCH(CH₂OCH₃)CH₂OCH(CH₃)₂ |
| 1110. | NHCH(CH₂OCH₃)CH₂OCH₂OCH₃ |
| 1111. | NHCH₂CH(CH₃)OH |
| 1112. | NHCH₂CH(CH₃)OCH₃ |
| 1113. | NHCH₂CH(CH₃)OCH₂CH₃ |
| 1114. | NHCH₂CH(CH₃)O(CH₂)₂CH₃ |
| 1115. | NHCH₂CH(CH₃)OCH(CH₃)₂ |
| 1116. | NHCH₂CH(CH₃)OCH₂OCH₃ |
| 1117. | NHCH₂CH(CH₂CH₃)OH |
| 1118. | NHCH₂CH(CH₂CH₃)OCH₃ |
| 1119. | NHCH₂CH(CH₂CH₃)OCH₂CH₃ |
| 1120. | NHCH₂CH(CH₂CH₃)O(CH₂)₂CH₃ |
| 1121. | NHCH₂CH(CH₂CH₃)OCH(CH₃)₂ |
| 1122. | NHCH₂CH(CH₂CH₃)OCH₂OCH₃ |
| 1123. | NHCH₂CH(CH₂CH)OH |
| 1124. | NHCH₂CH(CH₂CH)OCH₃ |
| 1125. | NHCH₂CH(CH₂CH)OCH₂CH₃ |
| 1126. | NHCH₂C(CH₂CH)(CH₂CH)O—(CH₂)₂CH₃ |
| 1127. | NHCH₂CH(CH₂CH)OCH(CH₃)₂ |
| 1128. | NHCH₂CH(CH₂CH)OCH₂OCH₃ |
| 1129. | NHCH₂CH(CH₂OCH₃)OH |
| 1130. | NHCH₂CH(CH₂OCH₃)OCH₃ |
| 1131. | NHCH₂CH(CH₂OCH₃)OCH₂CH₃ |
| 1132. | NHCH₂CH(CH₂OCH₃)O—(CH₂)₂CH₃ |
| 1133. | NHCH₂CH(CH₂OCH₃)OCH(CH₃)₂ |

TABLE A-continued

| No. | R6 |
|---|---|
| 1134. | NHCH$_2$CH(CH$_2$OCH$_3$)OCH$_2$OCH$_3$ |
| 1135. | NHCH(CH$_3$)CH$_2$OH |
| 1136. | NHCH(CH$_3$)CH$_2$OCH$_3$ |
| 1137. | NHCH(CH$_3$)CH$_2$CH$_2$OCH$_2$CH$_3$ |
| 1138. | NHCH(CH$_3$)CH$_2$CH$_2$O(CH$_2$)$_2$CH$_3$ |
| 1139. | NHCH(CH$_3$)CH$_2$CH$_2$OCH(CH$_3$)$_2$ |
| 1140. | NHCH(CH$_3$)CH$_2$CH$_2$OCH$_2$OCH$_3$ |
| 1141. | NHCH(CH$_2$CH$_3$)CH$_2$CH$_2$OH |
| 1142. | NHCH(CH$_2$CH$_3$)CH$_2$CH$_2$OCH$_3$ |
| 1143. | NHCH(CH$_2$CH$_3$)CH$_2$CH$_2$O—CH$_2$CH$_3$ |
| 1144. | NHCH(CH$_2$CH$_3$)CH$_2$CH$_2$O—(CH$_2$)$_2$CH$_3$ |
| 1145. | NHCH(CH$_2$CH$_3$)CH$_2$CH$_2$O—CH(CH$_3$)$_2$ |
| 1146. | NHCH(CH$_2$CH$_3$)CH$_2$CH$_2$O—CH$_2$OCH$_3$ |
| 1147. | NHC[(CH$_3$)$_2$]CH$_2$CH$_2$OH |
| 1148. | NHC[(CH$_3$)$_2$]CH$_2$CH$_2$OCH$_3$ |
| 1149. | NHC[(CH$_3$)$_2$]CH$_2$CH$_2$OCH$_2$CH$_3$ |
| 1150. | NHC[(CH$_3$)$_2$]CH$_2$CH$_2$O(CH$_2$)$_2$CH$_3$ |
| 1151. | NHC[(CH$_3$)$_2$]CH$_2$CH$_2$OCH(CH$_3$)$_2$ |
| 1152. | NHC[(CH$_3$)$_2$]CH$_2$CH$_2$OCH$_2$OCH$_3$ |
| 1153. | NHCH(CH$_2$CH)CH$_2$CH$_2$OH |
| 1154. | NHCH(CH$_2$CH)CH$_2$CH$_2$OCH$_3$ |
| 1155. | NHCH(CH$_2$CH)CH$_2$CH$_2$OCH$_2$CH$_3$ |
| 1156. | NHCH(CH$_2$CH)CH$_2$CH$_2$O—(CH$_2$)$_2$CH$_3$ |
| 1157. | NHCH(CH$_2$CH)CH$_2$CH$_2$O—CH(CH$_3$)$_2$ |
| 1158. | NHCH(CH$_2$CH)CH$_2$CH$_2$O—CH$_2$OCH$_3$ |
| 1159. | NHCH(CH$_2$OCH$_3$)CH$_2$CH$_2$OH |
| 1160. | NHCH(CH$_2$OCH$_3$)CH$_2$CH$_2$OCH$_3$ |
| 1161. | NHCH(CH$_2$OCH$_3$)CH$_2$CH$_2$O—CH$_2$CH$_3$ |
| 1162. | NHCH(CH$_2$OCH$_3$)CH$_2$CH$_2$O—(CH$_2$)$_2$CH$_3$ |
| 1163. | NHCH(CH$_2$OCH$_3$)CH$_2$CH$_2$O—CH(CH$_3$)$_2$ |
| 1164. | NHCH(CH$_2$OCH$_3$)CH$_2$CH$_2$O—CH$_2$OCH$_3$ |
| 1165. | NHCH(CH$_3$)CH(CH$_3$)OH |
| 1166. | NHCH(CH$_3$)CH(CH$_3$)OCH$_3$ |
| 1167. | NHCH(CH$_3$)CH(CH$_3$)OCH$_2$CH$_3$ |
| 1168. | NHCH(CH$_3$)CH(CH$_3$)O(CH$_2$)$_2$CH$_3$ |
| 1169. | NHCH(CH$_3$)CH(CH$_3$)OCH(CH$_3$)$_2$ |
| 1170. | NHCH(CH$_3$)CH(CH$_3$)OCH$_2$OCH$_3$ |
| 1171. | NHCH(CH$_2$CH$_3$)CH(CH$_3$)OH |
| 1172. | NHCH(CH$_2$CH$_3$)CH(CH$_3$)OCH$_3$ |
| 1173. | NHCH(CH$_2$CH$_3$)CH(CH$_3$)O—CH$_2$CH$_3$ |
| 1174. | NHCH(CH$_2$CH$_3$)CH(CH$_3$)O—(CH$_2$)$_2$CH$_3$ |
| 1175. | NHCH(CH$_2$CH$_3$)CH(CH$_3$)O—CH(CH$_3$)$_2$ |
| 1176. | NHCH(CH$_2$CH$_3$)CH(CH$_3$)O—CH$_2$OCH$_3$ |
| 1177. | NHC[(CH$_3$)$_2$]CH(CH$_3$)OH |
| 1178. | NHC[(CH$_3$)$_2$]CH(CH$_3$)OCH$_3$ |
| 1179. | NHC[(CH$_3$)$_2$]CH(CH$_3$)OCH$_2$CH$_3$ |
| 1180. | NHC[(CH$_3$)$_2$]CH(CH$_3$)O(CH$_2$)$_2$CH$_3$ |
| 1181. | NHC[(CH$_3$)$_2$]CH(CH$_3$)OCH(CH$_3$)$_2$ |
| 1182. | NHC[(CH$_3$)$_2$]CH(CH$_3$)OCH$_2$OCH$_3$ |
| 1183. | NHCH(CH$_2$CH)CH(CH$_3$)OH |
| 1184. | NHCH(CH$_2$CH)CH(CH$_3$)OCH$_3$ |
| 1185. | NHCH(CH$_2$CH)CH(CH$_3$)OCH$_2$CH$_3$ |
| 1186. | NHCH(CH$_2$CH)CH(CH$_3$)O—(CH$_2$)$_2$CH$_3$ |
| 1187. | NHCH(CH$_2$CH)CH(CH$_3$)O—CH(CH$_3$)$_2$ |
| 1188. | NHCH(CH$_2$CH)CH(CH$_3$)O—CH$_2$OCH$_3$ |
| 1189. | NHCH(CH$_2$OCH$_3$)CH(CH$_3$)OH |
| 1190. | NHCH(CH$_2$OCH$_3$)CH(CH$_3$)OCH$_3$ |
| 1191. | NHCH(CH$_2$OCH$_3$)CH(CH$_3$)O—CH$_2$CH$_3$ |
| 1192. | NHCH(CH$_2$OCH$_3$)CH(CH$_3$)O—(CH$_2$)$_2$CH$_3$ |
| 1193. | NHCH(CH$_2$OCH$_3$)CH(CH$_3$)O—CH(CH$_3$)$_2$ |
| 1194. | NHCH(CH$_2$OCH$_3$)CH(CH$_3$)O—CH$_2$OCH$_3$ |
| 1195. | N(CH$_3$)CH$_2$OCH$_3$ |
| 1196. | N(CH$_3$)CH$_2$OCH$_2$CH$_3$ |
| 1197. | N(CH$_3$)CH$_2$O(CH$_2$)$_2$CH$_3$ |
| 1198. | N(CH$_3$)CH$_2$OCH(CH$_3$)$_2$ |
| 1199. | N(CH$_3$)CH$_2$OCH$_2$OCH$_3$ |
| 1200. | N(CH$_3$)CH$_2$CH$_2$OH |
| 1201. | N(CH$_3$)CH$_2$CH$_2$OCH$_3$ |
| 1202. | N(CH$_3$)CH$_2$CH$_2$OCH$_2$CH$_3$ |
| 1203. | N(CH$_3$)CH$_2$CH$_2$O(CH$_2$)$_2$CH$_3$ |
| 1204. | N(CH$_3$)CH$_2$CH$_2$OCH(CH$_3$)$_2$ |
| 1205. | N(CH$_3$)CH$_2$CH$_2$OCH$_2$OCH$_3$ |
| 1206. | N(CH$_3$)CH$_2$CH$_2$CH$_2$OH |
| 1207. | N(CH$_3$)CH$_2$CH$_2$CH$_2$OCH$_3$ |
| 1208. | N(CH$_3$)CH$_2$CH$_2$CH$_2$OCH$_2$CH$_3$ |
| 1209. | N(CH$_3$)CH$_2$CH$_2$CH$_2$O(CH$_2$)$_2$CH$_3$ |
| 1210. | N(CH$_3$)CH$_2$CH$_2$CH$_2$OCH(CH$_3$)$_2$ |
| 1211. | N(CH$_3$)CH$_2$CH$_2$CH$_2$OCH$_2$OCH$_3$ |
| 1212. | N(CH$_3$)CH(CH$_3$)OCH$_3$ |
| 1213. | N(CH$_3$)CH(CH$_3$)OCH$_2$CH$_3$ |
| 1214. | N(CH$_3$)CH(CH$_3$)O(CH$_2$)$_2$CH$_3$ |
| 1215. | N(CH$_3$)CH(CH$_3$)OCH(CH$_3$)$_2$ |
| 1216. | N(CH$_3$)CH(CH$_3$)OCH$_2$OCH$_3$ |
| 1217. | N(CH$_3$)CH(CH$_2$CH)O(CH$_2$)$_2$CH$_3$ |
| 1218. | N(CH$_3$)CH(CH$_2$CH)OCH(CH$_3$)$_2$ |
| 1219. | N(CH$_3$)CH(CH$_2$CH)OCH$_2$OCH$_3$ |
| 1220. | N(CH$_3$)CH(CH$_2$OCH$_3$)OCH$_3$ |
| 1221. | N(CH$_3$)CH(CH$_2$OCH$_3$)OCH$_2$CH$_3$ |
| 1222. | N(CH$_3$)CH(CH$_2$OCH$_3$)O—(CH$_2$)$_2$CH$_3$ |
| 1223. | N(CH$_3$)CH(CH$_2$OCH$_3$)OCH(CH$_3$)$_2$ |
| 1224. | N(CH$_3$)CH(CH$_2$OCH$_3$)OCH$_2$OCH$_3$ |
| 1225. | N(CH$_3$)CH(CH$_3$)CH$_2$OH |
| 1226. | N(CH$_3$)CH(CH$_3$)CH$_2$OCH$_3$ |
| 1227. | N(CH$_3$)CH(CH$_3$)CH$_2$OCH$_2$CH$_3$ |
| 1228. | N(CH$_3$)CH(CH$_3$)CH$_2$O(CH$_2$)$_2$CH$_3$ |
| 1229. | N(CH$_3$)CH(CH$_3$)CH$_2$OCH(CH$_3$)$_2$ |
| 1230. | N(CH$_3$)CH(CH$_3$)CH$_2$OCH$_2$OCH$_3$ |
| 1231. | N(CH$_3$)CH(CH$_2$CH$_3$)CH$_2$OH |
| 1232. | N(CH$_3$)CH(CH$_2$CH$_3$)CH$_2$OCH$_3$ |
| 1233. | N(CH$_3$)CH(CH$_2$CH$_3$)CH$_2$OCH$_2$CH$_3$ |
| 1234. | N(CH$_3$)CH(CH$_2$CH$_3$)CH$_2$O—(CH$_2$)$_2$CH$_3$ |
| 1235. | N(CH$_3$)CH(CH$_2$CH$_3$)CH$_2$O—CH(CH$_3$)$_2$ |
| 1236. | N(CH$_3$)CH(CH$_2$CH$_3$)CH$_2$O—CH$_2$OCH$_3$ |
| 1237. | N(CH$_3$)CH(CH$_2$CH)CH$_2$OH |
| 1238. | N(CH$_3$)CH(CH$_2$CH)CH$_2$OCH$_3$ |
| 1239. | N(CH$_3$)CH(CH$_2$CH)CH$_2$OCH$_2$CH$_3$ |
| 1240. | N(CH$_3$)CH(CH$_2$CH)CH$_2$O—(CH$_2$)$_2$CH$_3$ |
| 1241. | N(CH$_3$)CH(CH$_2$CH)CH$_2$O—CH(CH$_3$)$_2$ |
| 1242. | N(CH$_3$)CH(CH$_2$CH)CH$_2$O—CH$_2$OCH$_3$ |
| 1243. | N(CH$_3$)CH(CH$_2$OCH$_3$)CH$_2$OH |
| 1244. | N(CH$_3$)CH(CH$_2$OCH$_3$)CH$_2$OCH$_3$ |
| 1245. | N(CH$_3$)CH(CH$_2$OCH$_3$)CH$_2$O—CH$_2$CH$_3$ |
| 1246. | N(CH$_3$)CH(CH$_2$OCH$_3$)CH$_2$O—(CH$_2$)$_2$CH$_3$ |
| 1247. | N(CH$_3$)CH(CH$_2$OCH$_3$)CH$_2$O—CH(CH$_3$)$_2$ |
| 1248. | N(CH$_3$)CH(CH$_2$OCH$_3$)CH$_2$O—CH$_2$OCH$_3$ |
| 1249. | N(CH$_3$)CH$_2$CH(CH$_3$)OH |
| 1250. | N(CH$_3$)CH$_2$CH(CH$_3$)OCH$_3$ |
| 1251. | N(CH$_3$)CH$_2$CH(CH$_3$)OCH$_2$CH$_3$ |
| 1252. | N(CH$_3$)CH$_2$CH(CH$_3$)O(CH$_2$)$_2$CH$_3$ |
| 1253. | N(CH$_3$)CH$_2$CH(CH$_3$)OCH(CH$_3$)$_2$ |
| 1254. | N(CH$_3$)CH$_2$CH(CH$_3$)OCH$_2$OCH$_3$ |
| 1255. | N(CH$_3$)CH$_2$CH(CH$_2$CH$_3$)OH |
| 1256. | N(CH$_3$)CH$_2$CH(CH$_2$CH$_3$)OCH$_3$ |
| 1257. | N(CH$_3$)CH$_2$CH(CH$_2$CH$_3$)OCH$_2$CH$_3$ |
| 1258. | N(CH$_3$)CH$_2$CH(CH$_2$CH$_3$)O—(CH$_2$)$_2$CH$_3$ |
| 1259. | N(CH$_3$)CH$_2$CH(CH$_2$CH$_3$)O—CH(CH$_3$)$_2$ |
| 1260. | N(CH$_3$)CH$_2$CH(CH$_2$CH$_3$)O—CH$_2$OCH$_3$ |
| 1261. | N(CH$_3$)CH$_2$CH(CH$_2$CH)OH |
| 1262. | N(CH$_3$)CH$_2$CH(CH$_2$CH)OCH$_3$ |
| 1263. | N(CH$_3$)CH$_2$CH(CH$_2$CH)OCH$_2$CH$_3$ |
| 1264. | N(CH$_3$)CH$_2$CH(CH$_2$CH)(CH$_2$CH)—O(CH$_2$)$_2$CH$_3$ |
| 1265. | N(CH$_3$)CH$_2$CH(CH$_2$CH)—OCH(CH$_3$)$_2$ |
| 1266. | N(CH$_3$)CH$_2$CH(CH$_2$CH)O—CH$_2$OCH$_3$ |
| 1267. | N(CH$_3$)CH$_2$CH(CH$_2$OCH$_3$)OH |
| 1268. | N(CH$_3$)CH$_2$CH(CH$_2$OCH$_3$)OCH$_3$ |
| 1269. | N(CH$_3$)CH$_2$CH(CH$_2$OCH$_3$)O—CH$_2$CH$_3$ |

TABLE A-continued

| No. | R6 |
|---|---|
| 1270. | N(CH$_3$)CH$_2$CH(CH$_2$OCH$_3$)O—(CH$_2$)$_2$CH$_3$ |
| 1271. | N(CH$_3$)CH$_2$CH(CH$_2$OCH$_3$)O—CH(CH$_3$)$_2$ |
| 1272. | N(CH$_3$)CH$_2$CH(CH$_2$OCH$_3$)O—CH$_2$OCH$_3$ |
| 1273. | N(CH$_3$)CH(CH$_3$)CH$_2$CH$_2$OH |
| 1274. | N(CH$_3$)CH(CH$_3$)CH$_2$CH$_2$OCH$_3$ |
| 1275. | N(CH$_3$)CH(CH$_3$)CH$_2$CH$_2$OCH$_2$CH$_3$ |
| 1276. | N(CH$_3$)CH(CH$_3$)CH$_2$CH$_2$O—(CH$_2$)$_2$CH$_3$ |
| 1277. | N(CH$_3$)CH(CH$_3$)CH$_2$CH$_2$O—CH(CH$_3$)$_2$ |
| 1278. | N(CH$_3$)CH(CH$_3$)CH$_2$CH$_2$O—CH$_2$OCH$_3$ |
| 1279. | N(CH$_3$)CH(CH$_2$CH$_3$)CH$_2$CH$_2$OH |
| 1280. | N(CH$_3$)CH(CH$_2$CH$_3$)CH$_2$CH$_2$OCH$_3$ |
| 1281. | N(CH$_3$)CH(CH$_2$CH$_3$)CH$_2$CH$_2$O—CH$_2$CH$_3$ |
| 1282. | N(CH$_3$)CH(CH$_2$CH$_3$)CH$_2$CH$_2$O—(CH$_2$)$_2$CH$_3$ |
| 1283. | N(CH$_3$)CH(CH$_2$CH$_3$)CH$_2$CH$_2$O—CH(CH$_3$)$_2$ |
| 1284. | N(CH$_3$)CH(CH$_2$CH$_3$)CH$_2$CH$_2$O—CH$_2$OCH$_3$ |
| 1285. | N(CH$_3$)C[(CH$_3$)$_2$]CH$_2$CH$_2$OH |
| 1286. | N(CH$_3$)C[(CH$_3$)$_2$]CH$_2$CH$_2$OCH$_3$ |
| 1287. | N(CH$_3$)C[(CH$_3$)$_2$]CH$_2$CH$_2$O—CH$_2$CH$_3$ |
| 1288. | N(CH$_3$)C[(CH$_3$)$_2$]CH$_2$CH$_2$O—(CH$_2$)$_2$CH$_3$ |
| 1289. | N(CH$_3$)C[(CH$_3$)$_2$]CH$_2$CH$_2$O—CH(CH$_3$)$_2$ |
| 1290. | N(CH$_3$)C[(CH$_3$)$_2$]CH$_2$CH$_2$O—CH$_2$OCH$_3$ |
| 1291. | N(CH$_3$)CH(CH$_2$CH)CH$_2$CH$_2$OH |
| 1292. | N(CH$_3$)CH(CH$_2$CH)CH$_2$CH$_2$OCH$_3$ |
| 1293. | N(CH$_3$)CH(CH$_2$CH)—CH$_2$CH$_2$OCH$_2$CH$_3$ |
| 1294. | N(CH$_3$)CH(CH$_2$CH)CH$_2$CH$_2$O—(CH$_2$)$_2$CH$_3$ |
| 1295. | N(CH$_3$)CH(CH$_2$CH)CH$_2$CH$_2$O—CH(CH$_3$)$_2$ |
| 1296. | N(CH$_3$)CH(CH$_2$CH)CH$_2$CH$_2$O—CH$_2$OCH$_3$ |
| 1297. | N(CH$_3$)CH(CH$_2$OCH$_3$)CH$_2$CH$_2$OH |
| 1298. | N(CH$_3$)CH(CH$_2$OCH$_3$)—CH$_2$CH$_2$OCH$_3$ |
| 1299. | N(CH$_3$)CH(CH$_2$OCH$_3$)CH$_2$CH$_2$O—CH$_2$CH$_3$ |
| 1300. | N(CH$_3$)CH(CH$_2$OCH$_3$)CH$_2$CH$_2$O—(CH$_2$)$_2$CH$_3$ |
| 1301. | N(CH$_3$)CH(CH$_2$OCH$_3$)CH$_2$CH$_2$O—CH(CH$_3$)$_2$ |
| 1302. | N(CH$_3$)CH(CH$_2$OCH$_3$)CH$_2$CH$_2$O—CH$_2$OCH$_3$ |
| 1303. | N(CH$_2$CH$_3$)CH$_2$OCH$_3$ |
| 1304. | N(CH$_2$CH$_3$)CH$_2$OCH$_2$CH$_3$ |
| 1305. | N(CH$_2$CH$_3$)CH$_2$O(CH$_2$)$_2$CH$_3$ |
| 1306. | N(CH$_2$CH$_3$)CH$_2$OCH(CH$_3$)$_2$ |
| 1307. | N(CH$_2$CH$_3$)CH$_2$OCH$_2$OCH$_3$ |
| 1308. | N(CH$_2$CH$_3$)CH$_2$CH$_2$OH |
| 1309. | N(CH$_2$CH$_3$)CH$_2$CH$_2$OCH$_3$ |
| 1310. | N(CH$_2$CH$_3$)CH$_2$CH$_2$OCH$_2$CH$_3$ |
| 1311. | N(CH$_2$CH$_3$)CH$_2$CH$_2$O(CH$_2$)$_2$CH$_3$ |
| 1312. | N(CH$_2$CH$_3$)CH$_2$CH$_2$OCH(CH$_3$)$_2$ |
| 1313. | N(CH$_2$CH$_3$)CH$_2$CH$_2$OCH$_2$OCH$_3$ |
| 1314. | N(CH$_2$CH$_3$)CH$_2$CH$_2$CH$_2$OH |
| 1315. | N(CH$_2$CH$_3$)CH$_2$CH$_2$CH$_2$OCH$_3$ |
| 1316. | N(CH$_2$CH$_3$)CH$_2$CH$_2$CH$_2$OCH$_2$CH$_3$ |
| 1317. | N(CH$_2$CH$_3$)CH$_2$CH$_2$CH$_2$O—(CH$_2$)$_2$CH$_3$ |
| 1318. | N(CH$_2$CH$_3$)CH$_2$CH$_2$CH$_2$O—CH(CH$_3$)$_2$ |
| 1319. | N(CH$_2$CH$_3$)CH$_2$CH$_2$CH$_2$O—CH$_2$OCH$_3$ |
| 1320. | N(CH$_2$CH$_3$)CH(CH$_3$)OCH$_3$ |
| 1321. | N(CH$_2$CH$_3$)CH(CH$_3$)OCH$_2$CH$_3$ |
| 1322. | N(CH$_2$CH$_3$)CH(CH$_3$)O(CH$_2$)$_2$CH$_3$ |
| 1323. | N(CH$_2$CH$_3$)CH(CH$_3$)OCH(CH$_3$)$_2$ |
| 1324. | N(CH$_2$CH$_3$)CH(CH$_3$)OCH$_2$OCH$_3$ |
| 1325. | N(CH$_2$CH$_3$)CH(CH$_2$CH)O—(CH$_2$)$_2$CH$_3$ |
| 1326. | N(CH$_2$CH$_3$)CH(CH$_2$CH)O—CH(CH$_3$)$_2$ |
| 1327. | N(CH$_2$CH$_3$)CH(CH$_2$CH)O—CH$_2$OCH$_3$ |
| 1328. | N(CH$_2$CH$_3$)CH(CH$_2$OCH$_3$)OCH$_3$ |
| 1329. | N(CH$_2$CH$_3$)CH(CH$_2$OCH$_3$)O—CH$_2$CH$_3$ |
| 1330. | N(CH$_2$CH$_3$)CH(CH$_2$OCH$_3$)O—(CH$_2$)$_2$CH$_3$ |
| 1331. | N(CH$_2$CH$_3$)CH(CH$_2$OCH$_3$)O—CH(CH$_3$)$_2$ |
| 1332. | N(CH$_2$CH$_3$)CH(CH$_2$OCH$_3$)O—CH$_2$OCH$_3$ |
| 1333. | N(CH$_2$CH$_3$)CH(CH$_3$)CH$_2$OH |
| 1334. | N(CH$_2$CH$_3$)CH(CH$_3$)CH$_2$OCH$_3$ |
| 1335. | N(CH$_2$CH$_3$)CH(CH$_3$)CH$_2$OCH$_2$CH$_3$ |
| 1336. | N(CH$_2$CH$_3$)CH(CH$_3$)CH$_2$O—(CH$_2$)$_2$CH$_3$ |
| 1337. | N(CH$_2$CH$_3$)CH(CH$_3$)CH$_2$O—CH(CH$_3$)$_2$ |
| 1338. | N(CH$_2$CH$_3$)CH(CH$_3$)CH$_2$O—CH$_2$OCH$_3$ |
| 1339. | N(CH$_2$CH$_3$)CH(CH$_2$CH$_3$)CH$_2$OH |
| 1340. | N(CH$_2$CH$_3$)CH(CH$_2$CH$_3$)CH$_2$OCH$_3$ |
| 1341. | N(CH$_2$CH$_3$)CH(CH$_2$CH$_3$)CH$_2$O—CH$_3$ |
| 1342. | N(CH$_2$CH$_3$)CH(CH$_2$CH$_3$)CH$_2$O—(CH$_2$)$_2$CH$_3$ |
| 1343. | N(CH$_2$CH$_3$)CH(CH$_2$CH$_3$)CH$_2$O—CH(CH$_3$)$_2$ |
| 1344. | N(CH$_2$CH$_3$)CH(CH$_2$CH$_3$)CH$_2$O—CH$_2$OCH$_3$ |
| 1345. | N(CH$_2$CH$_3$)CH(CH$_2$CH)CH$_2$OH |
| 1346. | N(CH$_2$CH$_3$)CH(CH$_2$CH)CH$_2$OCH$_3$ |
| 1347. | N(CH$_2$CH$_3$)CH(CH$_2$CH)CH$_2$O—CH$_2$CH$_3$ |
| 1348. | N(CH$_2$CH$_3$)CH(CH$_2$CH)CH$_2$O—(CH$_2$)$_2$CH$_3$ |
| 1349. | N(CH$_2$CH$_3$)CH(CH$_2$CH)CH$_2$O—CH(CH$_3$)$_2$ |
| 1350. | N(CH$_2$CH$_3$)CH(CH$_2$CH)CH$_2$O—CH$_2$OCH$_3$ |
| 1351. | N(CH$_2$CH$_3$)CH(CH$_2$OCH$_3$)CH$_2$OH |
| 1352. | N(CH$_2$CH$_3$)CH(CH$_2$OCH$_3$)CH$_2$O—CH$_3$ |
| 1353. | N(CH$_2$CH$_3$)CH(CH$_2$OCH$_3$)CH$_2$O—CH$_2$CH$_3$ |
| 1354. | N(CH$_2$CH$_3$)CH(CH$_2$OCH$_3$)CH$_2$O—(CH$_2$)$_2$CH$_3$ |
| 1355. | N(CH$_2$CH$_3$)CH(CH$_2$OCH$_3$)CH$_2$O—CH(CH$_3$)$_2$ |
| 1356. | N(CH$_2$CH$_3$)CH(CH$_2$OCH$_3$)CH$_2$O—CH$_2$OCH$_3$ |
| 1357. | N(CH$_2$CH$_3$)CH$_2$CH(CH$_3$)OH |
| 1358. | N(CH$_2$CH$_3$)CH$_2$CH(CH$_3$)OCH$_3$ |
| 1359. | N(CH$_2$CH$_3$)CH$_2$CH(CH$_3$)OCH$_2$CH$_3$ |
| 1360. | N(CH$_2$CH$_3$)CH$_2$CH(CH$_3$)O—(CH$_2$)$_2$CH$_3$ |
| 1361. | N(CH$_2$CH$_3$)CH$_2$CH(CH$_3$)O—CH(CH$_3$)$_2$ |
| 1362. | N(CH$_2$CH$_3$)CH$_2$CH(CH$_3$)O—CH$_2$OCH$_3$ |
| 1363. | N(CH$_2$CH$_3$)CH$_2$CH(CH$_2$CH$_3$)OH |
| 1364. | N(CH$_2$CH$_3$)CH$_2$CH(CH$_2$CH$_3$)OCH$_3$ |
| 1365. | N(CH$_2$CH$_3$)CH$_2$CH(CH$_2$CH$_3$)O—CH$_2$CH$_3$ |
| 1366. | N(CH$_2$CH$_3$)CH$_2$CH(CH$_2$CH$_3$)O—(CH$_2$)$_2$CH$_3$ |
| 1367. | N(CH$_2$CH$_3$)CH$_2$CH(CH$_2$CH$_3$)O—CH(CH$_3$)$_2$ |
| 1368. | N(CH$_2$CH$_3$)CH$_2$CH(CH$_2$CH$_3$)O—CH$_2$OCH$_3$ |
| 1369. | N(CH$_2$CH$_3$)CH$_2$CH(CH$_2$CH)OH |
| 1370. | N(CH$_2$CH$_3$)CH$_2$CH(CH$_2$CH)OCH$_3$ |
| 1371. | N(CH$_2$CH$_3$)CH$_2$CH(CH$_2$CH)O—CH$_2$CH$_3$ |
| 1372. | N(CH$_2$CH$_3$)CH$_2$C(CH$_2$CH)(CH$_2$CH)O—(CH$_2$)$_2$CH$_3$ |
| 1373. | N(CH$_2$CH$_3$)CH$_2$CH(CH$_2$CH)—OCH(CH$_3$)$_2$ |
| 1374. | N(CH$_2$CH$_3$)CH$_2$CH(CH$_2$CH)O—CH$_2$OCH$_3$ |
| 1375. | N(CH$_2$CH$_3$)CH$_2$CH(CH$_2$OCH$_3$)OH |
| 1376. | N(CH$_2$CH$_3$)CH$_2$CH(CH$_2$OCH$_3$)O—CH$_3$ |
| 1377. | N(CH$_2$CH$_3$)CH$_2$CH(CH$_2$OCH$_3$)O—CH$_2$CH$_3$ |
| 1378. | N(CH$_2$CH$_3$)CH$_2$CH(CH$_2$OCH$_3$)O—(CH$_2$)$_2$CH$_3$ |

TABLE A-continued

| No. | R6 |
|---|---|
| 1379. | $N(CH_2CH_3)CH_2CH(CH_2OCH_3)O—CH(CH_3)_2$ |
| 1380. | $N(CH_2CH_3)CH_2CH(CH_2OCH_3)O—CH_2OCH_3$ |
| 1381. | $N(CH_2CH_3)CH(CH_3)CH_2CH_2OH$ |
| 1382. | $N(CH_2CH_3)CH(CH_3)CH_2CH_2OCH_3$ |
| 1383. | $N(CH_2CH_3)CH(CH_3)CH_2CH_2O—CH_2CH_3$ |
| 1384. | $N(CH_2CH_3)CH(CH_3)CH_2CH_2O—(CH_2)_2CH_3$ |
| 1385. | $N(CH_2CH_3)CH(CH_3)CH_2CH_2O—CH(CH_3)_2$ |
| 1386. | $N(CH_2CH_3)CH(CH_3)CH_2CH_2O—CH_2OCH_3$ |
| 1387. | $N(CH_2CH_3)CH(CH_2CH_3)—CH_2CH_2OH$ |
| 1388. | $N(CH_2CH_3)CH(CH_2CH_3)—CH_2CH_2OCH_3$ |
| 1389. | $N(CH_2CH_3)CH(CH_2CH_3)—CH_2CH_2OCH_2CH_3$ |
| 1390. | $N(CH_2CH_3)CH(CH_2CH_3)—CH_2CH_2O(CH_2)_2CH_3$ |
| 1391. | $N(CH_2CH_3)CH(CH_2CH_3)—CH_2CH_2OCH(CH_3)_2$ |
| 1392. | $N(CH_2CH_3)CH(CH_2CH_3)—CH_2CH_2OCH_2OCH_3$ |
| 1393. | $N(CH_2CH_3)C[(CH_3)_2]CH_2CH_2OH$ |
| 1394. | $N(CH_2CH_3)C[(CH_3)_2]—CH_2CH_2OCH_3$ |
| 1395. | $N(CH_2CH_3)C[(CH_3)_2]CH_2CH_2O—CH_2CH_3$ |
| 1396. | $N(CH_2CH_3)C[(CH_3)_2]CH_2CH_2O—(CH_2)_2CH_3$ |
| 1397. | $N(CH_2CH_3)C[(CH_3)_2]CH_2CH_2O—CH(CH_3)_2$ |
| 1398. | $N(CH_2CH_3)C[(CH_3)_2]CH_2CH_2O—CH_2OCH_3$ |
| 1399. | $N(CH_2CH_3)CH(CH_2CH)—CH_2CH_2OH$ |
| 1400. | $N(CH_2CH_3)CH(CH_2CH)—CH_2CH_2OCH_3$ |
| 1401. | $N(CH_2CH_3)CH(CH_2CH)—CH_2CH_2OCH_2CH_3$ |
| 1402. | $N(CH_2CH_3)CH(CH_2CH)—CH_2CH_2O(CH_2)_2CH_3$ |
| 1403. | $N(CH_2CH_3)CH(CH_2CH)—CH_2CH_2OCH(CH_3)_2$ |
| 1404. | $N(CH_2CH_3)CH(CH_2CH)—CH_2CH_2OCH_2OCH_3$ |
| 1405. | $N(CH_2CH_3)CH(CH_2OCH_3)—CH_2CH_2OH$ |
| 1406. | $N(CH_2CH_3)CH(CH_2OCH_3)—CH_2CH_2OCH_3$ |
| 1407. | $N(CH_2CH_3)CH(CH_2OCH_3)—CH_2CH_2OCH_2CH_3$ |
| 1408. | $N(CH_2CH_3)CH(CH_2OCH_3)—CH_2CH_2O(CH_2)_2CH_3$ |
| 1409. | $N(CH_2CH_3)CH(CH_2OCH_3)—CH_2CH_2OCH(CH_3)_2$ |
| 1410. | $N(CH_2CH_3)CH(CH_2OCH_3)—CH_2CH_2OCH_2OCH_3$ |
| 1411. | $N(CH_2OCH_3)CH_2OCH_3$ |
| 1412. | $N(CH_2OCH_3)CH_2OCH_2CH_3$ |
| 1413. | $N(CH_2OCH_3)CH_2O(CH_2)_2CH_3$ |
| 1414. | $N(CH_2OCH_3)CH_2OCH(CH_3)_2$ |
| 1415. | $N(CH_2OCH_3)CH_2OCH_2OCH_3$ |
| 1416. | $N(CH_2OCH_3)CH_2CH_2OH$ |
| 1417. | $N(CH_2OCH_3)CH_2CH_2OCH_3$ |
| 1418. | $N(CH_2OCH_3)CH_2CH_2OCH_2CH_3$ |
| 1419. | $N(CH_2OCH_3)CH_2CH_2O(CH_2)_2CH_3$ |
| 1420. | $N(CH_2OCH_3)CH_2CH_2OCH(CH_3)_2$ |
| 1421. | $N(CH_2OCH_3)CH_2CH_2OCH_2OCH_3$ |
| 1422. | $N(CH_2OCH_3)CH_2CH_2CH_2OH$ |
| 1423. | $N(CH_2OCH_3)CH_2CH_2CH_2OCH_3$ |
| 1424. | $N(CH_2OCH_3)CH_2CH_2CH_2O—CH_2CH_3$ |
| 1425. | $N(CH_2OCH_3)CH_2CH_2CH_2O—(CH_2)_2CH_3$ |
| 1426. | $N(CH_2OCH_3)CH_2CH_2CH_2O—CH(CH_3)_2$ |
| 1427. | $N(CH_2OCH_3)CH_2CH_2CH_2O—CH_2OCH_3$ |
| 1428. | $N(CH_2OCH_3)CH(CH_3)OCH_3$ |
| 1429. | $N(CH_2OCH_3)CH(CH_3)OCH_2CH_3$ |
| 1430. | $N(CH_2OCH_3)CH(CH_3)O—(CH_2)_2CH_3$ |
| 1431. | $N(CH_2OCH_3)CH(CH_3)OCH(CH_3)_2$ |
| 1432. | $N(CH_2OCH_3)CH(CH_3)OCH_2OCH_3$ |
| 1433. | $N(CH_2OCH_3)CH(CH_2CH)O—(CH_2)_2CH_3$ |
| 1434. | $N(CH_2OCH_3)CH(CH_2CH)O—CH(CH_3)_2$ |
| 1435. | $N(CH_2OCH_3)CH(CH_2CH)O—CH_2OCH_3$ |
| 1436. | $N(CH_2OCH_3)CH(CH_2OCH_3)OCH_3$ |
| 1437. | $N(CH_2OCH_3)CH(CH_2OCH_3)O—CH_2CH_3$ |
| 1438. | $N(CH_2OCH_3)CH(CH_2OCH_3)O—(CH_2)_2CH_3$ |
| 1439. | $N(CH_2OCH_3)CH(CH_2OCH_3)O—CH(CH_3)_2$ |
| 1440. | $N(CH_2OCH_3)CH(CH_2OCH_3)O—CH_2OCH_3$ |
| 1441. | $N(CH_2OCH_3)CH(CH_3)CH_2OH$ |
| 1442. | $N(CH_2OCH_3)CH(CH_3)CH_2OCH_3$ |
| 1443. | $N(CH_2OCH_3)CH(CH_3)CH_2O—CH_2CH_3$ |
| 1444. | $N(CH_2OCH_3)CH(CH_3)CH_2O—(CH_2)_2CH_3$ |
| 1445. | $N(CH_2OCH_3)CH(CH_3)CH_2O—CH(CH_3)_2$ |
| 1446. | $N(CH_2OCH_3)CH(CH_3)CH_2O—CH_2OCH_3$ |
| 1447. | $N(CH_2OCH_3)CH(CH_2CH_3)CH_2OH$ |
| 1448. | $N(CH_2OCH_3)CH(CH_2CH_3)—CH_2OCH_3$ |
| 1449. | $N(CH_2OCH_3)CH(CH_2CH_3)CH_2O—CH_2CH_3$ |
| 1450. | $N(CH_2OCH_3)CH(CH_2CH_3)CH_2O—(CH_2)_2CH_3$ |
| 1451. | $N(CH_2OCH_3)CH(CH_2CH_3)CH_2O—CH(CH_3)_2$ |
| 1452. | $N(CH_2OCH_3)CH(CH_2CH_3)CH_2O—CH_2OCH_3$ |
| 1453. | $N(CH_2OCH_3)CH(CH_2CH)CH_2OH$ |
| 1454. | $N(CH_2OCH_3)CH(CH_2CH)—CH_2OCH_3$ |
| 1455. | $N(CH_2OCH_3)CH(CH_2CH)CH_2O—CH_2CH_3$ |
| 1456. | $N(CH_2OCH_3)CH(CH_2CH)CH_2O—(CH_2)_2CH_3$ |
| 1457. | $N(CH_2OCH_3)CH(CH_2CH)CH_2O—CH(CH_3)_2$ |
| 1458. | $N(CH_2OCH_3)CH(CH_2CH)CH_2O—CH_2OCH_3$ |
| 1459. | $N(CH_2OCH_3)CH(CH_2OCH_3)—CH_2OH$ |
| 1460. | $N(CH_2OCH_3)CH(CH_2OCH_3)CH_2O—CH_3$ |
| 1461. | $N(CH_2OCH_3)CH(CH_2OCH_3)CH_2O—CH_2CH_3$ |
| 1462. | $N(CH_2OCH_3)CH(CH_2OCH_3)CH_2O—(CH_2)_2CH_3$ |
| 1463. | $N(CH_2OCH_3)CH(CH_2OCH_3)CH_2O—CH(CH_3)_2$ |
| 1464. | $N(CH_2OCH_3)CH(CH_2OCH_3)CH_2O—CH_2OCH_3$ |
| 1465. | $N(CH_2OCH_3)CH_2CH(CH_3)OH$ |
| 1466. | $N(CH_2OCH_3)CH_2CH(CH_3)OCH_3$ |
| 1467. | $N(CH_2OCH_3)CH_2CH(CH_3)O—CH_2CH_3$ |
| 1468. | $N(CH_2OCH_3)CH_2CH(CH_3)O—(CH_2)_2CH_3$ |
| 1469. | $N(CH_2OCH_3)CH_2CH(CH_3)O—CH(CH_3)_2$ |
| 1470. | $N(CH_2OCH_3)CH_2CH(CH_3)O—CH_2OCH_3$ |
| 1471. | $N(CH_2OCH_3)CH_2CH(CH_2CH_3)OH$ |
| 1472. | $N(CH_2OCH_3)CH_2CH(CH_2CH_3)—OCH_3$ |
| 1473. | $N(CH_2OCH_3)CH_2CH(CH_2CH_3)O—CH_2CH_3$ |
| 1474. | $N(CH_2OCH_3)CH_2CH(CH_2CH_3)O—(CH_2)_2CH_3$ |

TABLE A-continued

| No. | R6 |
|---|---|
| 1475. | N(CH$_2$OCH$_3$)CH$_2$CH(CH$_2$CH$_3$)O—CH(CH$_3$)$_2$ |
| 1476. | N(CH$_2$OCH$_3$)CH$_2$CH(CH$_2$CH$_3$)O—CH$_2$OCH$_3$ |
| 1477. | N(CH$_2$OCH$_3$)CH$_2$CH(CH$_2$CH)OH |
| 1478. | N(CH$_2$OCH$_3$)CH$_2$CH(CH$_2$CH)—OCH$_3$ |
| 1479. | N(CH$_2$OCH$_3$)CH$_2$CH(CH$_2$CH)O—CH$_2$CH$_3$ |
| 1480. | N(CH$_2$OCH$_3$)CH$_2$CH(CH$_2$CH)—(CH$_2$CH)O—(CH$_2$)$_2$CH$_3$ |
| 1481. | N(CH$_2$OCH$_3$)CH$_2$CH(CH$_2$CH)—OCH(CH$_3$)$_2$ |
| 1482. | N(CH$_2$OCH$_3$)CH$_2$CH(CH$_2$CH)O—CH$_2$OCH$_3$ |
| 1483. | N(CH$_2$OCH$_3$)CH$_2$CH(CH$_2$OCH$_3$)—OH |
| 1484. | N(CH$_2$OCH$_3$)CH$_2$CH(CH$_2$OCH$_3$)O—CH$_3$ |
| 1485. | N(CH$_2$OCH$_3$)CH$_2$CH(CH$_2$OCH$_3$)O—CH$_2$CH$_3$ |
| 1486. | N(CH$_2$OCH$_3$)CH$_2$CH(CH$_2$OCH$_3$)O—(CH$_2$)$_2$CH$_3$ |
| 1487. | N(CH$_2$OCH$_3$)CH$_2$CH(CH$_2$OCH$_3$)O—CH(CH$_3$)$_2$ |
| 1488. | N(CH$_2$OCH$_3$)CH$_2$CH(CH$_2$OCH$_3$)O—CH$_2$OCH$_3$ |
| 1489. | N(CH$_2$OCH$_3$)CH(CH$_3$)CH$_2$CH$_2$OH |
| 1490. | N(CH$_2$OCH$_3$)CH(CH$_3$)—CH$_2$CH$_2$OCH$_3$ |
| 1491. | N(CH$_2$OCH$_3$)CH(CH$_3$)CH$_2$CH$_2$O—CH$_2$CH$_3$ |
| 1492. | N(CH$_2$OCH$_3$)CH(CH$_3$)CH$_2$CH$_2$O—(CH$_2$)$_2$CH$_3$ |
| 1493. | N(CH$_2$OCH$_3$)CH(CH$_3$)CH$_2$CH$_2$O—CH(CH$_3$)$_2$ |
| 1494. | N(CH$_2$OCH$_3$)CH(CH$_3$)CH$_2$CH$_2$O—CH$_2$OCH$_3$ |
| 1495. | N(CH$_2$OCH$_3$)CH(CH$_2$CH$_3$)—CH$_2$CH$_2$OH |
| 1496. | N(CH$_2$OCH$_3$)CH(CH$_2$CH$_3$)—CH$_2$CH$_2$OCH$_3$ |
| 1497. | N(CH$_2$OCH$_3$)CH(CH$_2$CH$_3$)—CH$_2$CH$_2$OCH$_2$CH$_3$ |
| 1498. | N(CH$_2$OCH$_3$)CH(CH$_2$CH$_3$)—CH$_2$CH$_2$O(CH$_2$)$_2$CH$_3$ |
| 1499. | N(CH$_2$OCH$_3$)CH(CH$_2$CH$_3$)—CH$_2$CH$_2$OCH(CH$_3$)$_2$ |
| 1500. | N(CH$_2$OCH$_3$)CH(CH$_2$CH$_3$)—CH$_2$CH$_2$OCH$_2$OCH$_3$ |
| 1501. | N(CH$_2$OCH$_3$)C[(CH$_3$)$_2$]CH$_2$CH$_2$OH |
| 1502. | N(CH$_2$OCH$_3$)C[(CH$_3$)$_2$—CH$_2$CH$_2$OCH$_3$ |
| 1503. | N(CH$_2$OCH$_3$)C[(CH$_3$)$_2$]CH$_2$CH$_2$O—CH$_2$CH$_3$ |
| 1504. | N(CH$_2$OCH$_3$)C[(CH$_3$)$_2$]CH$_2$CH$_2$O—(CH$_2$)$_2$CH$_3$ |
| 1505. | N(CH$_2$OCH$_3$)C[(CH$_3$)$_2$]CH$_2$CH$_2$O—CH(CH$_3$)$_2$ |
| 1506. | N(CH$_2$OCH$_3$)C[(CH$_3$)$_2$]CH$_2$CH$_2$O—CH$_2$OCH$_3$ |
| 1507. | N(CH$_2$OCH$_3$)CH(CH$_2$CH)—CH$_2$CH$_2$OH |
| 1508. | N(CH$_2$OCH$_3$)CH(CH$_2$CH)—CH$_2$CH$_2$OCH$_3$ |
| 1509. | N(CH$_2$OCH$_3$)CH(CH$_2$CH)—CH$_2$CH$_2$OCH$_2$CH$_3$ |
| 1510. | N(CH$_2$OCH$_3$)CH(CH$_2$CH)—CH$_2$CH$_2$O(CH$_2$)$_2$CH$_3$ |
| 1511. | N(CH$_2$OCH$_3$)CH(CH$_2$CH)—CH$_2$CH$_2$OCH(CH$_3$)$_2$ |
| 1512. | N(CH$_2$OCH$_3$)CH(CH$_2$CH)—CH$_2$CH$_2$OCH$_2$OCH$_3$ |
| 1513. | N(CH$_2$OCH$_3$)CH(CH$_2$OCH$_3$)—CH$_2$CH$_2$OH |
| 1514. | N(CH$_2$OCH$_3$)CH(CH$_2$OCH$_3$)—CH$_2$CH$_2$OCH$_3$ |
| 1515. | N(CH$_2$OCH$_3$)CH(CH$_2$OCH$_3$)—CH$_2$CH$_2$OCH$_2$CH$_3$ |
| 1516. | N(CH$_2$OCH$_3$)CH(CH$_2$OCH$_3$)—CH$_2$CH$_2$O(CH$_2$)$_2$CH$_3$ |
| 1517. | N(CH$_2$OCH$_3$)CH(CH$_2$OCH$_3$)—CH$_2$CH$_2$OCH(CH$_3$)$_2$ |
| 1518. | N(CH$_2$OCH$_3$)CH(CH$_2$OCH$_3$)—CH$_2$CH$_2$OCH$_2$OCH$_3$ |
| 1519. | NHCH$_2$CH(OCH$_3$)$_2$ |
| 1520. | NHCH$_2$CH(OCH$_2$CH$_3$)$_2$ |
| 1521. | NHCH(CH$_3$)CH(OCH$_3$)$_2$ |
| 1522. | NHCH(CH$_3$)CH(OCH$_2$CH$_3$)$_2$ |
| 1523. | NHCH(CH$_2$CH$_3$)CH(OCH$_3$)$_2$ |
| 1524. | NHCH(CH$_2$CH$_3$)CH(OCH$_2$CH$_3$)$_2$ |
| 1525. | NHCH(CH$_2$CH$_2$CH$_3$)CH(OCH$_3$)$_2$ |
| 1526. | NHCH(CH$_2$CH$_2$CH$_3$)-CH(OCH$_2$CH$_3$)$_2$ |
| 1527. | NHCH$_2$CH$_2$CH(OCH$_3$)$_2$ |
| 1528. | NHCH$_2$CH$_2$CH(OCH$_2$CH$_3$)$_2$ |
| 1529. | NHCH(CH$_3$)CH$_2$CH(OCH$_3$)$_2$ |
| 1530. | NHCH(CH$_3$)CH$_2$CH(OCH$_2$CH$_3$)$_2$ |
| 1531. | NHCH(CH$_2$CH$_3$)CH$_2$CH(OCH$_3$)$_2$ |
| 1532. | NHCH(CH$_2$CH$_3$)-CH$_2$CH(OCH$_2$CH$_3$)$_2$ |
| 1533. | NHCH(CH$_2$CH$_2$CH$_3$)—CH$_2$CH(OCH$_3$)$_2$ |
| 1534. | NHCH(CH$_2$CH$_2$CH$_3$)—CH$_2$CH(OCH$_2$CH$_3$)$_2$ |
| 1535. | NHCH$_2$C(CH$_3$)(OCH$_3$)$_2$ |
| 1536. | NHCH$_2$C(CH$_3$)(OCH$_2$CH$_3$)$_2$ |
| 1537. | NHCH(CH$_3$)C (CH$_3$)(OCH$_3$)$_2$ |
| 1538. | NHCH(CH$_3$)C(CH$_3$)(OCH$_2$CH$_3$)$_2$ |
| 1539. | NHCH(CH$_2$CH$_3$)C(CH$_3$)(OCH$_3$)$_2$ |
| 1540. | NHCH(CH$_2$CH$_3$)-C(CH$_3$)(OCH$_2$CH$_3$)$_2$ |
| 1541. | NHCH(CH$_2$CH$_2$CH$_3$)-C(CH$_3$)(OCH$_3$)$_2$ |
| 1542. | NHCH(CH$_2$CH$_2$CH$_3$)—C(CH$_3$)(OCH$_2$CH$_3$)$_2$ |
| 1543. | NHCH$_2$CH$_2$C(CH$_3$)(OCH$_3$)$_2$ |
| 1544. | NHCH$_2$CH$_2$C(CH$_3$)(OCH$_2$CH$_3$)$_2$ |
| 1545. | NNCH(CH$_3$)CH$_2$C(CH$_3$)(OCH$_3$)$_2$ |
| 1546. | NHCH(CH$_3$)—CH$_2$C(CH$_3$)(OCH$_2$CH$_3$)$_2$ |
| 1547. | NHCH(CH$_2$CH$_3$)—CH$_2$C(CH$_3$)(OCH$_3$)$_2$ |
| 1548. | NHCH(CH$_2$CH$_3$)—CH$_2$C(CH$_3$)(OCH$_2$CH$_3$)$_2$ |
| 1549. | NHCH(CH$_2$CH$_2$CH$_3$)—CH$_2$C(CH$_3$)(OCH$_3$)$_2$ |
| 1550. | NHCH(CH$_2$CH$_2$CH$_3$) —CH$_2$C(CH$_3$)(OCH$_2$CH$_3$)$_2$ |
| 1551. | NHCH$_2$CH(SCH$_3$)$_2$ |
| 1552. | NHCH$_2$CH(SCH$_2$CH$_3$)$_2$ |
| 1553. | NHCH(CH$_3$)CH(SCH$_3$)$_2$ |
| 1554. | NHCH(CH$_3$)CH(SCH$_2$CH$_3$)$_2$ |
| 1555. | NHCH(CH$_2$CH$_3$)CH(SCH$_3$)$_2$ |
| 1556. | NHCH(CH$_2$CH$_3$)CH(SCH$_2$CH$_3$)$_2$ |
| 1557. | NHCH(CH$_2$CH$_2$CH$_3$)CH(SCH$_3$)$_2$ |
| 1558. | NHCH(CH$_2$CH$_2$CH$_3$)—CH(SCH$_2$CH$_3$)$_2$ |
| 1559. | NHCH$_2$CH$_2$CH(SCH$_3$)$_2$ |
| 1560. | NHCH$_2$CH$_2$CH(SCH$_2$CH$_3$)$_2$ |
| 1561. | NHCH(CH$_3$)CH$_2$CH(SCH$_3$)$_2$ |
| 1562. | NHCH(CH$_3$)CH$_2$CH(SCH$_2$CH$_3$)$_2$ |
| 1563. | NHCH(CH$_2$CH$_3$)CH$_2$CH(SCH$_3$)$_2$ |
| 1564. | NHCH(CH$_2$CH$_3$)—CH$_2$CH(SCH$_2$CH$_3$)$_2$ |
| 1565. | NHCH(CH$_2$CH$_2$CH$_3$)—CH$_2$CH(SCH$_3$)$_2$ |
| 1566. | NHCH(CH$_2$CH$_2$CH$_3$) —CH$_2$CH(SCH$_2$CH$_3$)$_2$ |
| 1567. | NHCH$_2$CH$_2$SCH$_3$ |
| 1568. | NHCH$_2$CH$_2$SCH$_2$CH$_3$ |
| 1569. | NHCH$_2$CH$_2$S(CH$_2$)$_2$CH$_3$ |
| 1570. | NHCH$_2$CH$_2$SCH(CH$_3$)$_2$ |
| 1571. | NHCH$_2$CH$_2$CH$_2$SCH$_3$ |
| 1572. | NHCH$_2$CH$_2$CH$_2$SCH$_2$CH$_3$ |
| 1573. | NKCH$_2$CH$_2$CH$_2$S(CH$_2$)$_2$CH$_3$ |
| 1574. | NHCH$_2$CH$_2$CH$_2$SCH(CH$_3$)$_2$ |
| 1575. | NHCH(CH$_3$)CH$_2$SCH$_3$ |
| 1576. | NHCH(CH$_3$)CH$_2$SCH$_2$CH$_3$ |
| 1577. | NHCH(CH$_3$)CH$_2$S(CH$_2$)$_2$CH$_3$ |
| 1578. | NHCH(CH$_3$)CH$_2$SCH(CH$_3$)$_2$ |
| 1579. | NHCH(CH$_3$)CH$_2$CH$_2$SCH$_3$ |
| 1580. | NHCH(CH$_3$)CH$_2$CH$_2$SCH$_2$CH$_3$ |
| 1581. | NHCH(CH$_3$)CH$_2$CH$_2$S(CH$_2$)$_2$CH$_3$ |
| 1582. | NHCH(CH$_3$)CH$_2$CH$_2$SCH(CH$_3$)$_2$ |
| 1583. | NHC[(CH$_3$)$_2$]CH$_2$SCH$_3$ |

TABLE A-continued

| No. | R6 |
|---|---|
| 1584. | NHC[(CH₃)₂]CH₂SCH₂CH₃ |
| 1585. | NHC[(CH₃)₂]CH₂S(CH₂)₂CH₃ |
| 1586. | NHC[(CH₃)₂]CH₂SCH(CH₃)₂ |
| 1587. | NHC[(CH₃)₂]CH₂CH₂SCH₃ |
| 1588. | NHC[(CH₃)₂]CH₂CH₂SCH₂CH₃ |
| 1589. | NHC[(CH₃)₂]CH₂CH₂S(CH₂)₂CH₃ |
| 1590. | NHC[(CH₃)₂]CH₂CH₂SCH(CH₃)₂ |
| 1591. | NHCH₂CH₂S(O)CH₃ |
| 1592. | NHCH₂CH₂S(O)CH₂CH₃ |
| 1593. | NHCH₂CH₂S(O)(CH₂)₂CH₃ |
| 1594. | NHCH₂CH₂S(O)CH(CH₃)₂ |
| 1595. | NHCH₂CH₂CH₂S(O)CH₃ |
| 1596. | NHCH₂CH₂CH₂S(O)CH₂CH₃ |
| 1597. | NHCH₂CH₂CH₂S(O)(CH₂)₂CH₃ |
| 1598. | NHCH₂CH₂CH₂S(O)CH(CH₃)₂ |
| 1599. | NHCH(CH₃)CH₂S(O)CH₃ |
| 1600. | NHCH(CH₃)CH₂S(O)CH₂CH₃ |
| 1601. | NHCH(CH₃)CH₂S(O)(CH₂)₂CH₃ |
| 1602. | NHCH(CH₃)CH₂S(O)CH(CH₃)₂ |
| 1603. | NHCH(CH₃)CH₂CH₂S(O)CH₃ |
| 1604. | NHCH(CH₃)CH₂CH₂S(O)CH₂CH₃ |
| 1605. | NHCH(CH₃)CH₂CH₂S(O)—(CH₂)₂CH₃ |
| 1606. | NHCH(CH₃)CH₂CH₂S(O)—CH(CH₃)₂ |
| 1607. | NHC[(CH₃)₂]CH₂S(O)CH₃ |
| 1608. | NHC[(CH₃)₂3CH₂S(O)CH₂CH₃ |
| 1609. | NHC[(CH₃)₂]CH₂S(O)(CH₂)₂CH₃ |
| 1610. | NHC[(CH₃)₂]CH₂S(O)CH(CH₃)₂ |
| 1611. | NHC[(CH₃)₂]CH₂CH₂S(O)CH₃ |
| 1612. | NHC[(CH₃)₂]CH₂CH₂S(O)CH₂CH₃ |
| 1613. | NHC[(CH₃)₂]CH₂CH₂S(O)—(CH₂)₂CH₃ |
| 1614. | NHC[(CH₃)₂]CH₂CH₂S(O)—CH(CH₃)₂ |
| 1615. | NHCH₂CH₂S(O)₂CH₃ |
| 1616. | NHCH₂CH₂S(O)₂CH₂CH₃ |
| 1617. | NHCH₂CH₂S(O)2(CH₂)₂CH₃ |
| 1618. | NHCH₂CH₂S(O)₂CH(CH₃)₂ |
| 1619. | NHCH₂CH₂CH₂S(O)₂CH₃ |
| 1620. | NHCH₂CH₂CH₂S(O)₂CH₂CH₃ |
| 1621. | NHCH₂CH₂CH₂S(O)₂(CH₂)₂CH₃ |
| 1622. | NHCH₂CH₂CH₂S(O)₂CH(CH₃)₂ |
| 1623. | NHCH(CH₃)CH₂S(O)₂CH₃ |
| 1624. | NHCH(CH₃)CH₂S(O)₂CH₂CH₃ |
| 1625. | NHCH(CH₃)CH₂S(O)₂(CH₂)₂CH₃ |
| 1626. | NHCH(CH₃)CH₂S(O)₂CH(CH₃)₂ |
| 1627. | NHCH(CH₃)CH₂CH₂S(O)₂CH₃ |
| 1628. | NHCH(CH₃)CH₂CH₂S(O)₂CH₂CH₃ |
| 1629. | NHCH(CH₃)CH₂CH₂S(O)₂—(CH₂)₂CH₃ |
| 1630. | NHCH(CH₃)CH₂CH₂S(O)₂CH(CH₃)₂ |
| 1631. | NHC[(CH₃)₂]CH₂S(O)₂CH₃ |
| 1632. | NHC[(CH₃)₂]CH₂S(O)₂CH₂CH₃ |
| 1633. | NHC[(CH₃)₂]CH₂S(O)₂(CH₂)₂CH₃ |
| 1634. | NHC[(CH₃)2JCH₂S(O)₂CH(CH₃)₂ |
| 1635. | NHC[(CH₃)₂]CH₂CH₂S(O)₂CH₃ |
| 1636. | NHC[(CH₃)₂]CH₂CH₂S(O)₂—CH₂CH₃ |
| 1637. | NHC[(CH₃)₂]CH₂CH₂S(O)₂—(CH₂)₂CH₃ |
| 1638. | NHC[(CH₃)₂]CH₂CH₂S(O)₂—CH(CH₃)₂ |
| 1639. | NHCH₂CH₂Si(OCH₃)₃ |
| 1640. | NHCH₂CH₂Si(OCH₂CH₃)₃ |
| 1641. | NHCH(CH₃)CH₂Si(OCH₃)₃ |
| 1642. | NHCH(CH₃)CH₂Si(OCH₂CH₃)₃ |
| 1643. | NHCH₂CH₂CH₂Si(OCH₃)₃ |
| 1644. | NHCH₂CH₂CH₂Si(OCH₂CH₃)₃ |
| 1645. | NHCH(CH₃)CH₂CH₂Si(OCH₃)₃ |
| 1646. | NHCH(CH₃)CH₂CH2-Si(OCH₂CH₃)₃ |
| 1647. | 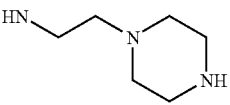 |
| 1648. |  |
| 1649. | 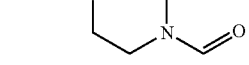 |
| 1650. | 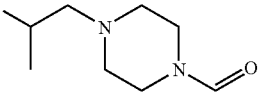 |
| 1651. | 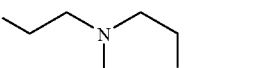 |
| 1652. | 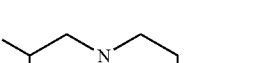 |
| 1653. | 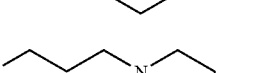 |
| 1654. | 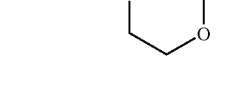 |
| 1655. | 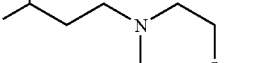 |
| 1656. | 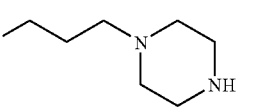 |
| 1657. |  |
| 1658. | 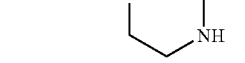 |
| 1659. | 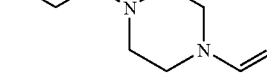 |
| 1660. | 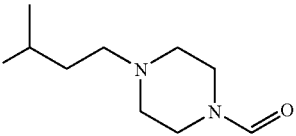 |

TABLE A-continued

| No. | R6 |
|---|---|
| 1661. | HN-CH(CH3)-(tetrahydrofuran-2-yl) |
| 1662. | HN-C(CH3)2-(tetrahydrofuran-2-yl) |
| 1663. | HN-CH(CH3)-(2,3-dihydrofuran-2-yl) |
| 1664. | HN-CH2-(tetrahydrofuran-3-yl) |
| 1665. | HN-CH(CH3)-(tetrahydrofuran-3-yl) |
| 1666. | HN-CH2CH2-(tetrahydrofuran-3-yl) |
| 1667. | HN-CH(CH3)CH2-(tetrahydrofuran-3-yl) |
| 1668. | HN-CH2CH2-(tetrahydrofuran-2-yl) |
| 1669. | HN-CH(CH3)-CH2-(tetrahydrofuran-2-yl) |
| 1670. | HN-CH2-(pyrrolidin-3-yl) |
| 1671. | HN-CH(CH3)-(pyrrolidin-3-yl) |
| 1672. | HN-CH2CH2-(pyrrolidin-3-yl) |
| 1673. | HN-CH(CH3)CH2-(pyrrolidin-3-yl) |
| 1674. | NH-CH2-(tetrahydropyran-4-yl) |
| 1675. | NH-CH(CH3)-(tetrahydropyran-4-yl) |
| 1676. | HN-CH2CH2-(tetrahydropyran-4-yl) |
| 1677. | HN-CH(CH3)CH2-(tetrahydropyran-4-yl) |
| 1678. | HN-(tetrahydrofuran-2-yl) |
| 1679. | HN-(tetrahydrofuran-3-yl) |
| 1680. | HN-(pyrrolidin-3-yl) |
| 1681. | HN-(tetrahydropyran-4-yl) |
| 1682. | HNCH$_2$N=C(NH$_2$)NH$_2$ |
| 1683. | HNCH$_2$CH$_2$N=C(NH$_2$)NH$_2$ |
| 1684. | HNCH$_2$CH$_2$CH$_2$N=C(NH$_2$)NH$_2$ |
| 1685. | HNCH(CH$_3$)N=C(NH$_2$)NH$_2$ |
| 1686. | HNCH(CH$_3$)CH$_2$N=C(NH$_2$)NH$_2$ |
| 1687. | HNCH(CH$_3$)CH$_2$CH$_2$N=C(NH$_2$)NH$_2$ |
| 1688. | HNCH$_2$CH(CH$_3$)N=C(NH$_2$)NH$_2$ |
| 1689. | HNCH$_2$CH$_2$CH(CH$_3$)N=C(NH$_2$)NH$_2$ |
| 1690. | HNCH(CH$_3$)CH(CH$_3$)—N=C(NH$_2$)NH$_2$ |
| 1691. | HNCH(CH$_3$)CH$_2$CH(CH$_3$)—N=C(NH$_2$)NH$_2$ |
| 1692. | NHCH$_2$-(2-pyridyl) |
| 1693. | NHCH$_2$CH$_2$-(2-pyridyl) |
| 1694. | NHCH$_2$CH$_2$CH$_2$-(2-pyridyl) |
| 1695. | NHCH(CH$_3$)—(2-pyridyl) |
| 1696. | NHCH(CH$_3$)CH$_2$-(2-pyridyl) |
| 1697. | NHCH(CH$_3$)CH$_2$CH$_2$-(2-pyridyl) |
| 1698. | NHCH(CH$_2$CH$_3$)—(2-pyridyl) |
| 1699. | NHCH(CH$_2$CH$_3$)CH$_2$-(2-pyridyl) |
| 1700. | NHCH(CH$_2$CH$_3$)CH$_2$CH$_2$-(2-pyridyl) |
| 1701. | NHCH$_2$CH$_2$O-(2-pyridyl) |
| 1702. | NHCH$_2$CH$_2$CH$_2$O-(2-pyridyl) |
| 1703. | NHCH(CH$_3$)O-(2-pyridyl) |
| 1704. | NHCH(CH$_3$)CH$_2$O-(2-pyridyl) |
| 1705. | NHCH(CH$_3$)CH$_2$CH$_2$O-(2-pyridyl) |
| 1706. | NHCH(CH$_2$CH$_3$)O-(2-pyridyl) |
| 1707. | NHCH(CH$_2$CH$_3$)CH$_2$O-(2-pyridyl) |
| 1708. | NHCH(CH$_2$CH$_3$)CH$_2$CH$_2$O—(2-pyridyl) |
| 1709. | NHCH$_2$-(3-pyridyl) |
| 1710. | NHCH$_2$CH$_2$-(3-pyridyl) |
| 1711. | NHCH$_2$CH$_2$CH$_2$-(3-pyridyl) |
| 1712. | NHCH(CH$_3$)-(3-pyridyl) |
| 1713. | NHCH(CH$_3$)CH$_2$-(3-pyridyl) |
| 1714. | NHCH(CH$_3$)CH$_2$CH$_2$-(3-pyridyl) |
| 1715. | NHCH(CH$_2$CH$_3$)-(3-pyridyl) |
| 1716. | NHCH(CH$_2$CH$_3$)CH$_2$-(3-pyridyl) |

TABLE A-continued

| No. | R6 |
|---|---|
| 1717. | NHCH(CH₂CH₃)CH₂CH-(3-pyridyl) |
| 1718. | NHCH₂CH₂O-(3-pyridyl) |
| 1719. | N HCH₂CH₂CH₂O-(3-pyridyi) |
| 1720. | NHCH(CH₃)O-(3-pyridyl) |
| 1721. | NHCH(CH₃)CH₂O-(3-pyridyl) |
| 1722. | NHCH(CH₃)CH₂CH₂O-(3-pyridyl) |
| 1723. | NHCH(CH₂CH₃)O-(3-pyridyl) |
| 1724. | NHCH(CH₂CH₃)CH₂O-(3-pyridyl) |
| 1725. | NHCH(CH₂CH₃)CH₂CH₂O-(3-pyridyl) |
| 1726. | NHCH₂-(4-pyridyl) |
| 1727. | NHCH₂CH₂-(4-pyridyl) |
| 1728. | NHCH₂CH₂CH₂-(4-pyridyl) |
| 1729. | NHCH(CH₃)—(4-pyridyl) |
| 1730. | NHCH(CH₃)CH₂-(4-pyridyl) |
| 1731. | N HCH(CH₃)CH₂CH₂-(4-pyridyl) |
| 1732. | NHCH(CH₂CH₃)-(4-pyridyl) |
| 1733. | NHCH(CH₂CH₃)CH₂-(4-pyridyl) |
| 1734. | NHCH(CH₂CH₃)CH₂CH₂-(4-pyridyl) |
| 1735. | NHCH₂CH₂O-(4-pyridyl) |
| 1736. | NHCH₂CH₂CH₂O-(4-pyridyl) |
| 1737. | NHCH(CH₃)O-(4-pyridyl) |
| 1738. | NHCH(CH₃)CH₂O-(4-pyridyl) |
| 1739. | NHCH(CH₃)CH₂CH₂O-(4-pyridyl) |
| 1740. | NHCH(CH₂CH₃)O-(4-pyridyl) |
| 1741. | NHCH(CH₂CH₃)CH₂O-(4-pyridyl) |
| 1742. | NHCH(CH₂CH₃)CH₂CH₂O-(4-pyridyl) |
| 1743. | NHCH₂-(2-pyrimidyl) |
| 1744. | NHCH₂CH₂-(2-pyrimidyl) |
| 1745. | NHCH₂CH₂CH₂-(2-pyrimidyl) |
| 1746. | NHCH(CH₃)-(2-pyrimidyl) |
| 1747. | NHCH(CH₃)CH₂-(2-pyrimidyl) |
| 1748. | NHCH(CH₃)CH₂CH₂-(2-pyrimidyl) |
| 1749. | NHCH(CH₂CH₃)-(2-pyrimidyl) |
| 1750. | NHCH(CH₂CH₃)CH₂-(2-pyrimidyl) |
| 1751. | NHCH(CH₂CH₃)CH₂CH₂-(2-pyrimidyl) |
| 1752. | NHCH₂CH₂O-(2-pyrimidyl) |
| 1753. | NHCH₂CH₂CH₂O-(2-pyrimidyl) |
| 1754. | NHCH(CH₃)O-(2-pyrimidyl) |
| 1755. | NHCH(CH₃)CH₂O-(2-pyrimidyl) |
| 1756. | NHCH(CH₃)CH₂CH₂O-(2-pyrimidyl) |
| 1757. | NHCH(CH₂CH₃)O-(2-pyrimidyl) |
| 1758. | NHCH(CH₂CH₃)CH₂O-(2-pyrimidyl) |
| 1759. | NHCH(CH₂CH₃)CH₂CH₂O-(2-pyrimidyl) |
| 1760. | NHCH₂-(4-pyrimidyl) |
| 1761. | NHCH₂CH₂-(4-pyrimidyl) |
| 1762. | NHCH₂CH₂CH₂-(4-pyrimidyl) |
| 1763. | NHCH(CH₃)-(4-pyrimidyl) |
| 1764. | NHCH(CH₃)CH₂-(4-pyrimidyl) |
| 1765. | NHCH(CH₃)CH₂CH₂-(4-pyrimidyl) |
| 1766. | NHCH(CH₂CH₃)-(4-pyrimidyl) |
| 1767. | NHCH(CH₂CH₃)CH₂-(4-pyrimidyl) |
| 1768. | NHCH(CH₂CH₃)CH₂CH₂-(4-pyrimidyl) |
| 1769. | NHCH₂CH₂O-(4-pyrimidyl) |
| 1770. | NHCH₂CH₂CH₂O-(4-pyrimidyl) |
| 1771. | NHCH(CH₃)O-(4-pyrimidyl) |
| 1772. | NHCH(CH₃)CH₂O-(4-pyrimidyl) |
| 1773. | NHCH(CH₃)CH₂CH₂O-(4-pyrimidyl) |
| 1774. | NHCH(CH₂CH₃)O-(4-pyrimidyl) |
| 1775. | NHCH(CH₂CH₃)CH₂O-(4-pyrimidyl) |
| 1776. | NHCH(CH₂CH₃)CH₂CH₂O-(4-pyrimidyl) |
| 1777. | NHCH₂-(5-pyrimidyl) |
| 1778. | NHCH₂CH₂-(5-pyrimidyl) |
| 1779. | NHCH₂CH₂CH₂-(5-pyrimidyl) |
| 1780. | NHCH(CH₃)-(5-pyrimidyl) |
| 1781. | NHCH(CH₃)CH₂-(5-pyrimidyl) |
| 1782. | NHCH(CH₃)CH₂CH₂-(5-pyrimidyl) |
| 1783. | NHCH(CH₂CH₃)—(5-pyrimidyl) |
| 1784. | NHCH(CH₂CH₃)CH₂-(5-pyrimidyl) |
| 1785. | NHCH(CH₂CH₃)CH₂CH₂-(5-pyrimidyl) |
| 1786. | NHCH₂CH₂O-(5-pyrimidyl) |
| 1787. | NHCH₂CH₂CH₂O-(5-pyrimidyl) |
| 1788. | NHCH(CH₃)O-(5-pyrimidyl) |
| 1789. | NHCH(CH₃)CH₂O-(5-pyrimidyl) |
| 1790. | NHCH(CH₃)CH₂CH₂O-(5-pyrimidyl) |
| 1791. | NHCH(CH₂CH₃)O-(5-pyrimidyl) |
| 1792. | NHCH(CH₂CH₃)CH₂O-(5-pyrimidyl) |
| 1793. | NHCH(CH₂CH₃)CH₂CH₂O-(5-pyrimidyl) |
| 1794. | NHCH₂-(1,3,5-triazinyl) |
| 1795. | NHCH₂CH₂-(1,3,5-triazinyl) |
| 1796. | NHCH₂CH₂CH₂-(1,3,5-triazinyl) |
| 1797. | NHCH(CH₃)—(1,3,5-triazinyl) |
| 1798. | NHCH(CH₃)CH₂-(1,3,5-triazinyl) |
| 1799. | NHCH(CH₃)CH₂CH₂-(1,3,5-triazinyl) |
| 1800. | NHCH(CH₂CH₃)-(1,3,5-triazinyl) |
| 1801. | NHCH(CH₂CH₃)CH₂-(1,3,5-triazinyl) |
| 1802. | NHCH(CH₂CH₃)CH₂CH₂-(1,3,5-triazinyl) |
| 1803. | NHCH₂CH₂O-(1,3,5-triazinyl) |
| 1804. | NHCH₂CH₂CH₂O-(1,3,5-triazinyl) |
| 1805. | NHCH(CH₃)O-(1,3,5-triazinyl) |
| 1806. | NHCH(CH₃)CH₂O-(1,3,5-triazinyl) |
| 1807. | NHCH(CH₃)CH₂CH₂O-(1,3,5-triazinyl) |
| 1808. | NHCH(CH₂CH₃)O-(1,3,5-triazinyl) |
| 1809. | NHCH(CH₂CH₃)CH₂O-(1,3,5-triazinyl) |
| 1810. | NHCH(CH₂CH₃)CH₂CH₂O-(1,3,5-triazinyl) |
| 1811. | NHCH₂-(2-thiazolyl) |
| 1812. | NHCH₂CH₂-(2-thiazolyl) |
| 1813. | NHCH₂CH₂CH₂-(2-thiazolyl) |
| 1814. | NHCH(CH₃)-(2-thiazolyl) |
| 1815. | NHCH(CH₃)CH₂-(2-thiazolyl) |
| 1816. | NHCH(CH₃)CH₂CH₂-(2-thiazolyl) |
| 1817. | NHCH(CH₂CHs)—(2-thiazolyl) |
| 1818. | NHCH(CH₂CH₃)CH₂-(2-thiazolyl) |
| 1819. | NHCH(CH₂CH₃)CH₂CH₂-(2-thiazolyl) |
| 1820. | NHCH₂CH₂O-(2-thiazolyl) |
| 1821. | NHCH₂CH₂CH₂O-(2-thiazolyl) |
| 1822. | NHCH(CH₃)O-(2-thiazolyl) |
| 1823. | NHCH(CH₃)CH₂O-(2-thiazolyl) |
| 1824. | NHCH(CH₃)CH₂CH₂O-(2-thiazolyl) |
| 1825. | NHCH(CH₂CH₃)O-(2-thiazolyl) |
| 1826. | NHCH(CH₂CH₃)CH₂O-(2-thiazolyl) |
| 1827. | NHCH(CH₂CH₃)CH₂CH₂O-(2-thiazolyl) |
| 1828. | NHCH₂-(4-thiazolyl) |
| 1829. | NHCH₂CH₂-(4-thiazolyl) |
| 1830. | NHCH₂CHaCH₂-(4-thiazolyl) |
| 1831. | NHCH(CH₃)-(4-thiazolyl) |
| 1832. | NHCH(CH₃)CH₂-(4-thiazolyl) |
| 1833. | NHCH(CH₃)CH₂CH₂-(4-thiazolyl) |
| 1834. | NHCH(CH₂CH₃)—(4-thiazolyl) |
| 1835. | NHCH(CH₂CH₃)CH₂-(4-thiazolyl) |
| 1836. | NHCH(C H₂CH₃)CH₂CH₂-(4-thiazolyl) |
| 1837. | NHCH₂CH₂O-(4-thiazolyl) |
| 1838. | NHCH₂CH₂CH₂O-(4-thiazolyl) |
| 1839. | NHCH(CH₃)O-(4-thiazolyl) |
| 1840. | NHCH(CH₃)CH₂O-(4-thiazolyl) |
| 1841. | NHCH(CH₃)CH₂CH₂O-(4-thiazolyl) |
| 1842. | NHCH(CH₂CH₃)O-(4-thiazolyl) |
| 1843. | NHCH(CH₂CH₃)CH₂O-(4-thiazolyl) |
| 1844. | NHCH(CH₂CH₃)CH₂CH₂O-(4-thiazolyl) |
| 1845. | NHCH₂-(5-thiazolyl) |
| 1846. | NHCH₂CH₂-(5-thiazolyl) |
| 1847. | NHCH₂CH₂CH₂-(5-thiazolyl) |
| 1848. | NHCH(CH₃)-(5-thiazolyl) |
| 1849. | NHCH(CH₃)CH₂-(5-thiazolyl) |

TABLE A-continued

| No. | R6 |
|---|---|
| 1850. | NHCH(CH₃)CH₂CH₂-(5-thiazolyl) |
| 1851. | NHCH(CH₂CH₃)-(5-thiazolyl) |
| 1852. | NHCH(CH₂CH₃)CH₂-(5-thiazolyl) |
| 1853. | NHCH(CH₂CH₃)CH₂CH₂-(5-thiazolyl) |
| 1854. | NHCH₂CH₂O-(5-thiazolyl) |
| 1855. | NHCH₂CH₂CH₂O-(5-thiazolyl) |
| 1856. | NHCH(CH₃)O-(5-thiazolyl) |
| 1857. | NHCH(CH₃)CH₂O-(5-thiazolyl) |
| 1858. | NHCH(CH₃)CH₂CH₂O-(5-thiazolyl) |
| 1859. | NHCH(CH₂CH₃)O-(5-thiazolyl) |
| 1860. | NHCH(CH₂CH₃)CH₂O-(5-thiazolyl) |
| 1861. | NHCH(CH₂CH₃)CH₂CH₂O-(5-thiazolyl) |
| 1862. | NHCH₂-(2-furyl) |
| 1863. | NHCH₂CH₂-(2-furyl) |
| 1864. | NHCH₂CH₂CH₂-(2-furyl) |
| 1865. | NHCH(CH₃)—(2-furyl) |
| 1866. | NHCH(CH₃)CH₂-(2-furyl) |
| 1867. | NHCH(CH₃)CH₂CH₂-(2-furyl) |
| 1868. | NHCH(CH₂CH₃)-(2-furyl) |
| 1869. | NHCH(CH₂CH₃)CH₂-(2-furyl) |
| 1870. | NHCH(CH₂CH₃)CH₂CH₂-(2-furyl) |
| 1871. | NHCH₂CH₂O-(2-furyl) |
| 1872. | NHCH₂CH₂CH₂O-(2-furyl) |
| 1873. | NHCH(CH₃)O-(2-furyl) |
| 1874. | NHCH(CH₃)CH₂O-(2-furyl) |
| 1875. | NHCH(CH₃)CH₂CH₂O-(2-furyl) |
| 1876. | NHCH(CH₂CH₃)O-(2-furyl) |
| 1877. | NHCH(CH₂CH₃)CH₂O-(2-furyl) |
| 1878. | NHCH(CH₂CH₃)CH₂CH₂O-(2-furyl) |
| 1879. | NHCH₂-(3-furyl) |
| 1880. | NHCH₂CH₂-(3-furyl) |
| 1881. | NHCH₂CH₂CH₂-(3-furyl) |
| 1882. | NHCH(CH₃)—(3-furyl) |
| 1883. | NHCH(CH₃)CH₂-(3-furyl) |
| 1884. | NHCH(CH₃)CH₂CH₂-(3-furyl) |
| 1885. | NHCH(CH₂CH₃)—(3-furyl) |
| 1886. | NHCH(CH₂CH₃)CH₂-(3-furyl) |
| 1887. | NHCH(CH₂CH₃)CH₂CH₂-(3-furyl) |
| 1888. | NHCH₂CH₂O-(3-furyl) |
| 1889. | NHCH₂CH₂CH₂O-(3-furyl) |
| 1890. | NHCH(CH₃)O-(3-furyl) |
| 1891. | NHCH(CH₃)CH₂O-(3-furyl) |
| 1892. | NHCH(CH₃)CH₂CH₂O-(3-furyl) |
| 1893. | NHCH(CH₂CHs)O-(3-furyl) |
| 1894. | NHCH(CH₂CH₃)CH₂O-(3-furyl) |
| 1895. | NHCH(CH₂CH₃)CH₂CH₂O-(3-furyl) |
| 1896. | NHCH₂-(2-thienyl) |
| 1897. | NHCH₂CH₂-(2-thienyl) |
| 1898. | NHCH₂CH₂CH₂-(2-thienyl) |
| 1899. | NHCH(CH₃)—(2-thienyl) |
| 1900. | NHCH(CH₃)CH₂-(2-thienyl) |
| 1901. | NHCH(CH₃)CH₂CH₂-(2-thienyl) |
| 1902. | NHCH(CH₂CH₃)—(2-thienyl) |
| 1903. | NHCH(CH₂CH₃)CH₂-(2-thienyl) |
| 1904. | NHCH(CH₂CH₃)CH₂CH₂-(2-thienyl) |
| 1905. | NHCH₂CH₂O-(2-thienyl) |
| 1906. | NHCH₂CH₂CH₂O-(2-thienyl) |
| 1907. | NHCH(CH₃)O-(2-thienyl) |
| 1908. | NHCH(CH₃)CH₂O-(2-thienyl) |
| 1909. | NHCH(CH₃)CH₂CH₂O-(2-thienyl) |
| 1910. | NHCH(CH₂CH₃)O-(2-thienyl) |
| 1911. | NHCH(CH₂CH₃)CH₂O-(2-thienyl) |
| 1912. | NHCH(CH₂CH₃)CH₂CH₂O-(2-thienyl) |
| 1913. | NHCH₂-(3-thienyl) |
| 1914. | NHCH₂CH₂-(3-thienyl) |
| 1915. | NHCH₂CH₂CH₂-(3-thienyl) |
| 1916. | NHCH(CH₃)—(3-thienyl) |
| 1917. | NHCH(CH₃)CH₂-(3-thienyl) |
| 1918. | NHCH(CH₃)CH₂CH₂-(3-thienyl) |
| 1919. | NHCH(CH₂CH₃)—(3-thienyl) |
| 1920. | NHCH(CH₂CH₃)CH₂-(3-thienyl) |
| 1921. | NHCH(CH₂CH₃)CH₂CH₂-(3-thienyl) |
| 1922. | NHCH₂CH₂O-(3-thienyl) |
| 1923. | NHCH₂CH₂CH₂O-(3-thienyl) |
| 1924. | NHCH(CH₃)O-(3-thienyl) |
| 1925. | NHCH(CH₃)CH₂O-(3-thienyl) |
| 1926. | NHCH(CH₃)CH₂CH₂O-(3-thienyl) |
| 1927. | NHCH(CH₂CH₃)O-(3-thienyl) |
| 1928. | NHCH(CH₂CH₃)CH₂O-(3-thienyl) |
| 1929. | NHCH(CH₂CH₃)CH₂CH₂O-(3-thienyl) |
| 1930. | NHCH₂-(1-imidazolyl) |
| 1931. | NHCH₂CH₂-(1-imidazolyl) |
| 1932. | NHCH₂CH₂CH₂-(1-imidazolyl) |
| 1933. | NHCH(CH₃)—(1-imidazolyl) |
| 1934. | NHCH(CH₃)CH₂-(1-imidazolyl) |
| 1935. | NHCH(CH₃)CH₂CH₂-(1-imidazolyl) |
| 1936. | NHCH₂H(CH₃)CH₂-(1-imidazolyl) |
| 1937. | NHCH₂CH₂CH(CH₃)-(1-imidazolyl) |
| 1938. | NHCH(CH₂CH₃)-(1-imidazolyl) |
| 1939. | NHCH(CH₂CH₃)CH₂-(1-imidazolyl) |
| 1940. | NHCH(CH₂CH₃)CH₂CH₂-(1-imidazolyl) |
| 1941. | NHCH₂CH₂O-(1-imidazolyl) |
| 1942. | NHCH₂CH₂CH₂O-(1-imidazolyl) |
| 1943. | NHCH(CH₃)O-(1-imidazolyl) |
| 1944. | NHCH(CH₃)CH₂O-(1-imidazolyl) |
| 1945. | NHCH(CH₃)CH₂CH₂O-(1-imidazolyl) |
| 1946. | NHCH(CH₂CH₃)O-(1-imidazolyl) |
| 1947. | NHCH(CH₂CH₃)CH₂O-(1-imidazolyl) |
| 1948. | NHCH(CH₂CH₃)CH₂CH₂O-(1-imidazolyl) |
| 1949. | NHCH₂-(1-[1,2,4-triazolyl]) |
| 1950. | NHCH₂CH₂-(1-[1,2,4-triazolyl]) |
| 1951. | NHCH₂CH₂CH₂-(1-[1,2,4-triazolyl]) |
| 1952. | NHCH(CH₃)-(1-[1,2,4-triazolyl]) |
| 1953. | NHCH(CH₃)CH₂-(1-[1,2,4-triazolyl]) |
| 1954. | NHCH(CH₃)CH₂CH₂-(1-[1,2,4-triazolyl]) |
| 1955. | NHCH(CH₂CH₃)-(1-[1,2,4-triazolyl]) |
| 1956. | NHCH(CH₂CH₃)CH₂-(1-[1,2,4-triazolyl]) |
| 1957. | NHCH(CH₂CH₃)CH₂CH₂-(1-[1,2,4-triazolyl]) |
| 1958. | NHCH₂CH(CH₃)CH₂-(1-[1,2,4-triazolyl]) |
| 1959. | NHCH₂CH₂CH(CH₃)-(1-[1,2,4-triazolyl]) |
| 1960. | NHCH₂CH₂O-(1-[1,2,4-triazolyl]) |
| 1961. | NHCH₂CH₂CH₂O-(1-[1,2,4-triazolyl]) |
| 1962. | NHCH(CH₃)O-(1-[1,2,4-triazolyl]) |
| 1963. | NHCH(CH₃)CH₂O-(1-[1,2,4-triazolyl]) |
| 1964. | NHCH(CH₃)CH₂CH₂O-(1-[1,2,4-triazolyl]) |
| 1965. | NHCH(CH₂CH₃)O-(1-[1,2,4-triazolyl]) |
| 1966. | NHCH(CH₂CH₃)CH₂O-(1-[1,2,4-triazolyl]) |
| 1967. | NHCH(CH₂CH₃)CH₂CH₂O-(1-[1,2,4-triazolyl]) |
| 1968. | NHCH₂-(1-tetrazolyl) |
| 1969. | NHCH₂CH₂-(1-tetrazolyl) |
| 1970. | NHCH₂CH₂CH₂-(1-tetrazolyl) |
| 1971. | NHCH(CH₃)-(1-tetrazolyl) |
| 1972. | NHCH(CH₃)CH₂-(1-tetrazolyl) |
| 1973. | NHCH(CH₃)CH₂CH₂-(1-tetrazolyl) |
| 1974. | NHCH(CH₂CH₃)—(1-tetrazolyl) |
| 1975. | NHCH(CH₂CH₃)CH₂-(1-tetrazolyl) |
| 1976. | NHCH(CH₂CH₃)CH₂CH₂-(1-tetrazolyl) |
| 1977. | NHCH₂CH₂O-(1-tetrazolyl) |

TABLE A-continued

| No. | R6 |
|---|---|
| 1978. | NHCH$_2$CH$_2$CH$_2$O-(1-tetrazolyl) |
| 1979. | NHCH(CH$_3$)O-(1-tetrazolyl) |
| 1980. | NHCH(CH$_3$)CH$_2$O-(1-tetrazolyl) |
| 1981. | NHCH(CH$_3$)CH$_2$CH$_2$O-(1-tetrazolyl) |
| 1982. | NHCH(CH$_2$CH$_3$)O-(1-tetrazolyl) |
| 1983. | NHCH(CH$_2$CH$_3$)CH$_2$O-(1-tetrazolyl) |
| 1984. | NHCH(CH$_2$CH$_3$)CH$_2$CH$_2$O-(1-tetrazolyl) |
| 1985. | NHCHO |
| 1986. | NHCOCH$_3$ |
| 1987. | NHCOCH$_2$CH$_3$ |
| 1988. | NHCO(CH$_2$)$_2$CH$_3$ |
| 1989. | NHCO(CH$_2$)$_3$CH$_3$ |
| 1990. | NHCOCH(CH$_3$)$_2$ |
| 1991. | NHCOCH$_2$CH(CH$_3$)$_2$ |
| 1992. | NHCOC(CH$_3$)$_3$ |
| 1993. | NHCOCF$_3$ |
| 1994. | NHCOCF$_2$CF$_3$ |
| 1995. | NHCO(CF$_2$)$_2$CF$_3$ |
| 1996. | NHCOCH(CH)CH$_3$ |
| 1997. | NHCOCH(OCH$_3$)CH$_3$ |
| 1998. | NHCOCH$_2$CH(CH)CH$_3$ |
| 1999. | NHCOCH$_2$CH(OCH$_3$)CH$_3$ |
| 2000. | NHCOCH=CH$_2$ |
| 2001. | NHCOCH=CHCH$_3$ |
| 2002. | NHCOCH$_2$CH=CH$_2$ |
| 2003. | NHCOCH(CH$_3$)CH=CH$_2$ |
| 2004. | NHCOC≡OH |
| 2005. | NHCOC≡CCH$_3$ |
| 2006. | NHCOCH$_2$C≡OH |
| 2007. | NHCOCH(CH$_3$)C≡OH |
| 2008. | NHCOC≡CCl |
| 2009. | NHCOC≡CCH$_2$OH |
| 2010. | NHCOC≡CCH$_2$OCH$_3$ |
| 2011. | N(CH$_3$)CHO |
| 2012. | N(CH$_3$)COCH$_3$ |
| 2013. | N(CH$_3$)COCH$_2$CH$_3$ |
| 2014. | N(CH$_3$)CO(CH$_2$)$_2$CH$_3$ |
| 2015. | N(CH$_3$)CO(CH$_2$)$_3$CH$_3$ |
| 2016. | N(CH$_3$)COCH(CH$_3$)$_2$ |
| 2017. | N(CH$_3$)COCH$_2$CH(CH$_3$)$_2$ |
| 2018. | N(CH$_3$)COC(CH$_3$)$_3$ |
| 2019. | N(CH$_3$)COCF$_3$ |
| 2020. | N(CH$_3$)COCF$_2$CF$_3$ |
| 2021. | N(CH$_2$CH$_3$)CHO |
| 2022. | N(CH$_2$CH$_3$)COCH$_3$ |
| 2023. | N(CH$_2$CH$_3$)COCH$_2$CH$_3$ |
| 2024. | N(CH$_2$CH$_3$)CO(CH$_2$)$_2$CH$_3$ |
| 2025. | N(CH$_2$CH$_3$)CO(CH$_2$)$_2$CH$_3$ |
| 2026. | N(CH$_2$CH$_3$)COCH(CH$_3$)$_2$ |
| 2027. | N(CH$_2$CH$_3$)COCH$_2$CH(CH$_3$)$_2$ |
| 2028. | N(CH$_2$CH$_3$)COC(CH$_3$)$_3$ |
| 2029. | N(CH$_2$CH$_3$)COCF$_3$ |
| 2030. | N(CH$_2$CH$_3$)COCF$_2$CF$_3$ |
| 2031. | N(CH(CH$_3$)$_2$)CHO |
| 2032. | N(CH(CH$_3$)$_2$)COCH$_3$ |
| 2033. | N(CH(CH$_3$)$_2$)COCH$_2$CH$_3$ |
| 2034. | N(CH(CH$_3$)$_2$)CO(CH$_2$)$_2$CH$_3$ |
| 2035. | N(CH(CH$_3$)$_2$)CO(CH$_2$)$_3$CH$_3$ |
| 2036. | N(CH(CH$_3$)$_2$)COCH(CH$_3$)$_2$ |
| 2037. | N(CH(CH$_3$)$_2$)COCH$_2$CH(CH$_3$)$_2$ |
| 2038. | N(CH(CH$_3$)$_2$)COC(CH$_3$)$_3$ |
| 2039. | N(CH(CH$_3$)$_2$)COCF$_3$ |
| 2040. | N(CH(CH$_3$)$_2$)COCF$_2$CF$_3$ |
| 2041. | N(CH(CH$_2$CH)CH$_3$)CHO |
| 2042. | N(CH(CH$_2$CH)CH$_3$)COCH$_3$ |
| 2043. | N(CH(CH$_2$CH)CH$_3$)COCH$_2$CH$_3$ |
| 2044. | N(CH(CH$_2$CH)CH$_3$)CO(CH$_2$)$_2$CH$_3$ |
| 2045. | N(CH(CH$_2$CH)CH$_3$)CO(CH$_2$)$_3$CH$_3$ |
| 2046. | N(CH(CH$_2$CH)CH$_3$)COCH(CH$_3$)$_2$ |
| 2047. | N(CH(CH$_2$CH)CH$_3$)COCH$_2$CH—(CH$_3$)$_2$ |
| 2048. | N(CH(CH$_2$CH)CH$_3$)COC(CH$_3$)$_3$ |
| 2049. | N(CH(CH$_2$CH)CH$_3$)COCF$_3$ |
| 2050. | N(CH(CH$_2$CH)CH$_3$)COCF$_2$CF$_3$ |
| 2051. | N(CH(CH$_2$OCH$_3$)CH$_3$)CHO |
| 2052. | N(CH(CH$_2$OCH$_3$)CH$_3$)COCH$_3$ |
| 2053. | N(CH(CH$_2$OCH$_3$)CH$_3$)COCH$_2$CH$_3$ |
| 2054. | N(CH(CH$_2$OCH$_3$)CH$_3$)CO—(CH$_2$)$_2$CH$_3$ |
| 2055. | N(CH(CH$_2$OCH$_3$)CH$_3$)CO—(CH$_2$)$_3$CH$_3$ |
| 2056. | N(CH(CH$_2$OCH$_3$)CH$_3$)CO—CH(CH$_3$)$_2$ |
| 2057. | N(CH(CH$_2$OCH$_3$)CH$_3$)CO—CH$_2$CH(CH$_3$)$_2$ |
| 2058. | N(CH(CH$_2$OCH$_3$)CH$_3$)COC(CH$_3$)$_3$ |
| 2059. | N(CH(CH$_2$OCH$_3$)CH$_3$)COCF$_3$ |
| 2060. | N(CH(CH$_2$OCH$_3$)CH$_3$)COCF$_2$CF$_3$ |
| 2061. | NHCOOCH$_3$ |
| 2062. | NHCOOCH$_2$CH$_3$ |
| 2063. | NHCOO(CH$_2$)$_2$CH$_3$ |
| 2064. | NHCOO(CH$_2$)$_3$CH$_3$ |
| 2065. | NHCOOCH(CH$_3$)$_2$ |
| 2066. | NHCOOCH$_2$CH(CH$_3$)$_2$ |
| 2067. | NHCOOC(CH$_3$)$_3$ |
| 2068. | NHCOOCH$_2$CF$_3$ |
| 2069. | NHCOOCH$_2$CHOCH$_3$ |
| 2070. | N(CH$_3$)COOCH$_3$ |
| 2071. | N(CH$_3$)COOCH$_2$CH$_3$ |
| 2072. | N(CH$_3$)COO(CH$_2$)$_2$CH$_3$ |
| 2073. | N(CH$_3$)COO(CH$_2$)$_3$CH$_3$ |
| 2074. | N(CH$_3$)COOCH(CH$_3$)$_2$ |
| 2075. | N(CH$_3$)COOCH$_2$CH(CH$_3$)$_2$ |
| 2076. | N(CH$_3$)COOC(CH$_3$)$_3$ |
| 2077. | N(CH$_3$)COOCH$_2$CF$_3$ |
| 2078. | N(CH$_3$)COOCH$_2$CHOCH$_3$ |
| 2079. | N(CH$_2$CH$_3$)COOCH$_3$ |
| 2080. | N(CH$_2$CH$_3$)COOCH$_2$CH$_3$ |
| 2081. | N(CH$_2$CH$_3$)COO(CH$_2$)$_2$CH$_3$ |
| 2082. | N(CH$_2$CH$_3$)COO(CH$_2$)$_3$CH$_3$ |
| 2083. | N(CH$_2$CH$_3$)COOCH(CH$_3$)$_2$ |
| 2084. | N(CH$_2$CH$_3$)COOCH$_2$CH(CH$_3$)$_2$ |
| 2085. | N(CH$_2$CH$_3$)COOC(CH$_3$)$_3$ |
| 2086. | N(CH$_2$CH$_3$)COOCH$_2$CF$_3$ |
| 2087. | N(CH$_2$CH$_3$)COOCH$_2$CHOCH$_3$ |
| 2088. | N(CH(CH$_3$)$_2$)COOCH$_3$ |
| 2089. | N(CH(CH$_3$)$_2$)COOCH$_2$CH$_3$ |
| 2090. | N(CH(CH$_3$)$_2$)COO(CH$_2$)$_2$CH$_3$ |
| 2091. | N(CH(CH$_3$)$_2$)COO(CH$_2$)$_3$CH$_3$ |
| 2092. | N(CH(CH$_3$)$_2$)COOCH(CH$_3$)$_2$ |
| 2093. | N(CH(CH$_3$)$_2$)COOCH$_2$CH(CH$_3$)$_2$ |
| 2094. | N(CH(CH$_3$)$_2$)COOC(CH$_3$)$_3$ |
| 2095. | N(CH(CH$_3$)$_2$)COOCH$_2$CF$_3$ |
| 2096. | N(CH(CH$_3$)$_2$)COOCH$_2$CHOCH$_3$ |
| 2097. | N(CH(CH$_2$CH)CH$_3$)COOCH$_3$ |
| 2098. | N(CH(CH$_2$CH)CH$_3$)COOCH$_2$CH$_3$ |
| 2099. | N(CH(CH$_2$CH)CH$_3$)COO—(CH$_2$)$_2$CH$_3$ |
| 2100. | N(CH(CH$_2$CH)CH$_3$)COO—(CH$_2$)$_3$CH$_3$ |
| 2101. | N(CH(CH$_2$CH)CH$_3$)COOCH(CH$_3$)$_2$ |
| 2102. | N(CH(CH$_2$CH)CH$_3$)COO—CH$_2$CH(CH$_3$)$_2$ |
| 2103. | N(CH(CH$_2$CH)CH$_3$)COOC(CH$_3$)$_3$ |
| 2104. | N(CH(CH$_2$CH)CH$_3$)COOCH$_2$CF$_3$ |
| 2105. | N(CH(CH$_2$CH)CH$_3$)COO—CH$_2$CHOCH$_3$ |
| 2106. | N(CH(CH$_2$OCH$_3$)CH$_3$)COOCH$_3$ |
| 2107. | N(CH(CH$_2$OCH$_3$)CH$_3$)COO—CH$_2$CH$_3$ |
| 2108. | N(CH(CH$_2$OCH$_3$)CH$_3$)COO—(CH$_2$)$_2$CH$_3$ |
| 2109. | N(CH(CH$_2$OCH$_3$)CH$_3$)COO—(CH$_2$)$_3$CH$_3$ |
| 2110. | N(CH(CH$_2$OCH$_3$)CH$_3$)COO—CH(CH$_3$)$_2$ |
| 2111. | N(CH(CH$_2$OCH$_3$)CH$_3$)COO—CH$_2$CH(CH$_3$)$_2$ |
| 2112. | N(CH(CH$_2$OCH$_3$)CH$_3$)COO—C(CH$_3$)$_3$ |
| 2113. | N(CH(CH$_2$OCH$_3$)CH$_3$)COO—CH$_2$CF$_3$ |
| 2114. | N(CH(CH$_2$OCH$_3$)CH$_3$)COO—CH$_2$CHOCH$_3$ |
| 2115. | NHCONHCH$_3$ |
| 2116. | NHCONHCH$_2$CH$_3$ |
| 2117. | NHCONH(CH$_2$)$_2$CH$_3$ |
| 2118. | NHCONH(CH$_2$)$_3$CH$_3$ |
| 2119. | NHCONHCH(CH$_3$)$_2$ |
| 2120. | NHCONHCH$_2$CH(CH$_3$)$_2$ |

TABLE A-continued

| No. | R6 |
|---|---|
| 2121. | NHCONHC(CH₃)₃ |
| 2122. | NHCONHCH₂CF₃ |
| 2123. | NHCONHCH₂CHOCH₃ |
| 2124. | N(CH₃)CONHCH₃ |
| 2125. | N(CH₃)CONHCH₂CH₃ |
| 2126. | N(CH₂CH₃)CONHCH₃ |
| 2127. | N(CH₂CH₃)CONHCH₂CH₃ |
| 2128. | N(CH(CH₃)₂)CONHCH₃ |
| 2129. | N(CH(CH₃)₂)CONHCH₂CH₃ |
| 2130. | N(CH(CH₂CH)CH₃)CONHCH₃ |
| 2131. | N(CH(CH₂CH)CH₃)CONHCH₂CH₃ |
| 2132. | N(CH(CH₂OCH₃)CH₃)CONHCH₃ |
| 2133. | N(CH(CH₂OCH₃)CH₃)CONH—CH₂CH₃ |
| 2134. | NHCON(CH₃)₂ |
| 2135. | NHCON(CH₂CH₃)₂ |
| 2136. | NHCON(CH₃)(CH₂)₂CH₃ |
| 2137. | NHCON(CH₃)(CH₂)₃CH₃ |
| 2138. | NHCON(CH₃)CH(CH₃)₂ |
| 2139. | NHCON(CH₃)CH₂CH(CH₃)₂ |
| 2140. | NHCON(CH₃)C(CH₃)₃ |
| 2141. | NHCON(CH₂CF₃)₂ |
| 2142. | NHCON(CH₂CHOCH₃)₂ |
| 2143. | NHSONHCH₃ |
| 2144. | NHSONHCH₂CH₃ |
| 2145. | NHSONH(CH₂)₂CH₃ |
| 2146. | NHSONH(CH₂)₃CH₃ |
| 2147. | NHSONHCH(CH₃)₂ |
| 2148. | NHSONHCH₂CH(CH₃)₂ |
| 2149. | NHSONHC(CH₃)₃ |
| 2150. | NHSONHCH₂CF₃ |
| 2151. | NHSONHCH₂CHOCH₃ |
| 2152. | NHSON(CH₃)₂ |
| 2153. | NHSON(CH₂CH₃)₂ |
| 2154. | NHSON(CH₃)(CH₂)₂CH₃ |
| 2155. | NHSON(CH₃)(CH₂)₃CH₃ |
| 2156. | NHSON(CH₃)CH(CH₃)₂ |
| 2157. | NHSON(CH₃)CH₂CH(CH₃)₂ |
| 2158. | NHSON(CH₃)C(CH₃)₃ |
| 2159. | NHSON(CH₂CF₃)₂ |
| 2160. | NHSON(CH₂CHOCH₃)₂ |
| 2161. | NHS(O)₂NHCH₃ |
| 2162. | NHS(O)₂NHCH₂CH₃ |
| 2163. | NHS(O)₂NH(CH₂)₂CH₃ |
| 2164. | NHS(O)₂NH(CH₂)₃CH₃ |
| 2165. | NHS(O)₂NHCH(CH₃)₂ |
| 2166. | NHS(O)₂NHCH₂CH(CH₃)₂ |
| 2167. | NHS(O)₂NHC(CH₃)₃ |
| 2168. | NHS(O)₂NHCH₂CF₃ |
| 2169. | NHS(O)₂NHCH₂CHOCH₃ |
| 2170. | NHS(O)₂N(CH₃)₂ |
| 2171. | NHS(O)₂N(CH₂CH₃)₂ |
| 2172. | NHS(O)₂N(CH₃)(CH₂)₂CH₃ |
| 2173. | NHS(O)₂N(CH₃)(CH₂)₃CH₃ |
| 2174. | NHS(O)₂N(CH₃)CH(CH₃)₂ |
| 2175. | NHS(O)₂N(CH₃)CH₂CH(CH₃)₂ |
| 2176. | NHS(O)₂N(CH₃)C(CH₃)₃ |
| 2177. | NHS(O)₂N(CH₂CF₃)₂ |
| 2178. | NHS(O)₂N(CH₂CHOCH₃)₂ |
| 2179. | (4-methyltetrahydropyran-3-yl)amino |
| 2180. | (1-methylpyrrolidin-3-yl)amino |
| 2181. | (3-methyltetrahydrofuran-3-yl)amino |
| 2182. | (2-methyltetrahydrofuran-2-yl)amino |
| 2183. | N=CHNH₂ |
| 2184. | N=CHNH(CH₃) |
| 2185. | N=CHN(CH₃)₂ |
| 2186. | N=CHNH(CH₂CH₃) |
| 2187. | N=CHN(CH₂CH₃)₂ |
| 2188. | N=CHNCH₃(CH₂CH₃) |
| 2189. | N=C(CH₃)NH₂ |
| 2190. | N=C(CH₃)NH(CH₃) |
| 2191. | N=C(CH₃)N(CH₃)₂ |
| 2192. | N=C(CH₃)NH(CH₂CH₃) |
| 2193. | N=C(CH₃)N(CH₂CH₃)₂ |
| 2194. | N=C(CH₃)NCH₃(CH₂CH₃) |
| 2195. | N=C(CH₂CH₃)NH₂ |
| 2196. | N=C(CH₂CH₃)NH(CH₃) |
| 2197. | N=C(CH₂CH₃)N(CH₃)₂ |
| 2198. | N=C(CH₂CH₃)NH(CH₂CH₃) |
| 2199. | N=C(CH₂CH₃)N(CH₂CH₃)₂ |
| 2200. | N=C(CH₂CH₃)NCH₃(CH₂CH₃) |
| 2201. | N=C(NH₂)NH₂ |
| 2202. | N=C(NH₂)NH(CH₃) |
| 2203. | N=C(NH₂)N(CH₃)₂ |
| 2204. | N=C(NH₂)NH(CH₂CH₃) |
| 2205. | N=C(NH₂)N(CH₂CH₃)₂ |
| 2206. | N=C(NH₂)NCH₃(CH₂CH₃) |
| 2207. | N=C(NH(CH₃))NH(CH₃) |
| 2208. | N[]C(NH(CH₃))N(CH₃)₂ |
| 2209. | N=C(NH(CH₃))NH(CH₂CH₃) |
| 2210. | N[]C(NH(CH₃))N(CH₂CH₃)₂ |
| 2211. | N=C(NH(CH₃))NCH₃(CH₂CH₃) |
| 2212. | N=C(NH(CH₂CH₃))NH(CH₃) |
| 2213. | N=C(NH(CH₂CH₃))N(CH₃)₂ |
| 2214. | N=C(NH(CH₂CH₃))NH(CH₂CH₃) |
| 2215. | N=C(NH(CH₂CH₃))N(CH₂CH₃)₂ |
| 2216. | N=C(NH(CH₂CH₃))NCH₃(CH₂CH₃) |
| 2217. | (imidazolidin-2-ylidene)amino |
| 2218. | (1-methylimidazolidin-2-ylidene)amino |
| 2219. | (1-ethylimidazolidin-2-ylidene)amino |
| 2220. | (1-isopropylimidazolidin-2-ylidene)amino |

TABLE A-continued

| No. | R6 |
|---|---|
| 2221. | 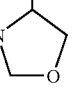 |
| 2222. | |
| 2223. | |
| 2224. | |
| 2225. | |
| 2226. | |
| 2227. | |
| 2228. | |
| 2229. | |
| 2230. | |
| 2231. | 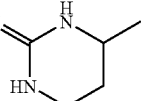 |
| 2232. | |
| 2233. | |
| 2234. | |
| 2235. | |
| 2236. | |
| 2237. | |

The invention especially relates to a the use of at least one compound of the formula I or a salt thereof for protecting a plant against attack or infestation by a phytopathogenic organism, especially a microorganism, especially a fungal organism (preferably selected from the group consisting of Ascomycetes, Basidiomycetes, Oomycetes and *Fungi imperfecti*), a bacterium, a virus or a nematode; said compound or salt being selected from the compounds given in Table A or especially in table 59, comprising administering said compound and/or salt to one or more selected from the group consisting of a plant, a part of a plant, seeds and the site of a plant.

Preferred are compounds of formula I, wherein n=0, $R_1$=halogen or haloalkoxy, each of $R_2$ to $R_5$ is hydrogen and $R_6$ is lower alkylamino wherein the lower alkyl moiety is substituted by one or more (preferably 1 to 3, especially 1 or 2) substituents independently selected from the group consisting of unsubstituted amino, N-mono- or N,N-di-(lower alkyl)-amino, (lower alkoxy)-lower alkoxy, lower alkoxy-carbonylamino, hydroxy-lower alkoxycarbonylamino, lower alkoxy-lower alkoxycarbonylamino, morpholinyl, hydroxy-lower alkylamino, hydroximino, alkoximino, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, hydroxy, lower alkoxy, lower alkenyloxy, lower alkinyloxy, lower haloalkoxy, piperazinyl, lower alkanoyl-piperazinyl (including formylpiperazinyl) and optionally substituted heteroaryloxy, or a salt thereof.

More preferred is a compound of formula I, wherein n=0, $R_1$=chlorine or haloalkoxy, each of $R_2$ to $R_5$ is hydrogen and $R_6$ is alkoxyalkylamino, or a salt thereof.

Especially preferred are compounds 4, 5, 12, 13, 14, 15, 32 and 40 of table 59.

The present invention also relates to the novel compounds of formula I mentioned hereinbefore and hereinafter, or salts thereof;

Especially preferred are the compounds with n=1 (N-oxides) of formula I, or the salts thereof.

Especially preferred is also a compound of formula I selected from the group of compounds provided in tables 1 to 58, or a salt thereof, or that total group of compounds, with the exception of N-(3-trifluoromethyl-phenyl)-4-[2-(3-hydroxy-propyl-amino)-4-pyridyl]-2-pyrimidine-amine,
N-(3-chloro-phenyl)-4-[2-(3-hydroxy-propyl-amino)-4-pyridyl]-2-pyrimidine-amine,
N-(3-chloro-phenyl)-4-[2-(2-hydroxy-propyl-amino)-4-pyridyl]-2-pyrimidine-amine,
N-(3-chloro-phenyl)-4-[2-(2-carboxy-ethyl-amino)-4-pyridyl]-2-pyrimidine-amine,
N-(3-chloro-phenyl)-4-[2-(2-carbamoyl-ethyl-amino)-4-pyridyl]-2-pyrimidine-amine,
N-(3-chloro-phenyl)-4-[2-(2-ethoxycarbonyl-ethyl-amino)-4-pyridyl]-2-pyrimidine-amine,
N-(3-trifluoromethyl-phenyl)-4-[2-(2-hydroxy-propyl-amino)-4-pyridyl]-2-pyrimidine-amine,
N-(3-trifluoromethyl-phenyl)-4-[2-(2-carboxy-ethyl-amino)-4-pyridyl]-2-pyrimidine-amine,
N-(3-trifluoromethyl-phenyl)-4-[2-(2-carbamoyl-ethyl-amino)-4-pyridyl]-2-pyrimidine-amine,
N-(3-trifluoromethyl-phenyl)-4-[2-(2-ethoxycarbonyl-ethyl-amino)-4-pyridyl]-2-pyrimidine-amine,
N-(3-chloro-phenyl)-4-[2-(2-imidazol-1-yl-ethyl-amino)-4-pyridyl]-2-pyrimidine-amine,
N-(3-chloro-phenyl)-4-[2-(2-acetamido-ethyl-amino)-4-pyridyl]-2-pyrimidine-amine,
N-(3-chloro-phenyl)-4-(2-hydrazino-4-pyridyl)-2-pyrimidine-amine,
N-(3-chloro-phenyl)-4-[2-(2-guanidyl-ethyl-amino)-4-pyridyl]-2-pyrimidine-amine,
N-(3-chloro-phenyl)-4-[2-{2-(methylamino-carbonylamino)-ethyl-amino}-4-pyridyl]-2-pyrimidine-amine,
N-(3-chloro-phenyl)-4-[2-(2-amidino-ethyl-amino)-4-pyridyl]-2-pyrimidine-amine,
N-(3-chloro-phenyl)-4-[2-{2-(N-hydroxy-carbamoyl)-ethyl-amino}-4-pyridyl]-2-pyrimidine-amine,
N-(3-trifluormethyl-phenyl)-4-[2-{2-(N-hydroxy-carbamoyl)-ethyl-amino}-4-pyridyl]-2-pyrimidine-amine,
N-(3-chloro-phenyl)-4-[2-(2-amino-ethyl-amino)-4-pyridyl]-2-pyrimidine-amine,
N-(3-trifluoromethyl-phenyl)-4-[2-(2-amino-ethyl-amino)-4-pyridyl]-2-pyrimidine-amine,
N-(3-chloro-phenyl)-4-[2-(2-hydroxy-ethyl-amino)-4-pyridyl]-2-pyrimidine-amine,
N-(3-chloro-phenyl)-4-[2-(1-piperazinyl)-4-pyridyl]-2-pyrimidine-amine,
N-(3-chloro-phenyl)-4-[2-{2-(4-morpholinyl)-ethyl-amino}-4-pyridyl]-2-pyrimidine-amine,
N-(3-chloro-phenyl)-4-[2-(4-morpholinyl)-4-pyridyl]-2-pyrimidine-amine,
N-(3-chloro-phenyl)-4-[2-(2-n-propylamino-4-pyridyl)-2-pyrimidine-amine,
N-(3-chloro-phenyl)-4-[2-(n-1-butylamino)-4-pyridyl]-2-pyrimidine-amine,
N-(3-chloro-phenyl)-4-[2-(2-amino-4-pyridyl)-2-pyrimidine-amine, and
N-(3-chloro-phenyl)-4-(2-dimethylamino-4-pyridyl)-2-pyrimidine-amine, or a salt thereof.

Preferred is also a compound of the formula I selected from the compounds mentioned in tables 2, 4, 5, 8, 31, 33, 34 and 37, or a salt thereof, or the whole group of compounds mentioned in said table.

Especially preferred is a compound of the formula I selected from the compounds of formula I mentioned in table 59, or a salt thereof, or the whole group of compounds in that table, or a salt of any thereof, with the exception of N-(3-chloro-phenyl)-4-[2-(3-hydroxy-propyl-amino)-4-pyridyl]-2-pyrimidine-amine,
N-(3-chloro-phenyl)-4-[2-(2-hydroxy-propyl-amino)-4-pyridyl]-2-pyrimidine-amine,
N-(3-chloro-phenyl)-4-[2-(2-imidazol-1-yl-ethyl-amino)-4-pyridyl]-2-pyrimidine-amine,
N-(3-chloro-phenyl)-4-(2-hydrazino-4-pyridyl)-2-pyrimidine-amine,
N-(3-chloro-phenyl)-4-[2-(2-amino-ethyl-amino)-4-pyridyl]-2-pyrimidine-amine,
N-(3-chloro-phenyl)-4-[2-(2-hydroxy-ethyl-amino)-4-pyridyl]-2-pyrimidine-amine,
N-(3-chloro-phenyl)-4-[2-(1-piperazinyl)-4-pyridyl]-2-pyrimidine-amine,
N-(3-chloro-phenyl)-4-[2-{2-(4-morpholinyl)-ethyl-amino}-4-pyridyl]-2-pyrimidine-amine,
N-(3-chloro-phenyl)-4-[2-(4-morpholinyl)-4-pyridyl]-2-pyrimidine-amine,
N-(3-chloro-phenyl)-4-(2-n-propylamino-4-pyridyl)-2-pyrimidine-amine,
N-(3-chloro-phenyl)-4-(2-amino-4-pyridyl)-2-pyrimidine-amine, and
N-(3-chloro-phenyl)-4-(2-dimethylamino-4-pyridyl)-2-pyrimidine-amine, or a salt thereof.

The compounds useful according to the invention are prepared according to methods that are, per se, known in the art (this does mean, however, that, where novel compounds are produced, the respective process of manufacture is also novel) especially by reacting a compound of the formula (II),

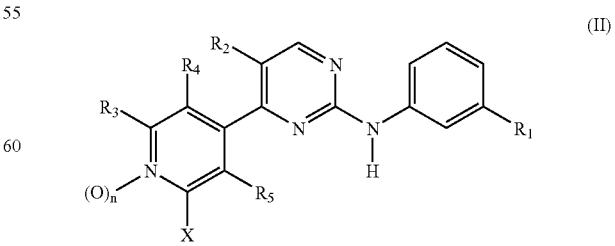

(or a salt thereof) wherein X is a leaving group, especially halo, for example fluoro, chloro, bromo or iodo, and the other moieties have the meanings given for a compound of the formula I1, with a hydrazino, amino or imino compound of the formula (III)

(or a salt thereof) wherein $R_6$ has the meanings given for a compound of the formula I under a) where hydrazino is unsubstituted or mono to threefold substituted by optionally substituted alkyl, b), c) where piperazinyl is bound via a nitrogen atom, d) where morpholinyl is morpholino, or especially e), or by reacting a compound of the formula (IV)

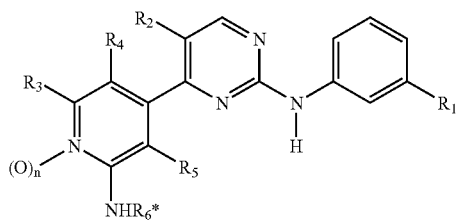

wherein n and $R_1$ to $R_5$ have the meanings given for a compound of the formula I and wherein $R_6^*$ is hydrogen or optionally substituted alkyl as defined above, with a halogenide (Va) or an anhydride (Vb)

wherein Hal is chloro, bromo or iodo, especially chloro or bromo and $R_9$ has the meanings of the carboxyl, sulfoxyl and sulfonyl moieties for a compound of the formula I under $R_6$=f), g), h) or i);

or by reacting a compound of the formula IV with an acetal of an amide (Vc), or any other form of an activated amide

wherein the term $(R_{10})_2N$ is $R_8$ as defined under formula I and $R_{11}$ is alkyl or $C(OR_{11})_2$ has the meaning of a cyclic acetal, such as dioxolanyl or dioxanyl for a compound of the formula I under $R_6$=g), wherein $R_7$ is hydrogen or alkyl, or by reacting a compound of the formula IV with a S-alkyl thiourea derivative (Vd), or any other form of an activated urea

wherein the term $R_{10}N$ is $R_8$ and $R_{11}$ is alkyl for a compound of the formula I under $R_6$=g), wherein $R_7$ is amino, mono- or dialkylamino, or by reacting a compound of the formula IV with an aldehyde analogue of an unsubstituted or substituted lower alkyl compound that carries an aldehyde (—CHO) instead of the binding methylene group (—CH$_2$—) of the corresponding unsubstituted or substituted lower alkyl as described above as substituent $R_6$ "unsubstituted or substituted mono- or di-(lower alkyl)amino" wherein the substituents are as defined above in a final product of formula I in the presence of a reducing agent, preferably sodium cyanoborohydride for a compound of the formula I, wherein $R_6$ is mono- or di-(lower alkyl)amino wherein the lower alkyl moieties are unsubstituted or substituted by one or more substituents independently selected from the group consisting of amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo bound to a carbon that is not directly bound to a heteroatom, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkylcarbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfinyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl (including formylpiperazinyl), optionally substituted heteroaryl and optionally substituted heteroaryloxy;

or (to obtain substituted hydrazino $R_6$ in accordance with the definition under a) for a compound of formula I) by reacting a compound of the formula (VI)

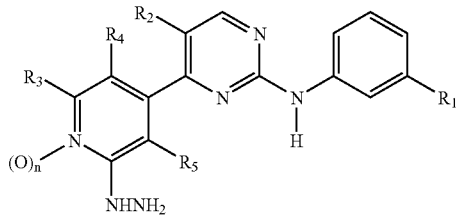

wherein n and $R_1$ to $R_5$ have the meanings given for a compound of the formula I, with a halogenide (Va) or an anhydride (Vb)

wherein Hal is chloro, bromo or iodo, especially chloro or bromo and $R_9$ has the meanings of the acyl moiety for a compound of the formula I under $R_6$=a), or (to obtain substituted hydrazino $R_6$ in accordance with the definition under a) for a compound of formula I) by reacting a comound of the formula (VII a–d)

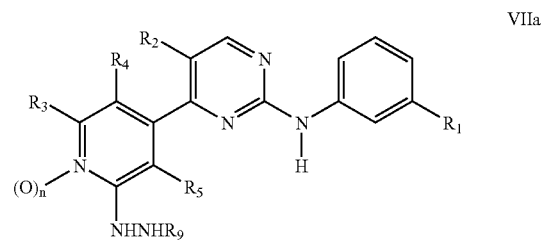

-continued

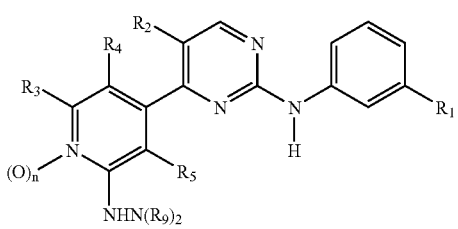

VIIb

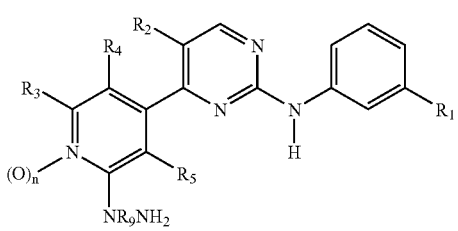

VIIc

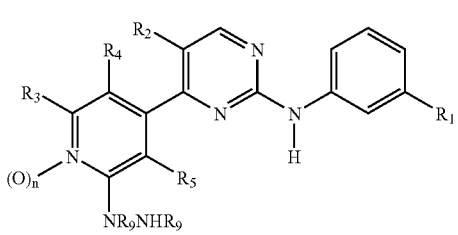

VIId wherein n and $R_1$ to $R_5$ have the meanings given for a compound of the formula I and $R_9$ has the meanings of the acyl moiety for a compound of the formula I under $R_6$=a), with a halogenide of the formula (VIII)

Hal-$R_{12}$      VIII wherein Hal is chloro, bromo or iodo, especially chloro or bromo and $R_{12}$ has the meanings of the alkyl moiety for a compound of the formula I under $R_6$=a), and, if desired, a compound of the formula I thus obtained is converted into a salt thereof, or an obtained salt is converted into a free compound and/or into a different salt, or a compound of formula I is converted into a different compound of formula I, where functional groups in a starting material of the formula II and/or III, where necessary, are present in protected form, and any protecting groups present are removed in order to obtain the final product.

The compounds of the formula I thus obtainable and the remaining compounds of the formula I can, mutatis mutandis, also be prepared in accordance with manufacturing processes described in WO 95/09853, or in analogy to the methods described therein—therefor WO 95/09853 is herewith incorporated by reference. Also appropriate protecting groups, their introduction and removal are described in WO 95/09853. The characteristic of protecting groups in the strict sense is that they are not present in the final compounds of formula I.

A compound of the formula II can be obtained preferably by reacting a compound of the formula (IX)

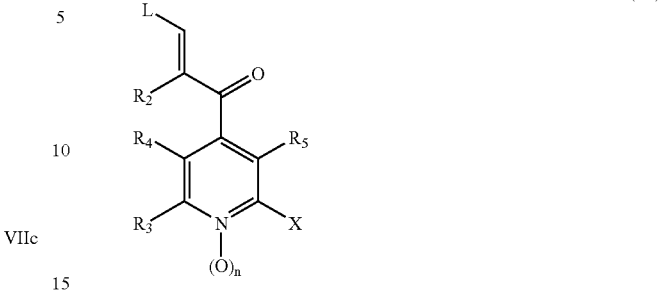

(or—if n is 0—a salt thereof) wherein L is a leaving group, especially alkoxy, such as lower alkoxy, esterified OH (especially tosyloxy), or di-(lower alkylamino), X is a leaving group (preferably halo, such as chloro, bromo or iodo) and the other moieties are defined as for a compound of the formula I, with a guanidino compound of the formula (XI),

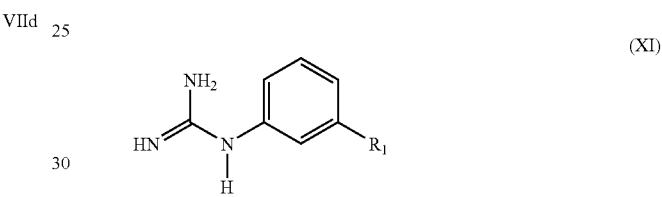

(or a salt thereof) wherein $R_1$ is as defined for a compound of the formula I.

The reaction preferably takes place under conditions analogous to those mentioned in PCT application WO 95/09583, that is, in a suitable solvent or dispersing agent, for example a suitable alcohol, such as isopropanpol, or 2-butanol, at a temperature from room temperature (approximately 20° C.) to 150° C., e.g. under reflux.

The compound of the formula (IX) are known or can be obtained in accordance with methods that are known in the art, e.g. by reacting a compound of the formula (XII),

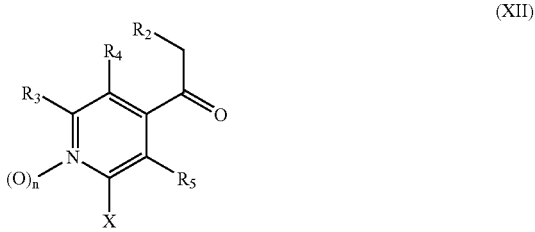

wherein the moieties $R_2$, $R_3$, $R_3$ and $R_5$ have the meanings given for a compound of the formula I and wherein X is a leaving group, preferably as defined for a compound of the formula (IX), either (i) under Claisen or analogue condensation reaction conditions (leading to a free hydroxy instead of the leaving group L in a compound of the formula IV; this free hydroxy group can then be converted into a leaving group, for example by ether formation with an alkylalkohol ("Alkoxy-H";), yielding alkoxy as L, such as lower alkoxy, or by reaction with an acid or an active ester derivative, e.g.

an acid chloride, yielding esterified OH (especially tosyloxy); or to alkoxy L, depending on the reaction conditions), or (ii) preferably by reaction with an N,N-di-(lower alkyl)-formamide di-lower alkylacetal, especially N,N-di-(methyl) formamide di-methylacetal, analogous to the procedure described in European Patent Application EP 0 233 461, which is incorporated by reference, e.g. by reaction in the respective N,N-di-(lower alkyl)-formamide di-lower alkylacetal at a temperature between room temperature and the boiling point of the reaction mixture, especially under reflux conditions.

An intermediate of the formula (XII) can, for example, be obtained by reaction of a metallated alkyl derivative of the formula (XIII),

wherein $R_2$ is as defined for a compound of the formula I (preferably it is hydrogen or alkyl) and Metal stands preferably for Mg—Hal (Hal=halogen) or Li, with a pyridine acid derivative of the formula (XIV),

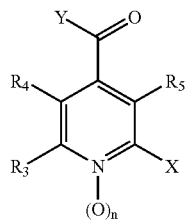

wherein $R_3$ to $R_5$ have the meanings given for a compound of the formula I, X is a leaving group, preferably as defined for a compound of the formula (II), and Y is a leaving group, preferably N-lower alkyl-N-lower alkoxy-amino or halogen, under standard conditions for alkylation reactions.

Alternatively, an intermediate of the formula (XII), wherein n is 0, can be obtained by reaction of a metallated pyridine derivative of the formula (XV),

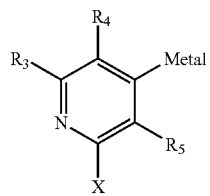

wherein $R_3$ to $R_5$ have the meanings given for a compound of the formula I, X is a leaving group, preferably as defined for a compound of the formula (IX), and Metal stands for Mg—Hal (Hal=halogen) or Li, under standard conditions for alkylation reactions with an acyl equivalent of the formula (XVI),

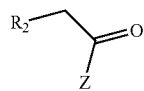

wherein $R_2$ is as defined for a compound of formula I and Z is halo, or forms with the rest of the molecule an amide, an alkoxyamide, an anhydride or the like; or Z is hydrogen (meaning that the compound (XVI) is an aldehyde), resulting after the reaction in an alcohol that is then oxidised with a selective oxidant, for example in the presence of oxalylchloride and dimethyl sulfoxide, to the ketone intermediate of the formula (XII).

A starting material of the formula III is known, can be prepared by methods known in the art or is commercially available.

A starting material of the formula (XI) can be prepared (preferably obtaining an acid addition salt) by reaction of an aniline derivative of the formula (XVII),

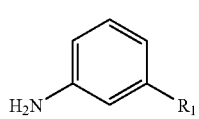

wherein $R_1$ is as defined for a compound of formula I, with cyanamide (NC—$NH_2$) in a suitable solvent, e.g. an alcohol, such as a lower alkanol, for example (i) in the presence of equimolar amounts of the salt-forming acid, for example nitric acid, or (ii) in the presence of a clear, for example 60%, excess of a mineral acid, such as hydrochloric acid, where an ammonium salt of the desired salt-forming acid is added when the reaction is complete; at a temperature between room temperature and 150° C., e.g. under reflux.

Compounds of the formulae XIII, XIV, XV and XVI can be prepared according to methods that are known in the art.

The synthesis of many of the starting materials and intermediates can also be done as described in or in analogy to the processes described in WO 95/09853.

In all intermediates, functional groups that shall not participate in the reaction can be protected and deprotected at appropriate stages in order to avoid side reactions—appropriate protecting groups, their introduction and removal can be found e.g. in WO 95/09853.

The present invention also relates to novel starting materials and/or intermediates and to processes for the preparation thereof. The starting materials used and the reaction conditions chosen are preferably such that the compounds shown in this disclosure as being especially preferred or to be used preferably are obtained. Especially preferred among the process conditions are those described in the examples below, or analogous procedures.

The invention also relates to compositions which comprise the compounds of the formula I, or a salt thereof, as an active component, in particular plant-protecting compositions, and also to their use in the agricultural sector or related areas.

Active compounds of the formula I are customarily used in the form of compositions and may be added, simultaneously or successively, to the surface or plant to be treated together with additional active compounds. These additional active compounds may be either fertilizers, trace element-supplying agents or other preparations which influence plant growth. It is also possible, in this context, to use selective herbicides, such as insecticides, fungicides, bactericides, nematicides or molluscicides, or mixtures of several of these preparations, additionally, where appropriate, together with excipients, surfactants or other administration-promoting additives which are customary in formulation technology (designated collectively as carrier materials herein).

Suitable excipients and additives may be solid or liquid and are those substances which are appropriate in formulation technology, for example natural or regenerated minerals, solvents, dispersants, wetting agents, adhesives, thickening agents, binding agents or fertilizers.

A preferred method for applying a compound of formula I, or an agrochemical composition which comprises at least one of these compounds, is administration to the leaves (foliar application). The frequency and rate of aministration depend upon the risk of infestation by the corresponding pathogen. The compounds of formula II can, however, also penetrate the plant through the roots via the soil (systemic action). If the locus of the plant is impregnated with a liquid formulation or if the substances are introduced in solid form into the soil, e.g. in the form of granules (soil application). In paddy rice crops, such granules can be applied in metered amounts to the flooded rice fields. In order to treat seeds, the compounds of formula I can, however, also be applied to the seeds (coating), either by impregnating the grains or tubers with a liquid formulation of the active ingredient, or by coating them with a solid formulation.

Advantageous rates of application are in normally from 5 g to 2 kg of active ingredient (a.i.) per hectare (ha), preferably from 10 g to 1 kg of a.i./ha, especially from 20 g to 600 g a.i./ha. When the compound are used as seed dressings, dosages of from 10 mg to 1 g of active ingredient per kg seed are advantageous employed. The agrochemical compositions generally comprise 0.1 to 99% by weight, preferably 0.1 to 95% by weight, of a compound of formula I, 99.9 to 1% by weight, preferably 99.8 to 5% by weight, of a solid or liquid adjuvant and 0 to 25% by weight, preferably 0.1 to 25% by weight, of a surfactant. Whereas commercial products will preferably be formulated as concentrates, the end user will normally employ dilute formulations.

The compositions may also comprise further auxiliaries, such as stabilizers, antifoams, viscosity regulators, binders or tackifiers, as well as fertilizers or other active ingredients for obtaining special effects.

EXAMPLES

The subsequent examples are intended to illustrate the invention, without affecting the scope thereof.

Preparative Examples

Synthesis Example 1

(3-Chloro-phenyl)-{4-[2-(2-methoxy-1-methyl-ethylamino)-pyridin-4-yl]-pyrimidin-2-yl}-amine A mixture of (3-chloro-phenyl)-[4-(2-chloro-pyridin-4-yl)-pyrimidin-2-yl]-amine (10.0 g, 0.03 mol) and 2-amino-1-methoxypropane (14.0 g, 0.16 mol) in dioxane (75 ml) is heated in an autoclave at 195° C. for 12 hours. The reaction mixture is partitioned between ethyl acetate and water. The organic phase is separated, dried over magnesium sulfate, filtered and evaporated under reduced presssure. The residue is purified by silicagel chromatography to give the title compound, m.p. 143–144° C.

Synthesis Example 2

(3-Chloro-phenyl)-[4-(2-hydrazino-pyridin-4-yl)-pyrimidin-2-yl]-amine

A mixture of (3-chloro-phenyl)-[4-(2-chloro-pyridin-4-yl)-pyrimidin-2-yl]-amine (4.8 g, 0.015 mol) in hydrazine (20 ml, 0.41 mol) is refluxed for 90 minutes. The reaction is poured into ethanol (300 ml) with efficient stirring. The resulting precipitate is filtered with suction to yield the title compound, m.p. 201–203° C.

Synthesis Example 3

{4-[2-(1-Acetoxybutyl-2-amino)-pyridin-4-yl]-pyrimidin-2-yl}-(3-chloro-phenyl)-amine Step 1:
A mixture of (3-chloro-phenyl)-[4-(2-chloro-pyridin-4-yl)-pyrimidin-2-yl]-amine (10.0 g, 0.03 mol) and 2-amino-1-hydroxybutane (30.0 g, 0.3 mol) is heated at 180° C. for 18 hours. The reaction mixture is partitioned between ethyl acetate and water. The organic phase is separated, dried over magnesium sulfate, filtered and evaporated under reduced presssure. The residue is purified by silicagel chromatography to give the title compound, m.p. 99–101° C.

Step 2:
{4-[2-(1-Hydroxybutyl-2-amino)-pyridin-4-yl]-pyrimidin-2-yl}-(3-chloro-phenyl)-amine (1.24 g, 3.3 mmol) and acetic anhydride (0.41 g, 4.0 mmol) are refluxed in dimethoxyethane (20 ml) in the presence of a catalytic amount of DMAP for 30 minutes. The reaction mixture is evaporated under reduced pressure. The residue is crystalized by adding crushed ice. The solid is filtered and dried to give the title compound, m.p. 125–126° C.

Synthesis Example 4

{4-[3-Chloro-2-(2-methoxy-ethylamino)-pyridin-4-yl]-pyrimidin-2-yl}-(3-chloro-phenyl)-amine Step 1:
A solution of 2,3-dichloropyridine (7.4 g, 0.05 mol) in THF (15 ml) is added at −60° C. to a solution of lithium diisopropylamine (0.07 mmol) in THF/hexane (1:1, 100 ml). After stirring for one hour at the same temperature a cooled solution of acetaldehyde in THF (8 ml) is added dropwise. The reaction mixture is allowed to warm to −20° C. and is then quenched with an aqueous saturated solution of ammonium chloride. The organic phase is separated, dried over magnesium sulfate, filtered and evaporated under reduced pressure to give a clear oil, that is used in the next step without further purification.

Step 2 (Swern Oxidation):
The product described under step 1 is added carefully at −60° C. to a solution prepared from oxalyl chloride (6.0 ml, 0.07 mol) and dimethylsulfoxide (8.5 ml, 0.12 mol) in methylene chloride (150 ml) at the same temperature. After stirring the reaction mixture for 30 minutes at −60° C. triethylamine (49 ml, 0.35 mol) is added and then allowed to reach room temperature. Brine is added and the methylene chloride is evaporated under reduced pressure. The product is extracted with ether, dried over magnesium sulfate, filtered and distilled under reduced pressure to give the product as a colorless oil, b.p. 90–93/2 mm.

Step 3:

The product described under step 2 is refluxed in dimethylformamide diethylacetal (15 ml) for 15 minutes. The still hot reaction mixture is diluted with hexane and the resulting crystalline product filtered. This intermediate is refluxed with 3-chlorophenylguanidine hydrogencarbonate (11.5 g, 0.05 mol) in 2-butanol (200 ml) for 14 hours. Diluting the reaction mixture with hexane and filtering gives the intermediate in form of yellow crystals.

Step 4:

The product prepared in step 3 (1.0 g, 2.8 mmol) is refluxed in 2-methoxyethylamine (5 ml) for 8 hours. The reaction mixture is partitioned between ethyl acetate and water. The organic phase is separated, dried, filtered and evaporated under reduced pressure to give the title compound, m.p. 172° C.

Synthesis Example 5

{4-[2-Chloro-6-(2-methoxy-1-methyl-ethylamino)-pyridin-4-yl]-pyrimidin-2-yl}-(3-chloro-phenyl)-amino Step 1:

A suspension of 2,6-dichloroisonicotinic acid (20.0 g, 0.10 mol) and oxalylchloride (11.2 ml, 0.13 mol) in methylenechloride (100 ml) is stirred at room temperature in the presence of a katalytic amount of dimethylformamide for 2 hours to give a clear solution. The solvent is evaporated under reduced pressure and the residue is added to a well stirred solution of N,O-dimethylhydroxylamine (12.0 g, 0.2 mol) and triethylamine (10.2 g, 0.1 mol) at 0–5° C. After stirring for 2 hours at room temperature the reaction mixture is washed with water. The organic phase is dried over magnesium sulfate, filtered and evaporated under reduced pressure to give 2,6-dichloro-N-methoxy-N-methyl-isonicotinamide in form of colorless crystals, m.p. 69–70° C.

Step 2:

To a solution of 2,6-dichloro-N-methoxy-N-methyl-isonicotinamide (20 g, 0.085 mol) in THF (150 ml) is added at −30° C. a solution of methyl magnesium chloride in THF (0.2 mol) at such a rate that the temperature does not exceed −20° C. After stirring the mixture for an additional hour at −20° C. the mixture is poured on an aqueous, saturated solution of ammonium chloride. The organic phase is separated, dried over magnesium sulfate, filtered and evaporated to dryness.

Step 3:

The crystalline product obtained in step 2 is refluxed in dimethylformamide diethyl acetal (20 ml) for 10 minutes. The reaction mixture is evaporated under reduced pressure to give a dark red oil. The intermediate is refluxed with 3-chlorophenylguanidine hydrogencarbonate (16.2 g, 0.07 mol) in 2-butanol (250 ml) for 1 hour. The product is crystallizing during this time. The crystals are filtered and washed with ether: yellow crystals, m.p. 239–240° C.

Step 4:

The intermediate obtained in step 3 (0.5 g, 1.4 mmol) in 1-methoxy-2-aminopropane (2 ml) is refluxed for 16 hours. The crude product mixture is purified by flash column chromatography to give the crystalline title compound, m.p. 128–129° C.

Synthesis Example 6

[4-(2-Amino-pyridin-4-yl)-pyrimidin-2-yl]-(3-chloro-phenyl)-amine

A suspension of (3-chloro-phenyl)-[4-(2-chloro-pyridin-4-yl)-pyrimidin-2-yl]-amine (10.0 g, 0.03 mol) in dioxane (150 ml) and ammonia (20 g) is heated in an autoclave at 200° C. for 48 hours. The reaction mixture is partitioned between ethyl acetate and water. The organic phase is evaporated under reduced pressure and the product is purified by chromatography on silicagel.

Synthesis Example 7

N'-{4-[2-(3-Chloro-phenylamino)-pyrimidin-4-yl]-pyridin-2-yl}-.N.,.N.-dimethyl-formamidine A mixture of [4-(2-amino-pyridin-4-yl)-pyrimidin-2-yl]-(3-chloro-phenyl)-amine (0.3 g, 1 mmol) and N,N-dimethylformamid diethylacetal (0.3 g, 2 mmol) are heated in dimethylformamide (5 ml) at 120° C. for 1 hour. The temperature is raised to 140° C. and the liberated ethanol is allowed to distill of. After cooling the reaction mixture to room temperature, diethylether is added and the resulting crystals are filtered with suction to give the title compound, m.p. 194–195° C.

Synthesis Example 8

N-{4-[2-(3-Chloro-phenylamino)-pyrimidin-4-yl]-pyridin-2-yl}-propionamide

Propionic acid anhydride (0.26 g, 2.0 mmol) is added to a solution of [4-(2-amino-pyridin-4-yl)-pyrimidin-2-yl]-(3-chloro-phenyl)-amine (0.5 g, 1.68 mmol) and a catalytic amount of DMAP in dimethoxyethane (10 ml) at 95° C. Heating is continued for 1 hour. On cooling the products starts to crystallize. Diethylether is added and the product is filtered of and washed with ether to give the title compound, m.p. 215–216° C.

Synthesis Example 9

{4-[2-(3-Chloro-phenylamino)-pyrimidin-4-yl]-pyridin-2-ylamino}-acetic acid

A mixture of (3-chloro-phenyl)-[4-(2-chloro-pyridin-4-yl)-pyrimidin-2-yl]-amine (10.0 g, 0.03 mol) and glycine (4.8 g, 0.06 ml) in DBU (100 ml) is heated at 150° C. under an atmosphere of argon for 40 hours. The still hot reaction mixture is poured into water. After washing the aqueous phase with ethyl acetate the pH is adjusted to 5 by adding citric acid. The resulting precipiate is filtered and recrystallized from dimethylformamide/ethanol to give the product in form of yellow crystals, m.p. 136–138° C. (with decomposition).

Synthesis Example 10

[4-(2-Allylamino-1-oxy-pyridin-4-yl)-pyrimidin-2-yl]-(3-chloro-phenyl)-amine

To a suspension of [4-(2-allylamino-pyridin-4-yl)-pyrimidin-2-yl]-(3-chloro-phenyl)-amine (1.0 g, 3 mmol) in methylene chloride (10 ml) is added a solution of m-chloroperbenzoic acid (0.73 g, 70%, 3 mmol) in methylen chloride (5 ml) at 5° C. The reaction mixture is stirred at room temperature for 30 minutes, washed with bicarbonate solution and evaporated under reduced pressure. The residue is purified by chromatography to give the title compound, m.p. 223–224° C.

Synthesis Example 11

(3-Chloro-phenyl)-{4-[2-(ethyl-methoxymethyl-amino)-pyridin-4-yl]-pyrimidin-2-yl}-amine Solid potassium-t-butoxide (0.27 g, 2.5 mmol) is added at room temperature to a solution of (3-chloro-phenyl)-[4-(2-ethylamino-pyridin-4-yl)-pyrimidin-2-yl]-amine (0.5 g,1.5 mmol) in dry tetrahydrofurane (15 ml). The resulting solution is cooled to 0° C. and chloromethylmethylether (0.16 g, 2.0 mmol) is added at such a rate that the temperature does not exceed 5° C. After stirring the mixture for 2 hours at room temperature, the solvent is evaporated under reduced pressure and the product is purified by chromatography. The product is obtained in form of slightly yellow crystals, m.p. 114–115° C.

Analogously to the above examples the compounds of tables 1 to 58 and those of the following table 59 may be prepared.

TABLE 59

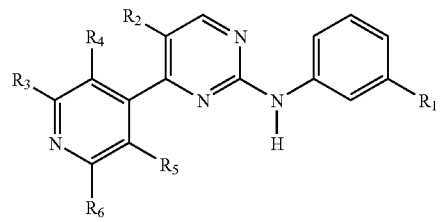

| CN | R1 | R2 | R3 | R4 | R5 | R6 | Addition Salt | m.p. |
|---|---|---|---|---|---|---|---|---|
| 1. | Cl | H | H | H | H | NHCH$_2$CH$_2$NH$_2$ | | 151–156 |
| 2. | Cl | H | H | H | H | NH-(3-tetrahydrofuryl) | | 184–185 |
| 3. | Cl | H | H | H | H | NHCH$_2$COOH | | 136–138 |
| 4. | Cl | H | H | H | H | NHCH(CH$_2$CH$_3$)CH$_2$OCH$_3$ | | Oil |
| 5. | OCF$_2$CHF$_2$ | H | H | H | H | NHCH(CH$_3$)CH$_2$OCH$_3$ | | 116–117 |
| 6. | Cl | H | H | H | Cl | NHCH$_2$OCH$_3$ | | 172 |
| 7. | Cl | H | F | H | H | NHCH(CH$_3$)CH$_2$OCH$_3$ | | 103–105 |
| 8. | Cl | H | H | H | H | NHCH$_2$CH$_2$-(4-morpholinyl) | | 187–188 |
| 9. | Cl | H | H | Cl | F | NHCH(CH$_3$)CH$_2$OCH$_3$ | | 100–101 |
| 10. | Cl | CH$_3$ | Cl | H | H | NHCH(CH$_3$)CH$_2$OCH$_3$ | | 100–101 |
| 11. | Cl | H | Cl | H | H | NHCH(CH$_3$)CH$_2$OCH$_3$ | | 128–129 |
| 12. | Cl | H | H | H | H | NHCH(CH$_3$)CH$_2$OCH$_3$ | HCl | 104–105 (d) |
| 13. | Cl | H | H | H | H | NHCH(CH$_3$)CH$_2$OCH$_3$ | Citric acid | 80–90 (d) |
| 14. | Cl | H | H | H | H | NHCH(CH$_3$)CH$_2$OCH$_3$ | PhSO3H | 103–104 (d) |
| 15. | Cl | H | H | H | H | NHCH(CH$_3$)CH$_2$OCH$_3$ | MeSO3H | 111–112 (d) |
| 16. | Cl | H | H | H | H | NHCH(CH$_3$)CH$_2$CH$_2$-(1-imidazolyl) | | 150–151 |
| 17. | Cl | H | H | H | H | 4-morpholinyl | | 175–176 |
| 18. | Cl | H | H | H | H | NH-(1-amino-2-cyclohexyl) | | >215 |
| 19. | Cl | H | H | H | H | NHCH(CH$_3$)CH$_2$CH$_2$N(CH$_3$)$_2$ | | 147–148 |
| 20. | Cl | H | H | H | H | NHCH$_2$CH$_2$-(4-morpholinyl) | | 171–172 |
| 21. | Cl | H | H | H | H | 1-piperazinyl | | 103–104 |
| 22. | Cl | H | H | H | H | NHNH$_2$ | | 201–203 |
| 23. | Cl | H | H | H | H | NHC(CH$_3$)$_2$CH$_2$CH$_2$OH | | 129–130 |
| 24. | Cl | H | H | H | H | NHC(CH$_3$)$_2$CH$_2$CH$_2$OCH$_3$ | | |
| 25. | Cl | H | H | H | H | NHC(CH$_3$)$_2$CH$_2$CH$_2$OCH$_2$CH$_3$ | | |
| 26. | Cl | H | H | H | H | NHCH$_2$CH$_2$OCH$_2$CH$_3$ | | Oil |
| 27. | Cl | H | H | H | H | NHCH(CH$_2$CH$_2$CH$_3$)CH$_2$OH | | 63–64 |
| 28. | Cl | H | H | H | H | NHC(CH$_3$)$_2$CH$_2$OH | | 139–140 |
| 29. | Cl | H | H | H | H | NHCH$_2$CH(CH$_3$)OCH$_3$ | | |
| 30. | Cl | H | H | H | H | NH CH$_2$CH(CH$_3$)CH$_2$-(1-imidazolyl) | | 203–204 |
| 31. | Cl | H | H | H | H | NHCH(CH$_2$CH$_3$)CH$_2$OH | | 90–91 |
| 32. | Cl | H | H | H | H | NHCH(CH$_3$)CH$_2$OCH$_3$ | | 143–144 |
| 33. | Cl | H | H | H | H | NHCH$_2$CH$_2$-(1-imidazolyl) | | |
| 34. | Cl | H | H | H | H | NHCH$_2$CH$_2$OCH$_3$ | | 161–162 |
| 35. | Cl | H | H | H | H | NHCH(CH$_2$OH)$_2$ | | 129–130 |
| 36. | Cl | H | H | H | H | NHCH$_2$CH(CH$_3$)-(1-imidazolyl) | | 130 |
| 37. | Cl | H | H | H | H | NHCH$_2$CH$_2$OH | | 190–191 |
| 38. | Cl | H | H | H | H | N(CH$_2$OCH$_3$)CH(CH$_3$)CH$_2$OCH$_2$OCH$_3$) | | oil |
| 39. | Cl | H | H | H | H | NHCH(CH$_3$)CH$_2$OH | | 83–85 |
| 40. | Cl | H | H | H | H | NHC(CH$_3$)$_2$CH$_2$OCH$_3$ | | 109 |
| 41. | Cl | H | H | H | H | NHCH(CH[CH$_3$]CH$_2$CH$_3$)CH$_2$OH | | oil |
| 42. | Cl | H | H | H | H | NHCH$_2$CH$_2$CH$_2$NH$_2$ | | 140 |
| 43. | Cl | H | H | H | H | NHCH$_2$CH$_2$CH$_2$-(1-imidazolyl) | | 176–177 |
| 44. | Cl | H | H | H | H | NHCH$_2$CH$_2$-(1,2,4)-triazol-1-yl | | |
| 45. | Cl | H | H | H | H | NHCH$_2$CH$_2$CH$_2$NHCOOCH$_2$CH$_3$ | | 150–151 |
| 46. | Cl | H | H | H | H | NHCH$_2$CH$_2$CH$_2$OH | | 135–142 |

TABLE 59-continued

| CN | R1 | R2 | R3 | R4 | R5 | R6 | Addition Salt | m.p. |
|---|---|---|---|---|---|---|---|---|
| 47. | Cl | H | H | H | H | NHCH$_2$CH$_2$CH$_2$OCH$_3$ | | |
| 48. | Cl | H | H | H | H | NHCH$_2$CH$_2$CH$_2$NH$_2$ | MeSO$_3$H | |
| 49. | Cl | H | H | H | H | NHCH$_2$CH$_2$CH$_2$-(1-imidazolyl) | MeSO$_3$H | |
| 50. | Cl | H | H | H | H | NHCH(CH$_3$)CH$_2$Oac | | 137–138 |
| 51. | Cl | H | H | H | H | NHCH(CH$_2$CH$_3$)CH$_2$OAc | | 125–126 |
| 52. | Cl | H | H | H | H | NHCH$_2$OAc | | 128–129 |
| 53. | Cl | H | H | H | H | NHCH(CH$_2$CH$_3$)CH$_2$OAc | | oil |
| 54. | Cl | H | H | H | H | NHCH(CH$_3$)CH$_2$OCH$_2$CH$_3$ | | |
| 55. | Cl | H | H | H | H | NHCH(CH$_3$)CH(CH$_3$)OCH$_3$ | | |
| 56. | Cl | H | H | H | H | NHCH$_2$CH(CH$_3$)OCH$_3$ | | |
| 57. | Cl | H | H | H | H | NHCH$_2$CH$_2$OCH$_2$OCH$_3$ | | |
| 58. | Cl | H | H | H | H | NH$_2$ | | 214–215 |
| 59. | Cl | H | H | H | H | N(CH$_3$)$_2$ | | 178–179 |
| 60. | Cl | H | H | H | H | NHCH$_2$CH$_3$ | | 201 |
| 61. | Cl | H | H | H | H | NHCOCH$_3$ | | 245–247 |
| 62. | Cl | H | H | H | H | NHCOCH$_2$CH$_2$CH$_3$ | | 185–186 |
| 63. | Cl | H | H | H | H | NHCOCF$_3$ | | 180–181 |
| 64. | Cl | H | H | H | H | NHCH$_3$ | | 196–197 |
| 65. | Cl | H | H | H | H | NHCH(CH$_3$)CH(OCH$_3$)$_2$ | | 121–122 |
| 66. | Cl | H | H | H | H | N=C(CH$_3$)N(CH$_3$)$_2$ | | Oil* |
| 67. | Cl | H | H | H | H | NHCH$_2$CH$_2$CH$_3$ | | 165–166 |
| 68. | Cl | H | H | H | H | NHCH(CH$_3$)$_2$ | | 184–185 |
| 69. | Cl | H | H | H | H | NHCH$_2$CH=CH$_2$ | | 179–180 |
| 70. | Cl | H | H | H | H | NHC(CH$_3$)$_3$ | | 125–126 |
| 71. | Cl | H | H | H | H | NHCH(CH$_3$)CH$_2$CH$_2$-(2-pyridyl) | | 136–137 |
| 72. | Cl | H | H | H | H | N(CH$_3$)NH$_2$ | | 181–183 |
| 73. | Cl | H | H | H | H | NHCH$_2$CH$_2$SO$_2$CH$_3$ | | 164–165 |
| 74. | Cl | H | H | H | H | NHCH$_2$CH$_2$SOCH$_3$ | | 167–168 |
| 75. | Cl | H | H | H | H | NHCH$_2$-(2-tetrahydrofuryl) | | 151–152 |
| 76. | Cl | H | H | H | H | NHCH$_2$CH(CH$_3$)OH | | 152–153 |
| 77. | Cl | H | H | H | H | NHCOCH(OH)CH$_3$ | | 169–170 |
| 78. | Cl | H | H | H | H | NHCH$_2$-(2-furyl) | | 185–186 |
| 79. | Cl | H | H | H | H | NHCH$_2$-(2-pyridyl) | | 145–146 |
| 80. | Cl | H | H | H | H | NH-(3-pyrrolidyl) | | 129–130 |
| 81. | Cl | H | H | H | H | NHCH$_2$CH=C(CH$_3$)$_2$ | | 141–143 |
| 82. | Cl | H | H | H | H | NHCH(CH$_3$)$_2$ | HCl | 88–89 |
| 83. | Cl | H | H | H | H | NH-(4-tetrahydropyranyl) | | 166–167 |
| 84. | Cl | H | H | H | H | NHCH$_2$-(3-tetrahydrofuryl) | | 184–185 |
| 85. | Cl | H | H | H | H | NHCH$_2$CH(CH)$_3$CH$_2$CH$_3$ | | 162–164 |
| 86. | Cl | H | H | H | H | NHCH$_2$CH$_2$OCH$_2$CH$_3$ | | 123–124 |
| 87. | Cl | H | H | H | H | NHCH$_2$CH(OCH$_3$)$_2$ | | 148–149 |
| 88. | Cl | H | H | H | H | NCH$_3$NHCH$_3$ | | |
| 89. | Cl | H | H | H | H | NHCH$_2$CH$_2$NHCOOCH$_2$CH$_3$ | | 148–150 |
| 90. | Cl | H | H | H | H | NHCH$_2$CH$_2$-(2-pyridyl) | | 164–165 |
| 91. | Cl | H | H | H | H | N(CH$_3$)CH$_2$OCH$_3$ | | |
| 92. | Cl | H | H | H | H | NHCOCF$_2$CF$_2$CF$_3$ | | 149–150 |
| 93. | Cl | H | H | H | H | NHCOCF$_2$CF$_3$ | | 172–174 |
| 94. | Cl | H | H | H | H | NHCH$_2$CH$_2$CH$_2$O-(2-pyrimidinyl) | | 93–95 |
| 95. | Cl | H | H | H | H | NHCH(CH$_3$)CH$_2$O-(2-pyrimidinyl) | | 79–80 |
| 96. | Cl | H | H | H | H | NHCOCH$_2$CH$_3$ | | 215–216 |
| 97. | Cl | H | H | H | H | N=CHN(CH$_3$)$_2$ | | 194–195 |
| 98. | Cl | H | H | H | H | N(CH$_2$CH$_3$)CH$_2$OCH$_3$ | | 114–115 |
| 99. | Cl | H | H | H | H | NHCH(CH$_3$)CH$_2$CH$_3$ | | 198–199 |
| 100. | Cl | H | H | H | H | NHCH$_2$CH$_2$CH$_2$Si(OCH$_3$)$_3$ | | 144–146 |
| 101. | Cl | H | H | H | H | N(NH$_2$) CH$_2$CH$_2$OH | | |
| 102. | Cl | H | H | H | H | NHCH$_2$-(3-pyridyl) | | 166–167 |
| 103. | Cl | H | H | H | H | NHCH$_2$CF$_3$ | | 222–223 |
| 104. | Cl | H | H | H | H | N(CH$_3$)N(Ac)$_2$ | | 197–199 |
| 105. | Cl | H | H | H | H | N(CH$_3$)NHAc | | 210–212 |
| 106. | Cl | H | H | H | H | NHCH$_2$CH$_2$CH$_2$OCOCH$_2$CH$_3$ | | |
| 107. | Cl | H | H | H | H | NHCH(CH$_3$)CH$_2$SCH$_3$ | | 149–150 |
| 108. | Cl | H | H | H | H | NHCH$_2$CH$_2$SCH$_3$ | | 148–149 |
| 109. | Cl | H | H | H | H | NHCH(CH$_3$)CH$_2$SOCH$_3$ | | |
| 110. | Cl | H | H | H | H | N=C(CH$_3$)N(CH$_2$CH$_3$)$_2$ | | |

TABLE 59-continued

| CN | R1 | R2 | R3 | R4 | R5 | R6 | Addition Salt | m.p. |
|---|---|---|---|---|---|---|---|---|
| 111. | Cl | H | H | H | H | N=C(CH$_3$)N(CH$_3$)CH$_2$CH$_3$ | | |
| 112. | Cl | H | H | H | H | N=C(CH$_3$)N(CH$_2$CH$_3$)$_2$ | | |
| 113. | Cl | H | H | H | H | NHS(O)N(CH$_3$)$_2$ | | |
| 114. | Cl | H | H | H | H | NHC(O)N(CH$_3$)$_2$ | | |
| 115. | Cl | H | H | H | H | NHCH(CH$_3$)C=CHCH$_3$ | | |
| 116. | Cl | H | H | H | H | NHCH(CH$_3$)C=C(CH$_3$)$_2$ | | |
| 117. | Cl | H | H | H | H | NHCH$_2$C≡CH | | |
| 118. | Cl | H | H | H | H | NHCH(CH$_3$)C≡CH | | |
| 119. | Cl | H | H | H | H | NHCON(CH$_2$CH$_3$)$_2$ | | |
| 120. | Cl | H | H | H | H | NHCOOCH$_3$ | | |
| 121. | Cl | H | H | H | H | NHCOOCH$_2$CH$_3$ | | 247–248 |
| 122. | Cl | H | H | H | H | N=C(NH$_2$)NH$_2$ | | |
| 123. | Cl | H | H | H | H | N=CHN(CH$_2$CH$_3$)$_2$ | | |
| 124. | Cl | H | H | H | H | NHC(CH$_3$)$_2$CH$_2$SCH$_3$ | | |
| 125. | Cl | H | H | H | H | NH-(3-tetrahydrofuryl) | HCl | 215–216 |
| 126. | Cl | H | H | H | H | NHCH$_2$-(3-furyl) | | 174–177 |
| 127. | Cl | H | H | H | H | NHCH(CH$_3$)$_2$ | MeSO$_3$H | |
| 128. | Cl | H | H | H | H | NHCH(CH$_3$)$_2$ | Cltric acid | |
| 129. | Cl | H | H | H | H | (4,4-dimethyl oxazolidinyl) | | 138–139 |
| 130. | Cl | H | H | H | H | NHCH$_2$CH(CH$_2$CH$_3$)CH$_2$CH$_2$CH$_3$ | | 140–141 |
| 131. | Cl | H | H | H | H | NHCH$_2$CH$_2$-(4-imidazolyl) | Tartaric acid | solid |
| 132. | Cl | H | H | H | H | NHCH$_2$CH$_2$C(CH$_3$)$_2$OH | | solid |
| 133. | Cl | H | H | H | H | NHCH$_2$CH$_2$CO (1-[4-ETHYLPIPERAZINYL]) | | |
| 134. | Cl | H | H | H | H | NH-CH$_2$CH$_2$-C(O)-N(4-ethylpiperazinyl) | | solid |
| 135. | Cl | H | H | H | H | NH-CH$_2$CH$_2$-C(O)-pyrrolidinyl | | solid |
| 136. | Cl | H | H | H | H | NHCH$_2$CH$_2$COOMe | | solid |
| 137. | Cl | H | H | H | H | NH-CH$_2$CH$_2$-C(O)-N(4-isopropylpiperazinyl) | | solid |
| 138. | Cl | H | H | H | H | NHCH$_2$CH$_2$CONHC(CH$_3$)$_3$ | | solid |
| 139. | Cl | H | H | H | H | NHCH$_2$CH$_2$CONHCH$_2$CH$_3$ | | solid |
| 140. | Cl | H | H | H | H | NHCH$_2$CH$_2$CONH(CH$_2$CH$_3$)$_2$ | | solid |
| 141. | Cl | H | H | H | H | NHCH$_2$CH$_2$COOCH(CH$_3$)$_2$ | | solid |
| 142. | Cl | H | H | H | H | NH-CH$_2$CH$_2$-C(O)-piperidinyl | | solid |

TABLE 59-continued

[Structure: pyridine-pyrimidine-NH-phenyl core with R1-R6 substituents]

| CN | R1 | R2 | R3 | R4 | R5 | R6 | Addition Salt | m.p. |
|---|---|---|---|---|---|---|---|---|
| 143. | Cl | H | H | H | H | NH-CH₂CH₂-C(O)-N(piperazine-N-methyl) | | solid |
| 144. | Cl | H | H | H | H | NH-CH₂CH₂-C(O)-N(morpholine) | | solid |
| 145. | Cl | H | H | H | H | NHCH₂CH₂COOCH₂CH₃ | | solid |
| 146. | Cl | H | H | H | H | NHCH₂CH₂CH₂COOH | | solid |
| 147. | Cl | H | H | H | H | NHCH₂CH₂-(2-thienyl) | | solid |
| 148. | Cl | H | H | H | H | N(CH₃)CH₂CH₂NH₂ | | solid |
| 149. | Cl | H | H | H | H | NHCH₂CH₂N(CH(CH3)₂)₂ | | solid |
| 150. | Cl | H | H | H | H | NHCH₂CH₂CONHOCH₃ | | solid |
| 151. | Cl | H | H | H | H | NHCH₂CH₂CH₂CH₂NH₂ | | solid |
| 152. | Cl | H | H | H | H | NHCH₂CH₂SO₃H | | solid |
| 153. | Cl | H | H | H | H | NHCH₂CH₂NHCH₃ | MeSO3H | solid |
| 154. | Cl | H | H | H | H | NHCH₂CH₂NH₂ | MeSO3H | solid |
| 155. | Cl | H | H | H | H | N(C(O)NH₂)-CH₂CH₂CH₂-NH-C(O)NH₂ | | solid |
| 156. | Cl | H | H | H | H | NHCH₂CH₂NHCH(CH₃)₂ | | solid |
| 157. | Cl | H | H | H | H | NHCH₂CH₂NHCH₂CH₃ | MeSO3H | solid |
| 158. | Cl | H | H | H | H | NHCH₂CH₂CH₂(4-triazolyl) | MeSO3H | solid |
| 159. | Cl | H | H | H | H | NH-cyclohexyl | | 191–192 |
| 160. | Cl | H | H | H | H | NH-CH₂CH₂CH₂-O-(2-thiazolyl-4-CF₃-5-CN) | | 240–241 |
| 161. | Cl | H | H | H | H | NHCH₂CH₂CH₂NHCOCF₃ | | solid |
| 162. | Cl | H | H | H | H | NHCH₂CH₂CH₂NH(2-pyrimidyl) | | 186–188 |
| 163. | Cl | H | H | H | H | NHCH₂CH₂CH₂NHCOCH₂CH₃ | | 171–172 |
| 164. | Cl | H | H | H | H | NHCH₂CH₃ | MeSO3H | solid |
| 165. | Cl | H | H | H | H | NHCH(CH₃)CH₂OCOOCH₂CH₃ | | 102–103 |
| 166. | Cl | H | H | H | H | NHCH₂CH₂CH₂(1-triazolyl) | | 149–150 |
| 167. | Cl | H | H | H | H | NH-CH(CH₂CH₃)-CH₂OH | | 90–91 |
| 168. | Cl | H | H | H | H | NH-CH(CH(CH₃)₂)-CH₂OH | | 139–140 |
| 169. | Cl | H | H | H | H | N(CH₃)CH₂OCH₃ | | |

TABLE 59-continued
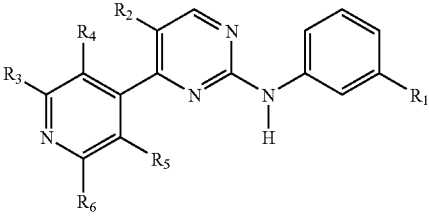
| CN | R1 | R2 | R3 | R4 | R5 | R6 | Addition Salt | m.p. |
|---|---|---|---|---|---|---|---|---|
| 170. | Cl | H | H | H | H | NHCH₂CH₂CH₃ | | |
| | Cl | H | H | H | H | 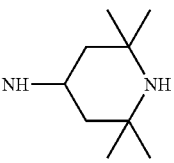 | | 214–215 |
| 171. | Cl | H | H | H | H | 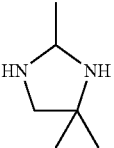 | | solid |
| 172. | Cl | H | H | H | H | 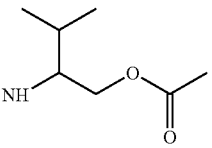 | | oil |
| 173. | Cl | H | H | Cl | F | N(CH₃)₂ | | 138–139 |
| 174. | Cl | H | H | H | Cl | N(CH₃)₂ | | 165–167 |
| 175. | Cl | H | F | H | H | NHCH(CH₃)₂ | | 174–175 |
| 176. | Cl | H | H | H | H | 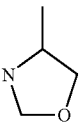 | | 143–144 |
| 177. | Cl | H | H | H | H |  | | 178–179 |
| 178. | Cl | H | H | H | H | 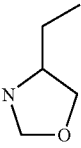 | | 123–124 |
| 179. | Cl | H | H | H | H | 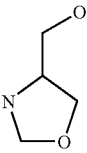 | | 119–120 |
| 180. | Cl | H | H | H | H | NH(CH₂)₅CO₂CH₃ | | 112–115 |
| 181. | Cl | H | H | H | H | NHCH(CH₃)CH₂OCO₂CH₃ | | 112–113 |
| 182. | Cl | H | H | H | H | NHNHCOCH₃ | | 205 |
| 183. | Cl | H | H | H | H | NHCH(CH₃)CO₂CH₃ | | oil |
| 184. | Cl | H | H | H | H | NHCH₂CH₂C(CH₃)₃ | | 176–178 |
| 185. | Cl | H | H | H | H | NHCH₂CH₂CH(CH₃)CH₂C(CH₃)₃ | | 155–156 |

TABLE 59-continued

| CN | R1 | R2 | R3 | R4 | R5 | R6 | Addition Salt | m.p. |
|---|---|---|---|---|---|---|---|---|
| 186. | Cl | H | H | H | H | NHCH(CH₃)CH₂OCHO | | 119–121 |
| 187. | Cl | H | H | H | H | NHCOCH₂OCH₃ | | 164 |
| 188. | Cl | H | H | H | H | NHSO₂CH₃ | | 245 |
| 189. | Cl | H | H | H | H | NHCH(CH₃)CO₂CH(CH₃)₂ | | oil |
| 190. | Cl | H | H | H | H | N[(CH₂)₃OCO₂CH₂CH₃]CO₂CH₂CH₃ | | solid |
| 191. | Cl | H | H | H | H | CH₂CH₂COOH | | |
| 192. | Cl | H | H | H | H | NHCH₂CH₂NHCH₂CH₃ | | |
| 193. | Cl | H | H | H | H | NHCH₂CH₂CH₂-(1,2,4)-triazol-1-yl | | |
| 194. | Cl | H | H | H | H | NHCH₂CO₂CH₃ | | 164 |
| 195. | Cl | H | H | H | H | NHCH(CH₃)CO₂CH₂CH₃ | | oil |
| 196. | Cl | H | H | H | H | NHCH₂CH(CH₃)CO₂CH₂CH₃ | | oil |
| 197. | Cl | H | H | H | H | [tetrahydrofuran-2,5-dimethoxy with NHCH₂ substituent] | | 155–161 |
| 198. | Cl | H | H | H | H | [2,2-dimethyl-3-(tert-butoxycarbonyl)oxazolidin-4-yl-CH₂NH] | | 193–197 |
| 199. | Cl | H | H | H | H | NHCH₂CH(CH₃)CO₂CH₃ | | oil |
| 200. | Cl | H | H | H | H | NHCH₂CH₂CH(OH)CH(OH)CH₂OH | | 133–139 |
| 201. | Cl | H | H | H | H | NHCH(CH₃)CO₂CH₂CH₃ | | 136–137 |
| 202. | Cl | H | H | H | H | NHCH₂CONHCH₃ | | 191–192 |
| 203. | Cl | H | H | H | H | NHCH(CH₃)CONHCH₃ | | 205 |
| 204. | Cl | H | H | H | H | NH(CH₂)₄OH | | |
| 205. | Cl | H | H | H | H | [4-(2-aminoethyl)piperazin-1-yl] | | |
| 206. | Cl | H | H | H | H | NH(CH₂)₃NHCH₂CH₂OH | | |
| 207. | Cl | H | H | H | H | NHCH₂CH₂-(4-imidazolyl) | | |
| 208. | Cl | H | H | H | H | NH(CH₂)₅OH | | |
| 209. | Cl | H | H | H | H | N[(CH₂)₃OCONH₂]CONH₂ | | |
| 210. | Cl | H | H | H | H | N(CH₃)CH₂CH₂OH | | |
| 211. | Cl | H | H | H | H | N(CH₂CH₂OH)₂ | | |
| 212. | Cl | H | H | H | H | [cyclopropylmethyl-NH] | | |
| 213. | Cl | H | H | H | H | NH(CH₂)₃OCH(CH₃)₂ | | |
| 214. | Cl | H | H | H | H | NH(CH₂)₃N(CH₃)₂ | | |
| 215. | Cl | H | H | H | H | NH(CH₂)₃OCH₂CH₃ | | |
| 216. | Cl | H | H | H | H | [3-(aminomethyl)cyclohexanecarboxylic acid] | | |

TABLE 59-continued

| CN | R1 | R2 | R3 | R4 | R5 | R6 | Addition Salt | m.p. |
|---|---|---|---|---|---|---|---|---|
| 217. | Cl | H | H | H | H | NHCH$_2$-(4-pyridyl) | | |
| 218. | Cl | H | H | H | H | NHCH$_2$CH$_2$-(1-piperidinyl) | | |
| 219. | Cl | H | H | H | H | NH(CH$_2$)$_3$N(CH$_2$CH$_3$)$_2$ | | |
| 220. | Cl | H | H | H | H | NH(CH$_2$)$_2$N(CH$_2$CH$_3$)$_2$ | | |
| 221. | Cl | H | H | H | H | NH(CH$_2$)$_2$N(CH$_3$)$_2$ | | |
| 222. | Cl | H | H | H | H | NHCH$_2$CH$_2$-(1-pyrrolidinyl) | | |
| 223. | Cl | H | H | H | H | NHCH$_2$CH$_2$CONH$_2$ | | |
| 224. | Cl | H | H | H | H | NHCH$_2$CH$_2$CON(CH$_3$)$_2$ | | |
| 225. | Cl | H | H | H | H | 4-hydroxypiperidin-1-yl | | |
| 226. | Cl | H | H | H | H | NHCH$_2$CH$_2$CONHCH$_2$CH$_2$CH$_3$ | | |
| 227. | Cl | H | H | H | H | NHCH$_2$CH$_2$CONHCH$_2$Ph | | |
| 228. | Cl | H | H | H | H | NHCH$_2$CH$_2$CONH(c-Hexyl) | | |
| 229. | Cl | H | H | H | H | NHCH$_2$C(O)-(4-ethylpiperazin-1-yl) | | |
| 230. | Cl | H | H | H | H | NHCH$_2$CON(CH$_2$CH$_3$)$_2$ | | |
| 231. | Cl | H | H | H | H | NHCH$_2$C(O)-(piperidin-1-yl) | | |
| 232. | Cl | H | H | H | H | NHCH$_2$CH$_2$CONHOH | | |
| 233. | Cl | H | H | H | H | NHCH$_2$CH$_2$NHCH$_3$ | | |
| 234. | Cl | H | H | H | H | NHCH$_2$CH$_2$CH$_2$NHSO$_2$CH$_3$ | | |
| 235. | Cl | H | H | H | H | NHCH$_2$CH$_2$CH$_2$NHCOCH$_3$ | | |
| 236. | Cl | H | H | H | H | NHCH$_2$CH$_2$CH$_2$NHCOOH(CH$_3$)$_2$ | | |
| 237. | Cl | H | H | H | H | NHCH$_2$CH$_2$CH$_2$NHCONH$_2$ | | |
| 238. | Cl | H | H | H | H | NHCH(CH$_3$)CONHCH$_2$CH$_3$ | | 173–174 |
| 239. | Cl | H | H | H | H | 1-methyl-2-iminopyrrolidinyl | | 130 |
| 240. | Cl | H | H | H | H | NHCH(CH$_3$)CH$_2$OH | | 122–123 |
| 241. | Cl | H | H | H | H | N(COCF$_3$)CH(CH$_3$)CH$_2$OCH$_3$ | | oil |
| 242. | Cl | H | H | H | H | N(CO$_2$CH$_3$)CH(CH$_3$)CH$_2$OCH$_3$ | | |
| 243. | Cl | H | H | H | H | N(CHO)N(CH$_3$)CO$_2$C(CH$_3$)$_3$ | | solid |
| 244. | Cl | H | H | H | H | NHN(CH$_3$)COCH$_3$ | | solid |
| 245. | Cl | H | H | H | H | NHCH$_2$CH$_2$NHAc | | |
| 246. | Cl | H | H | H | H | NHCH$_2$-(3-pyridyl) | | |
| 247. | Cl | H | H | H | H | NH(CH$_2$)$_3$OH | MeSO$_3$H | |
| 248. | Cl | H | H | H | H | NHCH$_2$CH$_2$COOH | Na | |
| 249. | Cl | H | H | H | H | NH(CH$_2$)$_3$NHCH$_2$CH$_2$OH | MeSO$_3$H | |
| 250. | Cl | H | H | H | H | NHCH$_2$CH$_2$-(1-imidazolyl) | MeSO$_3$H | |
| 251. | Cl | H | H | H | H | NHCH$_2$CH$_2$NHCH(CH$_3$)$_2$ | MeSO$_3$H | |

TABLE 59-continued

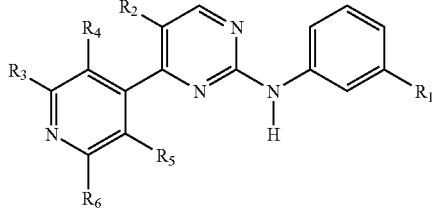

| CN | R1 | R2 | R3 | R4 | R5 | R6 | Addition Salt | m.p. |
|---|---|---|---|---|---|---|---|---|
| 252. | Cl | H | H | H | H | 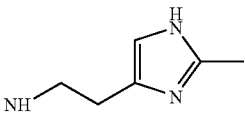 | | |
| 253. | Cl | H | H | H | H | 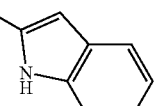 | | |
| 254. | Br | H | H | H | H | NH(CH$_2$)$_3$OH | | 144–146 |
| 255. | Br | H | H | H | H | NH(CH$_2$)$_3$OCH$_3$ | | 132–134 |
| 256. | F | H | H | H | H | NH(CH$_2$)$_3$OH | | 153–156 |
| 257. | CH$_3$ | H | H | H | H | NH(CH$_2$)$_3$OH | | 128–130 |
| 258. | CF$_3$ | H | H | H | H | NH(CH$_2$)$_3$OH | | 155–156 |
| 259. | CH$_3$O | H | H | H | H | NH(CH$_2$)$_3$OH | | 126–129 |
| 260. | CH$_3$S | H | H | H | H | NH(CH$_2$)$_3$OH | | 98–1 00 |
| 261. | NO$_2$ | H | H | H | H | NH(CH$_2$)$_3$OH | | 152–155 |
| 262. | Ac | H | H | H | H | NH(CH$_2$)$_3$OH | | 125–128 |
| 263. | CF$_3$ | H | H | H | H | NH(CH$_2$)$_3$OCH$_3$ | | 144–147 |
| 264. | ClCF$_2$O | H | H | H | H | NHCH(CH$_3$)CH$_2$OCH$_3$ | | |
| 265. | ClCF$_2$O | H | H | H | H | NHCH$_2$CH$_2$OH | | 151–153 |
| 266. | OCF$_2$CHF$_2$ | H | H | H | H | NH(CH$_2$)$_3$OH | | |
| 267. | OCF$_2$CHF$_2$ | H | H | H | H | NH(CH$_2$)$_3$OCH$_3$ | | |
| 268. | CF$_3$ | H | H | H | H | NH(CH$_2$)$_2$NH$_2$ | | |
| 269. | OCF$_2$CHF$_2$ | H | H | H | H | NH(CH$_2$)$_4$NH$_2$ | | |
| 270. | CO$_2$H | H | H | H | H | NH(CH$_2$)$_3$OH | | |
| 271. | CO$_2$CH$_3$ | H | H | H | H | NH(CH$_2$)$_3$OH | | |
| 272 | CF$_3$ | H | H | H | H | NHCH(CH$_3$)CH$_2$OH | | 142–143 |
| 273 | AcNH | H | H | H | H | NHCH(CH$_3$)CH$_2$OAc | | 163 |
| 274 | CH$_3$ | H | H | H | H | NHCH(CH$_3$)CH$_2$OH | | 80–81 |
| 275 | CH$_3$ | H | H | H | H | NHCH$_2$CH$_3$ | | |
| 276 | OCF$_2$CHF$_2$ | H | H | H | H | NHCH$_2$CH$_2$OH | | |
| 277 | Cl | H | H | H | H | 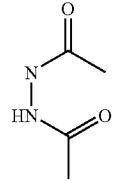 | | 201–205 |
| 278 | Cl | H | H | H | H | NHN(COCH$_3$)$_2$ | | 210 |
| 279 | Cl | H | H | H | H | 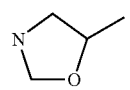 | | 166–167 |
| 280 | Cl | H | H | H | H | NHCH$_2$CH$_2$CH$_2$OCOOCH$_2$CH$_3$ | | 148–150 |

(d) = under decomposition; CN = compound number

Biological Examples

Using the biological assays B-1 to B-12 described above, the tests are carried out employing compounds, or their salts, from Table 59 given above. Plus "+" in the following table means that the activity observed in the corresponding test system is 70% or more.

TABLE 60

| CN | B1 | B2 | B5 | B6 | B7 | B8 | B9 | B10 | B11 | B12 |
|---|---|---|---|---|---|---|---|---|---|---|
| 1 |   |   |   |   |   |   |   | + |   |   |
| 2 | + |   |   |   |   |   |   | + |   | + |
| 3 |   |   |   |   |   | + |   | + |   | + |
| 4 |   |   |   | + |   | + | + |   | + | + |
| 5 |   |   |   |   |   | + |   | + |   | + |
| 6 |   |   |   |   |   |   |   |   |   |   |
| 7 |   |   | + | + |   |   | + |   |   |   |
| 8 |   |   |   | + |   | + |   |   |   |   |
| 9 |   |   |   |   |   |   |   |   |   |   |
| 10 |   |   |   |   |   |   |   |   |   |   |
| 11 |   |   |   |   |   |   |   |   |   |   |
| 12 | + |   | + | + | + | + | + | + |   | + |
| 13 | + |   | + | + | + | + |   | + |   | + |
| 14 |   |   |   | + | + | + |   | + |   | + |
| 15 | + |   |   | + | + | + |   | + |   | + |
| 16 |   |   |   |   |   | + |   | + |   | + |
| 17 |   |   |   |   |   |   |   |   |   |   |
| 18 |   |   |   |   |   |   |   |   |   |   |
| 19 |   |   |   |   |   | + |   |   |   |   |
| 20 |   |   |   | + |   | + |   | + |   | + |
| 21 |   |   |   |   |   |   |   |   |   |   |
| 22 |   |   |   |   |   |   |   | + |   |   |
| 23 |   |   |   |   |   |   |   |   |   |   |
| 24 |   |   |   |   |   |   |   |   |   |   |
| 25 |   |   |   |   |   |   |   |   |   |   |
| 26 |   |   |   |   | + | + |   | + |   | + |
| 27 |   |   |   |   | + | + |   | + |   | + |
| 28 |   |   | + |   | + | + |   | + |   | + |
| 29 |   |   |   |   |   |   |   |   |   |   |
| 30 |   |   |   | + |   | + |   | + |   | + |
| 31 | + | + | + |   | + | + |   | + | + |   |
| 32 | + |   | + | + | + | + | + | + |   | + |
| 33 |   |   |   |   |   |   |   |   |   |   |
| 34 |   |   |   |   | + | + |   | + | + | + |
| 35 |   |   |   | + | + | + |   | + |   |   |
| 36 |   |   |   |   |   |   |   | + |   |   |
| 37 |   |   |   | + | + | + | + | + |   | + |
| 38 |   |   |   | + |   |   |   | + |   | + |
| 39 | + |   |   |   | + | + | + | + |   | + |
| 40 |   |   |   |   |   |   |   |   |   |   |
| 41 |   |   |   | + |   | + |   | + |   |   |
| 42 |   |   |   |   |   | + |   | + | + | + |
| 43 |   |   |   |   | + | + | + | + |   | + |
| 44 |   |   |   |   |   |   |   |   |   |   |
| 45 |   |   |   |   |   |   |   |   |   |   |
| 46 | + |   |   |   |   |   | + | + |   | + |
| 47 |   |   |   |   |   |   |   |   |   |   |
| 48 |   |   |   |   |   | + |   | + |   | + |
| 49 |   |   |   |   | + | + |   | + |   | + |
| 50 |   |   | + | + | + | + | + | + |   | + |
| 51 |   |   |   |   |   |   |   | + |   | + |
| 52 |   |   |   |   |   |   |   | + |   | + |
| 53 |   |   |   |   |   | + |   |   |   |   |
| 54 |   |   |   |   |   |   |   |   |   |   |
| 55 |   |   |   |   |   |   |   |   |   |   |
| 56 |   |   |   |   |   |   |   |   |   |   |
| 57 |   |   |   |   |   |   |   |   |   |   |
| 58 | + |   | + | + | + | + |   | + |   | + |
| 59 |   |   |   | + |   |   |   | + |   | + |
| 60 | + |   | + |   | + |   |   | + |   | + |
| 61 |   |   |   |   |   |   | + |   |   |   |
| 62 |   |   |   |   |   |   |   | + |   | + |
| 63 |   |   | + |   | + | + | + | + |   | + |
| 64 |   | + |   |   |   | + |   | + |   | + |
| 65 |   |   |   | + | + | + | + | + |   | + |
| 66 |   |   |   | + | + | + | + | + | + | + |
| 67 |   |   |   |   |   |   |   |   |   |   |
| 68 | + |   |   |   | + |   | + | + |   | + |
| 69 |   |   | + |   | + | + |   | + |   | + |
| 70 |   |   |   |   |   | + |   | + |   | + |
| 71 |   |   |   |   |   |   |   | + |   | + |
| 72 |   |   |   |   |   |   |   |   |   |   |
| 73 |   |   |   |   |   |   |   |   |   |   |
| 74 |   |   |   |   |   |   |   |   |   | + |
| 75 | + |   | + |   | + | + |   | + |   | + |
| 76 |   |   |   |   |   |   |   | + |   | + |
| 77 |   |   |   |   |   |   |   |   |   |   |
| 78 |   |   |   |   |   | + |   | + |   |   |
| 79 |   |   |   |   |   | + |   | + |   |   |
| 80 |   |   |   |   |   |   |   |   |   |   |
| 81 |   |   |   |   | + | + |   | + |   | + |
| 82 | + |   |   |   |   | + |   | + |   | + |
| 83 |   |   |   |   |   | + |   | + | + | + |
| 84 |   |   |   |   |   | + |   | + |   | + |
| 85 |   |   |   |   |   |   |   |   |   |   |
| 86 |   |   |   |   |   |   |   |   |   |   |
| 87 |   |   |   |   |   |   |   | + |   | + |
| 88 |   |   |   |   |   |   |   |   |   |   |
| 89 |   |   |   |   |   |   |   |   |   |   |
| 90 |   |   |   |   |   | + |   | + |   |   |
| 91 |   |   |   |   |   |   |   | + |   | + |
| 92 |   |   |   |   |   |   |   |   |   |   |
| 93 |   |   |   |   | + | + |   | + |   |   |
| 94 | + |   |   |   |   | + |   | + |   |   |
| 95 |   |   |   | + |   |   |   | + |   | + |
| 96 |   |   |   | + |   |   |   | + |   | + |
| 97 |   |   |   |   |   | + |   | + |   | + |
| 98 |   |   |   |   |   | + |   |   |   |   |
| 99 |   |   |   |   |   |   |   |   |   |   |
| 100 |   |   |   |   |   | + |   |   |   |   |
| 101 |   |   |   |   |   |   |   |   |   |   |
| 102 |   |   |   |   |   | + |   | + |   |   |
| 103 |   |   |   |   | + |   |   | + |   | + |
| 104 |   |   |   |   |   |   |   |   |   |   |
| 105 |   |   |   |   |   |   |   |   |   |   |
| 106 |   |   |   |   |   | + |   | + |   | + |
| 107 |   |   |   |   |   |   |   |   |   |   |
| 108 |   |   |   |   |   |   |   |   |   |   |
| 109 |   |   |   |   |   |   |   |   |   |   |
| 110 |   |   |   |   |   |   |   |   |   |   |
| 111 |   |   |   |   |   |   |   |   |   |   |
| 112 |   |   |   |   |   |   |   |   |   |   |
| 113 |   |   |   |   |   |   |   |   |   |   |
| 114 |   |   |   |   |   |   |   |   |   |   |
| 115 |   |   |   |   |   |   |   |   |   |   |
| 116 |   |   |   |   |   |   |   |   |   |   |
| 117 |   |   |   |   |   |   |   |   |   |   |
| 118 |   |   |   |   |   |   |   |   |   |   |
| 119 |   |   |   |   |   |   |   |   |   |   |
| 120 |   |   |   |   |   |   |   |   |   |   |
| 121 |   |   |   |   |   |   |   | + | + |   |
| 122 |   |   |   |   |   |   |   |   |   |   |
| 123 |   |   |   |   |   |   |   |   |   |   |
| 124 |   |   |   |   |   |   |   |   |   |   |
| 125 |   |   |   |   |   | + |   | + | + | + |

What is claimed is:

1. A process for protecting a plant against attack or infestation by a phytopathogenic organism, comprising applying at least one compound of the formula I,

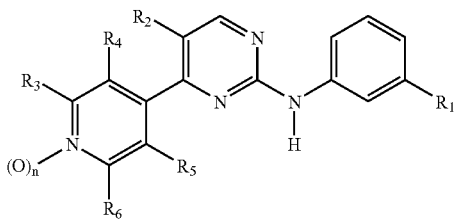

(I)

wherein n is 0 or 1,

R₁ is halogen, alkoxy, haloalkyl, haloalkoxy or alkyl,

R₂ is hydrogen, halogen, alkyl, haloalkyl, alkoxy or haloalkoxy, each of R₃, R₄ and R₅ is, independently of the others, hydrogen, lower alkyl or halogen, and R₆ is a) hydrazino, that is unsubstituted or one- to threefold substituted by optionally substituted alkyl and/or optionally substituted acyl, b) cyclohexylamino, tetrahydro-4H-pyranyl-4-amino, pyrrolidine-3-amino, 2- or 3-tetrahydrofurylamino, all optionally substituted by amino, hydroxy, alkoxy, alkyl or alkoxyalkyl, c) piperazinyl that is optionally substituted by amino, amino-lower alkyl, hydroxy, alkoxy, alkyl or alkoxyalkyl, d) morpholinyl that is optionally substituted by amino, amino-lower alkyl, hydroxy, alkoxy, alkyl or alkoxyalkyl, e) oxazolidinyl that is optionally substituted by amino, amino-lower alkyl, hydroxy, hydroxy-lower alkyl, alkoxy, alkyl or alkoxyalkyl, f) thiazolidinyl that is optionally substituted by amino, amino-lower alkyl, hydroxy, hydroxy-lower alkyl, alkoxy, alkyl or alkoxyalkyl, g) imidazolidinyl that is optionally substituted by amino, amino-lower alkyl, hydroxy, hydroxy-lower alkyl, alkoxy, alkyl or alkoxyalkyl, h) amino or mono- or di-(lower alkyl)amino wherein the lower alkyl moieties are unsubstituted or substituted by one or more substituents independently selected from the group consisting of unsubstituted amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo bound to a carbon that is not directly bound to a heteroatom, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfinyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl, formylpiperazinyl, optionally substituted heteroaryl and optionally substituted heteroaryloxy, i) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylamino sulfonylamino, optionally substituted mono- or di-alkylaminosulfoxylamino, j) N-(optionally substituted alkyl)-N-(optionally substituted lower alkanoyl)-amino, k) N-(optionally substituted alkyl)-N-(optionally substituted alkoxycarbonyl)-amino, l) N-(optionally substituted alkyl)-N—(N',N'-mono- or di-[optionally substituted alkyl]-aminocarbonyl)-amino, or m) N=C(R₇,R₈) wherein R₇ is hydrogen, alkyl, amino, mono- or di-alkylamino and R₈ is amino, mono- or dialkylamino or wherein R₇ and R₈, together with the binding carbon atom, form a saturated five- to seven-membered ring with 0, 1 or 2 ring nitrogen atoms that is optionally substituted by one or more substituents;

or a salt thereof;

to one or more loci selected from the group consisting of a plant, a part of a plant, seeds and the site of a plant.

2. A process according to claim 1, wherein the phytopathogenic organism is a fungal organism.

3. A process according to claim 1, wherein the fungal organism is one or more selected from the group of classes consisting of Ascomycetes, Basidiomycetes, Oomycetes and *Fungi imperfecti*.

4. A process according to claim 1 wherein the phytopathogenic organism is a bacterium.

5. A process according to claim 1 wherein the phytopathogenic organism is a virus.

6. A process according to claim 1 wherein the phytopathogenic organism is a nematode.

7. A process according to claim 1 wherein a compound of formula I is applied wherein n is 0 or 1, R₁ is halogen, haloalkyl or haloalkoxy, R₂ is hydrogen or alkyl, each of R₃, R₄ and R₅ is, independently of the others, hydrogen, lower alkyl or halogen, and R₆ is as defined in claim 1.

8. A process according claim 1 wherein a compound of formula I is applied wherein n is 0 or 1, R₁ is halogen, haloalkyl or haloalkoxy, R₂ is hydrogen or alkyl, each of R₃, R₄ and R5 is hydrogen, and R₆ is as defined in claim 1.

9. A process according to claim 1 wherein a compound of formula I is applied wherein n is 0

R₁ is chloro, trifluoromethyl, trifluoromethoxy or 1,1,2,2-tetrafluoroethoxy

R₂, R₃, R₄ and R₅ are hydrogen, and

R₆ is
(a) hydrazino, that is unsubstituted or one- to threefold substituted by optionally substituted alkyl and/or optionally substituted acyl,
(e) amino or mono- or di-(lower alkyl)amino wherein the lower alkyl moieties are unsubstituted or substituted by one or more substitutents independently selected from the group con-sisting of unsubstituted amino, N-mono- or N,N-di-(lower alkyl)-amino, (lower alkoxy)-lower alk-oxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo bound to a carbon that is not directly bound to a heteroatom, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfinyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl, formylpiperazinyl, optionally substituted heteroaryl and optionally substituted heteroaryloxy,
f) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino,
g) N-(optionally substituted alkyl)-N-(optionally substituted lower alkanoyl)-amino,
h) N-(optionally substituted alkyl)-N-(optionally substituted alkoxycarbonyl)-amino,
i) N-(optionally substituted alkyl)-N—(N',N'-mono- or di-[optionally substituted alkyl]-aminocarbonyl)-amino, or
j) N=C(R₇, R₈) wherein R₇ is hydrogen, alkyl, amino, mono- or di-alkylamino and R₈ is amino, mono- or dialkylamino or wherein R₇ and R₈, together with the binding carbon atom, form a saturated five- to seven-membered ring with 0, 1 or 2 ring nitrogen atoms that is optionally substituted by one or more substituents;

or a salt thereof.

10. A compound of the formula I,

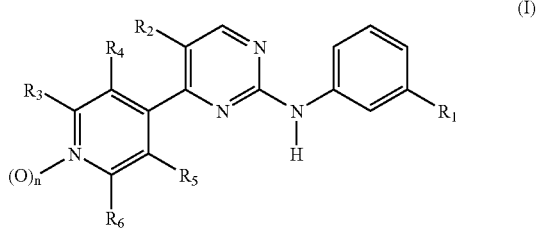

(I)

wherein n is 1,

R₁ is halogen, alkoxy, haloalkyl, haloalkoxy or alkyl,

R₂ is hydrogen, halogen, alkyl, haloalkyl, alkoxy or haloalkoxy, each of R₃, R₄ and R₅ is, independently of the others, hydrogen, lower alkyl or halogen, and R₆ is
a) hydrazino, that is unsubstituted or one- to threefold substituted by optionally substituted alkyl and/or optionally substituted acyl,
b) cyclohexylamino, tetrahydro-4H-pyranyl-4-amino, pyrrolidine-3-amino, 2- or 3-tetrahydrofurylamino, all optionally substituted by amino, hydroxy, alkoxy, alkyl or alkoxyalkyl,
c) piperazinyl that is optionally substituted by amino, amino-lower alkyl, hydroxy, alkoxy, alkyl or alkoxyalkyl,
d) morpholinyl that is optionally substituted by amino, amino-lower alkyl, hydroxy, alkoxy, alkyl or alkoxyalkyl,
e) oxazolidinyl that is optionally substituted by amino, amino-lower alkyl, hydroxy, hydroxy-lower alkyl, alkoxy, alkyl or alkoxyalkyl,
f) thiazolidinyl that is optionally substituted by amino, amino-lower alkyl, hydroxy, hydroxy-lower alkyl, alkoxy, alkyl or alkoxyalkyl,
g) imidazolidinyl that is optionally substituted by amino, amino-lower alkyl, hydroxy, hydroxy-lower alkyl, alkoxy, alkyl or alkoxyalkyl,
h) amino or mono- or di-(lower alkyl)amino wherein the lower alkyl moieties are unsubstituted or substituted by one or more substitutents independently selected from the group consisting of unsubstituted amino, N-mono- or N,N-di-(lower alkyl)-amino, (lower alkoxy)-lower alkoxy, lower alkoxycarbonylamino, hydroxy-lower alkoxycarbonylamino, lower alkoxy-lower alkoxycarbonylamino, morpholinyl, hydroxy-lower alkylamino, cyano, halogen, oxo bound to a carbon that is not directly bound to a heteroatom, hydroximino, alkoximino, optionally substituted hydrazono, lower alkenyl, lower alkynyl, guanidyl, lower alkanoylamino, hydroxy-lower alkanoylamino, lower alkoxy-lower alkanoylamino, halo-lower alkanoylamino, lower alkylaminocarbonylamino, hydroxy-lower alkylaminocarbonylamino, lower alkoxy-lower alkylaminocarbonylamino, amidino, di-lower-alkylamino-cyclohexyl, carboxy, lower alkoxycarbonyl, hydroxy-lower alkoxycarbonyl, lower alkoxy-lower alkoxycarbonyl, lower alkylcarbonyldioxy (=lower alkoxycarbonyloxy), hydroxy-lower alkoxycarbonyloxy, lower alkoxy-lower alkoxycarbonyloxy, lower alkanoyloxy, halo-lower alkanoyloxy, hydroxy-lower alkanoyloxy, lower alkoxy-lower alkanoyloxy, carbamoyl, N-mono- or N,N-di-lower alkylcarbamoyl, N-(hydroxy-lower alkyl)carbamoyl, N-lower alkyl-N-hydroxy-lower alkyl-carbamoyl, N,N-di-(hydroxy-lower alkyl)-carbamoyl, N-hydroxy-carbamoyl, hydroxy, lower alkoxy, lower alkenyloxy, lower alkinyloxy, lower haloalkoxy, lower alkylthio, lower alkylsulfinyl, lower alkylsulfonyl, lower alkoxysilyl, 4-tetrahydro-4H-pyranyl, 3-pyrrolidinyl, 2- or 3-tetrahydrofuryl, 2- or 3-dihydrofuryl, piperazinyl, lower alkanoyl-piperazinyl formylpiperazinyl, optionally substituted heteroaryl and optionally substituted heteroaryloxy, i) optionally substituted alkanoylamino, optionally substituted alkenoylamino, optionally substituted alkynoylamino, optionally substituted mono- or di-alkylaminocarbonylamino, optionally substituted alkoxycarbonylamino, optionally substituted mono- or di-alkylaminosulfonylamino, optionally substituted mono- or di-alkylaminosulfoxylamino, j) N-(optionally substituted alkyl)-N-(optionally substituted lower alkanoyl)-amino, k) N-(optionally substituted alkyl)-N-(optionally substituted alkoxycarbonyl)-amino, l) N-(optionally substituted alkyl)-N—(N',N'-mono- or di-[optionally substituted alkyl]-aminocarbonyl)-amino, or m) N=C($R_7$,$R_8$) wherein $R_7$ is hydrogen, alkyl, amino, mono- or di-alkylamino and $R_8$ is amino, mono- or dialkylamino or wherein $R_7$ and $R_8$, together with the binding carbon atom, form a saturated five- to seven-membered ring with 0, 1 or 2 ring nitrogen atoms that is optionally substituted by one or more substituents;

or a salt thereof.

* * * * *